US012643893B2

(12) United States Patent
Byon et al.

(10) Patent No.: US 12,643,893 B2
(45) Date of Patent: Jun. 2, 2026

(54) HETEROARYL-PYRIDINIUM COMPOUND AND REDOX FLOW BATTERY COMPRISING THE SAME

(71) Applicants: Korea Advanced Institute of Science and Technology, Daejeon (KR); Pusan National University Industry-University Cooperation Foundation, Busan (KR)

(72) Inventors: Hye Ryung Byon, Daejeon (KR); Jung Min Joo, Busan (KR); Seongmo Ahn, Daejeon (KR); Jin Hyeok Jang, Busan (KR)

(73) Assignees: Korea Advanced Institute of Science and Technology, Daejeon (KR); Pusan National University Industry-University Cooperation Foundation, Busan (KR)

( * ) Notice: Subject to any disclaimer, the term of this patent is extended or adjusted under 35 U.S.C. 154(b) by 1087 days.

(21) Appl. No.: 17/658,242

(22) Filed: Apr. 6, 2022

(65) Prior Publication Data

US 2022/0332712 A1 Oct. 20, 2022

(30) Foreign Application Priority Data

Apr. 7, 2021 (KR) ........................ 10-2021-0045492
Mar. 23, 2022 (KR) ........................ 10-2022-0036142

(51) Int. Cl.
*C07D 417/04* (2006.01)
*C07D 401/04* (2006.01)
(Continued)

(52) U.S. Cl.
CPC ......... *C07D 417/04* (2013.01); *C07D 401/04* (2013.01); *C07D 413/04* (2013.01); *C07D 413/14* (2013.01); *H01M 8/08* (2013.01); *H01M 8/18* (2013.01); *H01M 2300/0025* (2013.01); *H01M 2300/0028* (2013.01)

(58) Field of Classification Search
CPC ........ H01M 8/08; H01M 8/18; C07D 417/04; C07D 401/04; C07D 413/04; C07D 413/14
See application file for complete search history.

(56) References Cited

FOREIGN PATENT DOCUMENTS

KR 10-2019-0080298 A 7/2019
WO WO-2018020586 A1 * 2/2018 .............. H01M 8/18

OTHER PUBLICATIONS

Savarino et al., "Voltammetric Behaviour of Heterocyclic Systems. Pyridyl-substituted Benzimidazoles, Benzoxazoles and Benzothiazoles," J Heterocyclic Chem., 34, pp. 1479-1485 (1997). (Year: 1997).*

(Continued)

*Primary Examiner* — Karie O'Neill Apicella
(74) *Attorney, Agent, or Firm* — Knobbe, Martens, Olson & Bear, LLP

(57) ABSTRACT

Provided are a heteroaryl-pyridinium compound and a redox flow battery including the same. The redox flow battery includes a positive electrode cell including a positive electrode and a posolyte solution; a negative electrode cell including a negative electrode and a negolyte solution; and a separator disposed between the positive electrode cell and the negative electrode cell. The negolyte solution is the electrolyte solution for a redox flow battery.

18 Claims, 17 Drawing Sheets

(a)
BTP 0.26 M
BOP
BIP
TP
DiMe-BTP (b)
TMAP-BTP 0.25 M
Hex-BTP 0.23 M
Dec-BTP 0.07 M
MOE-BTP 0.10 M
Di-BTP 0.10 M

(51) Int. Cl.
*C07D 413/04* (2006.01)
*C07D 413/14* (2006.01)
*H01M 8/08* (2016.01)
*H01M 8/18* (2006.01)

(56) References Cited

OTHER PUBLICATIONS

Jang, Jin Hyeok, et al., "Synthesis of Redox-Active Phenanthrene-Fused Heteroarenes by Palladium-Catalyzed C—H Annulation", Organic Letters 22.4 (Feb. 6, 2020): 1280-1285.
Vaid, Thomas P. et al., "An organic super-electron-donor as a high energy density negative electrolyte for nonaqueous low batteries", Chemical Communications 55.74 (2019): 11037-11040.
Wei, Xiaoliang, et al., "Radical compatibility with nonaqueous electrolytes and its impact on an all-organic redox flow battery", Angewandte Chemie International Edition 54.30 (2015): 8684-8687.
Wei, Xiaoliang et al., "A High-Current, Stable Nonaqueous Organic Redox Flow Battery", ACS Energy Letters (Sep. 5, 2016), 705-711.
Savarino et al., "Voltammetric Behaviour of Heterocyclic Systems. Pyridyl-substituted Benzimidazoles, Benzoxazoles and Benzothiazoles," J Heterocyclic Chem., 34, pp. 1479-1485, (1997).
Office Action received in Korean Patent Application No. 10-2022-0036142 dated Apr. 16, 2024.
Notice of Allowance in Korean Application No. 10-2022-0036142 dated Dec. 1, 2024 in 7 pages.

* cited by examiner (a)

BTP
0.26 M

BOP

BIP

TP

DiMe-BTP (b)

TMAP-BTP
0.25 M

Hex-BTP
0.23 M

Dec-BTP
0.07 M

MOE-BTP
0.10 M

Di-BTP
0.10 M

HETEROARYL-PYRIDINIUM COMPOUND AND REDOX FLOW BATTERY COMPRISING THE SAME

CROSS-REFERENCE TO RELATED APPLICATIONS

This application claims priority under 35 U.S.C. §119 to Korean Patent Application No. 10-2021-0045492, filed on Apr. 7, 2021, and Korean Patent Application No. 10-2022-0036142, filed on Mar. 23, 2022, in the Korean Intellectual Property Office, the disclosures of which is incorporated herein by reference in their entirety.

TECHNICAL FIELD

The following disclosure relates to a novel heteroaryl-pyridinium compound and a redox flow battery including the same.

BACKGROUND

In order to store an intrinsically intermittent energy source such as solar, wind, and hydro power in an economical and safe manner, a redox flow battery (RFB) has emerged. A redox flow battery (RFB) is one of energy storage systems (ESS) for overcoming temporal and geographic differences that occur between the production and consumption of electrical energy, and one type of rechargeable cell which stores electrical energy in the form of a chemical energy and converts the energy into an electrical energy form for use. It is potentially evaluated as an energy storage technology having high efficiency, which is used for a large-scale energy production.

The disclosure of this section is to provide background information relating to the present disclosure. Applicant does not admit that any information contained in this section constitutes prior art.

SUMMARY

Aqueous vanadium RFBs may be provided for a grid-scale and widely used energy storage system, but the capacity of a battery is 20 times lower than a lithium ion battery, and thus, the battery should be installed in a large capacity due to its low energy density. In addition, vanadium prices are rising, and an evolutionary development by the design of tunable redox materials such as new organic molecules and coordination complexes of high capacity, high voltage, and low cost, which may replace vanadium, so as to have a higher energy density to increase efficiency of building an energy storage device, is demanded.

Chemical tailoring based on fundamental reactivity can systematically modulate the redox potential, solubility, and chemical stability of redox substances. In addition, various synthetic methods facilitate the reduction of the material and synthesis costs without relying on the limited elemental resources. However, optimization of molecular design is still challenging as highly stable redox materials are required for the long-term performance of RFB s.

Non-aqueous RFBs can demonstrate high energy densities at high operating voltages. Since a non-aqueous medium is more stable even in a high negative potential than an aqueous solution, a cell voltage may be extended by using a redox electrolyte solution in a negative electrode side referred to as a "negolyte (or anolyte)" and adjusting its redox potential. However, to date, only a few viable negolytes have been reported. Although phenanthrene-fused heteroarenes, diquat derivatives, N-methylphthalimide, and 9-fluorenone showed promising redox potentials at −1.5~−2.0 V vs. the ferrocene/ferrocenium couple ($Fc/Fc^+$), the performances of the corresponding RFBs were not stable.

Meanwhile, as a representative of various redox active organic materials, there is a pyridinium cation having a substituent at a nitrogen position of pyridine, and a study thereon is actively underway. A viologen derivative is a material which is widely used for realizing multi-electron transport and reasonable stability of RFB performance, but its first redox potential is about −0.69 V vs. $Fc/Fc^+$, and the second redox event requires 400 mV of the total overpotential. In this regard, an alternative approach to introduce a desired chemical substituent to a single pyridinium core has been suggested. Typically, a pyridinium derivative including ester and acyl groups was used to lower a redox potential to −0.9 V to −1.1 V vs. $Fc/Fc^+$, but due to decomposition and protonation during a redox event, a significant capacity fading in RFB was caused.

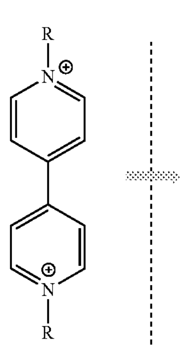

$E^{0'}$ -0.69 V

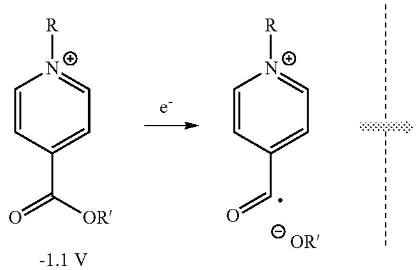

-1.1 V

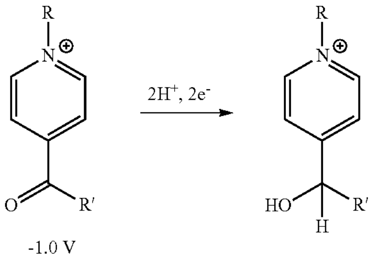

-1.0 V

As such, since a known pyridinium compound has limited stability and solubility in an organic solvent, there is difficulties in forming a battery which may be operated at a high concentration for a long time.

The other technical difficulty is incomplete installation of the full RFBs comprising a negolyte and a posolyte due to their severe crossover through a porous membrane. Due to these difficulties, galvanostatic evaluation has been often conducted using a symmetric cell including an electrolyte solution in which a posolyte and a negolyte are mixed.

However, this approach is unfeasible because of the double cost of the redox materials, limited solubility, and chemical instability of redox-induced molecules. Recently, the oligomerization of redox molecules was used to increase their size and suppressed the crossover issue in full RFB. However, most of these molecules still showed a low solubility.

As described above, numerous organic redox materials are chemically unstable and hardly dissolved in a non-aqueous medium, and due to the crossover of redox materials and the availability of limited membranes, long-term cyclability of the redox material in non-aqueous RFB is limited.

Therefore, development of a negative electrode active material having improved physical/chemical stability and a low negative potential is desperately needed.

In order to improve a redox flow battery in stability, solubility, and crossover of a redox material as described above, the present inventors developed a pyridinium redox material having a new structure with pyridinium as a core, and confirmed electrochemical stability in various solvents using the new pyridinium redox material, thereby completing embodiments of the present disclosure.

Thus, an embodiment of the present disclosure is directed to providing a novel heteroaryl-pyridinium compound having excellent redox stability and a low reduction potential.

Another embodiment of the present disclosure is directed to providing an electrolyte solution for a redox flow battery including the heteroaryl-pyridinium compound.

Still another embodiment of the present disclosure is directed to providing a redox flow battery including the electrolyte solution.

In one general aspect, a heteroaryl-pyridinium compound represented by the following Chemical Formula 1 or Chemical Formula 2 is provided.

[Chemical Formula 1]

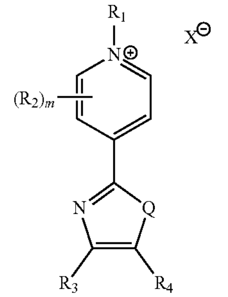

[Chemical Formula 2]

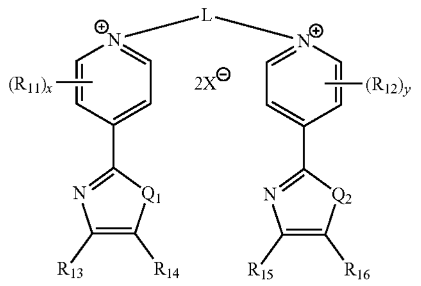

wherein $R_1$ is $C_1$-$C_2$oalkyl and the alkyl of Ru may be further substituted with $C_1$-$C_2$oalkoxy, cyano, or $*-\overset{\oplus}{N}R^aR^bR^cX^{\ominus}$;

$R^a$, $R^b$, and $R^c$ are independently of one another hydrogen or $C_1$-$C_{20}$alkyl;

L is $C_1$-$C_{20}$alkylene;

$R_2$, $R_{11}$, and Ru are independently of one another $C_1$-$C_{20}$alkyl;

m, x, and y are independently of one another an integer of 0 to 4;

$Q_1$, $Q_2$, and $Q_2$ are independently of one another NR', O, or S;

R' is hydrogen or $C_1$-$C_{20}$alkyl;

$R_3$, $R_4$, and $R_{13}$ to $R_{15}$ are hydrogen, or $R_3$ and $R_4$, $R_{13}$ and $R_{14}$, and $R_{15}$ and $R_{16}$ may be connected to each other to form a fused ring; and $X^-$ is an anion.

In another general aspect, an electrolyte solution for a redox flow battery includes the heteroaryl-pyridinium compound.

In still another general aspect, a redox flow battery includes the electrolyte solution.

Other features and aspects will be apparent from the following detailed description, the drawings, and the claims.

DETAILED DESCRIPTION OF EMBODIMENTS

Figure 1:
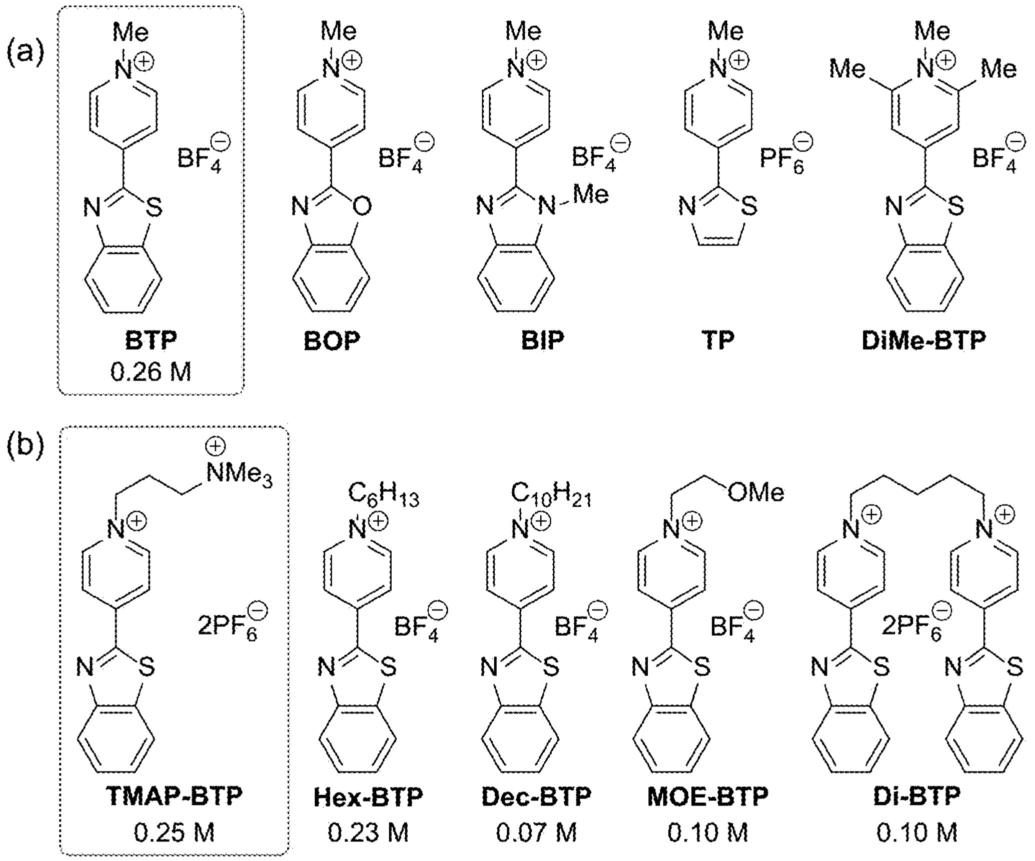
FIG. 1—Design of various pyridinium derivatives. (a) Effect of the heteroaromatic ring. (b) Effect of the N-alkyl substituent. [The molar concentration indicates the solubility in MeCN.]

Hereinafter, the present disclosure will be described in detail with reference to the accompanying drawings.

When a drawing is illustrated, the drawing is provided by way of example so that the idea of the present disclosure may be sufficiently conveyed to a person skilled in the art. Therefore, the present disclosure is not limited to the provided drawings, but may be embodied in many different forms, and the drawings may be exaggerated in order to clear the spirit of the present disclosure.

Technical terms and scientific terms used herein have the general meaning understood by those skilled in the art to which the present disclosure pertains unless otherwise defined, and a description for the known function and configuration which may unnecessarily obscure the gist of the present disclosure will be omitted in the following description and the accompanying drawings.

In addition, the singular form used in the present specification may be intended to also include a plural form, unless otherwise indicated in the context.

In the present specification, the expression, "comprise" is an open-ended description having a meaning equivalent to the expression such as "provided", "contain", "include", "have", or "is/are characterized", and does not exclude elements, materials or processes which are not further listed. In addition, the expression, "substantially consisting of . . . " means that other elements, materials, or processes which are not listed together with specified elements, materials, or processes may be present in an amount which does not have an unacceptable significant influence on at least one basic and novel technical idea of the disclosure. In addition, the expression, "consisting of" means that only the described elements, materials, or processes are present.

In the present specification, when the positional relationship of two parts is described using the expressions such as "on", "on the upper portion of", "on the lower portion of", and "beside", one or more other parts may exist between the two parts unless the expression "right" or "directly" is used. The positional relationship such as "upper portion", "upper surface", "lower portion", or "lower surface" is only described based on the drawing, and does not represent an absolute positional relationship. That is, the positions of "upper portion" and "lower portion", or "upper surface" and "lower surface" may be changed depending on the observation position.

The term "$C_A$-$C_B$" in the present specification refers to "the number of carbons being A or more and B or less".

The term "alkyl" in the present specification refers to a monovalent straight chain or branched chain saturated hydrocarbon composed of only carbon and hydrogen atoms. An example of alkyl may include methyl, ethyl, propyl, isopropyl, butyl, isobutyl, t-butyl, pentyl, hexyl, heptyl, octyl, nonyl, decyl, and the like, but is not limited thereto.

The term "alkoxy" in the present specification refers to an *—O-alkyl, wherein "alkyl" is as defined above. A specific example thereof includes methoxy, ethoxy, propoxy, isopropoxy, butoxy, isobutoxy, t-butoxy, and the like, but is not limited thereto.

The term in the present specification, a substituent including alkyl in addition to "alkyl" and "alkoxy" refers to a group derived from a linear or branched hydrocarbon. In addition, alkyl and a substituent including alkyl according to embodiments of the present disclosure have a short chain of 1 to 7 carbon atoms, and may be selected from the group consisting of methyl, ethyl, propyl, butyl, and the like, but are not limited thereto.

In the present specification, the term negolyte (anolyte or negative electrolyte) solution is an electrolyte solution in which a negative electrode active material is dissolved and the term posolyte (catholyte or positive electrolyte) solution is an electrolyte solution in which a positive electrode active material is dissolved. The positive electrode active material refers to a redox pair which is dissolved in a posolyte solution, and it means that charging is carried out when the redox pair is changed to a higher side of two oxidation states, that is, when oxidation occurs. The negative electrode active material refers to a redox pair which is dissolved in a negolyte solution, and it means that charging is carried out to a lower side of two oxidation states of the redox pair, that is, when reduction occurs.

An embodiment of the present disclosure provides a novel heteroaryl-pyridinium compound having excellent redox stability and a low reduction potential.

The heteroaryl-pyridinium compound according to an embodiment may be represented by the following Chemical Formula 1 or Chemical Formula 2:

[Chemical Formula 1]

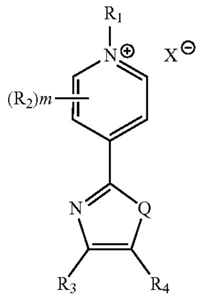

[Chemical Formula 2]

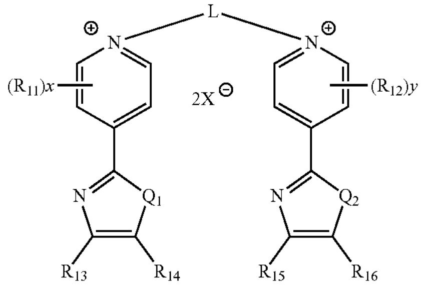

wherein $R_1$ is $C_1$-$C_{20}$alkyl and the alkyl of Ri may be further substituted with $C_1$-$C_2$oalkoxy, cyano, or $* —\overset{\oplus}{N}R^aR^bR^cX^{\ominus}$;

$R^a$, $R^b$, and $R^c$ are independently of one another hydrogen or $C_1$-$C_{20}$alkyl;

L is $C_1$-$C_{20}$alkylene;

$R_2$, $R_{11}$, and $R_{12}$ are independently of one another $C_1$-$C_{20}$alkyl;

m, x, and y are independently of one another an integer of 0 to 4;

Q, $Q_1$, and $Q_2$ are independently of one another NR', O, or S;

R' is hydrogen or $C_1$-$C_{20}$alkyl;

$R_3$, $R_4$, and $R_{13}$ to $R_{15}$ are hydrogen, or $R_3$ and $R_4$, $R_{13}$ and $R_{14}$, and $R_{15}$ and $R_{16}$ may be connected to each other to form a fused ring; and $X^-$ is an anion.

The heteroaryl-pyridinium compound according to the present disclosure has a structure in which 5-membered heteroazole is introduced to a C4-position of pyridinium, and extends π-conjugation of a pyridinium core and provides an electron attracting effect due to a C═N bond similar to imine to stabilize a radical species produced by one electron reduction. That is, introduction of 5-membered heteroazole may increase stability of a redox-active pyridinium core. In addition, the heteroaryl-pyridinium compound may have a high solubility in various solvent, in particular, non-aqueous solvents, and thus, may be used as a negolyte solution of a non-aqueous redox flow battery.

In an embodiment, in Chemical Formula 1, $R_3$ and $R_4$, $R_{13}$ and $R_{14}$, and $R_{15}$ and $R_{16}$ may be connected by

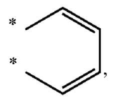

respectively to form a fused ring.

The heteroaryl-pyridinium compound according to an embodiment may be represented by the following Chemical Formula 3, Chemical Formula 4, or Chemical Formula 5:

[Chemical Formula 3]

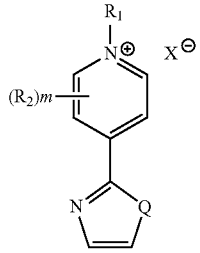

[Chemical Formula 4]

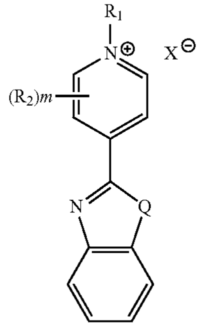

[Chemical Formula 5]

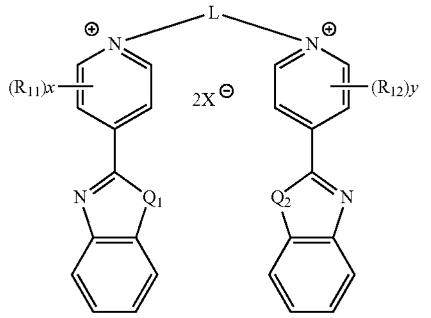

wherein $R_1$ is $C_1$-$C_{10}$alkyl, $C_1$-$C_{10}$alkoxy$C_1$-$C_{10}$alkyl, cyano$C_1$-$C_{10}$alkyl, or —$L_1$—$N^+R^aR^bR^cX^-$;

$L_1$ is $C_1$-$C_{10}$alkylene;

$R^a$, $R^b$, and $R^c$ are independently of one another hydrogen or $C_1$-$C_{10}$alkyl;

$L_1$ is $C_1$-$C_{10}$alkylene;

$R_2$, $R_{11}$, and $R_{12}$ are independently of one another $C_1$-$C_{10}$alkyl;

m, x, and y are independently of one another an integer of 0 to 2;

Q, $Q_1$, and $Q_2$ are independently of one another NR', O, or S;

R' is hydrogen or $C_1$-$C_{10}$alkyl;

$X^-$ is an anion.

In an embodiment, in the heteroaryl-pyridinium compound of Chemical Formula 3, $R_1$ may be $C_1$-$C_{10}$alkyl, m may be 0, and Q may be S.

In an embodiment, in the heteroaryl-pyridinium compound of Chemical Formula 4, $R_1$ may be $C_1$-$C_{10}$alkyl, $C_1$-$C_{10}$alkoxy$C_1$-$C_{10}$alkyl, or —$L_1$—$N^+R^aR^bR^cX^-$, $L_1$ may be $C_1$-$C_{10}$alkylene, $R^a$, $R^b$ and $R^c$ may be independently of one another $C_1$-$C_{10}$alkyl, $R_2$ may be $C_1$-$C_{10}$alkyl, m may be an integer of 0 to 2, Q may be NR', O, or S, R' may be $C_1$-$C_{10}$alkyl, and $X^-$ may be an anion.

In an embodiment, in the heteroaryl-pyridinium compound of Chemical Formula 5, L may be $C_3$-$C_{10}$alkylene, x and y may be 0, and $Q_1$ and $Q_2$ may be S.

In an embodiment, $X^-$ is a monovalent anion, and as an example, $X^-$ may be a halide, tetrafluoroborate ($BF_4^-$), hexafluorophosphate ($PF_6^-$), acetate ($CH_3COO^-$), propionate ($CH_3CH_2COO^-$), trifluoroacetate ($CF_3COO^-$), benzoate ($C_6H_5COO^-$), nitrate ($NO_3^-$), cyanide ($CN^-$), thiocyanate ($SCN^-$), cyanate ($OCN^-$), perchlorate ($ClO_4^-$), $C_1$-$C_{10}$alkoxide, $C_6$-$C_{10}$aryloxide, trifluoromethane sulfonate ($CF_3SO_3^-$), tosylate ($CH_3C_6H_4SO_3^-$), hexafluoroantimonate ($SbF_6^-$), azide ($N_3^-$), tetraphenyl borate ($BPh_4^-$), or bistriflimide ($TFSI^-$).

In the heteroaryl-pyridinium compound according to an embodiment, $X^-$ may be tetrafluoroborate ($BF_4^-$), hexafluorophosphate ($PF_6^-$), or bistriflimide ($TFSI^-$), in terms of implementing better solubility in a non-aqueous solvent.

The heteroaryl-pyridinium compound according to an embodiment may be represented by the following Chemical Formula 4-1 or Chemical Formula 4-2:

[Chemical Formula 4-1]

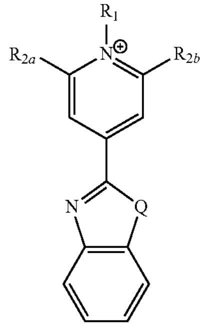

[Chemical Formula 4-2]

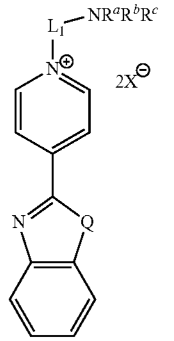

wherein $R_1$ is $C_1$-$C_{10}$alkyl or $C_1$-$C_{10}$alkoxy$C_1$-$C_{10}$alkyl;

$L_1$ is $C_1$-$C_{10}$alkylene;

$R^a$, $R^b$, and $R^c$ are independently of one another $C_1$-$C_{10}$alkyl;

$R_{2a}$ and $R_2$b are hydrogen or $C_1$-$C_{10}$alkyl;

Q is NR', O, or S;

R' is $C_1$-$C_{10}$alkyl; and $X^-$ is an anion.

In a specific example, in Chemical Formulae 4-1 and 4-2, Q may be S.

In particular, the heteroaryl-pyridinium compound according to an embodiment may be represented by Chemical Formula 4-2 in which a cationic ammonium functional group is introduced to a N-substituent of a pyridinium core, and in this case, crossover in which an electrolyte solution and an electrolyte which penetrate an anion exchange membrane in a redox flow battery and are present in both electrodes move toward each other may be efficiently suppressed.

The heteroaryl-pyridinium compound according to an embodiment may be selected from the following structures, but is not limited thereto:

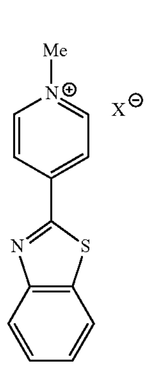
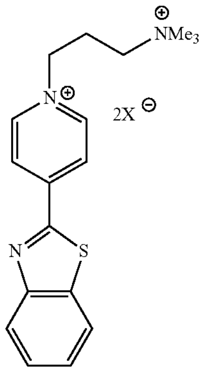
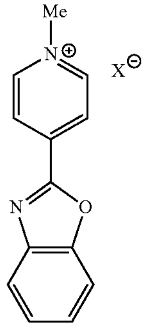
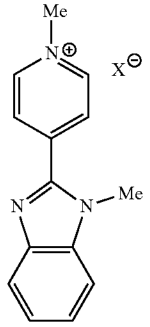
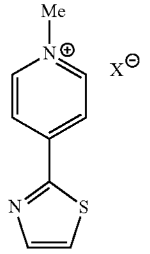
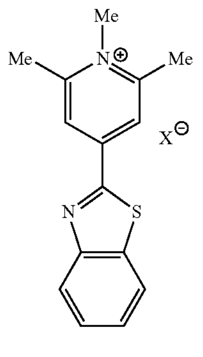
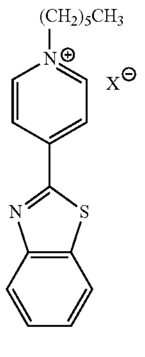
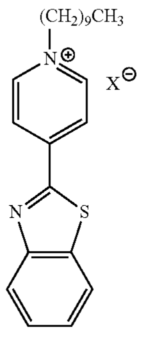

-continued

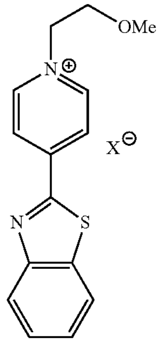
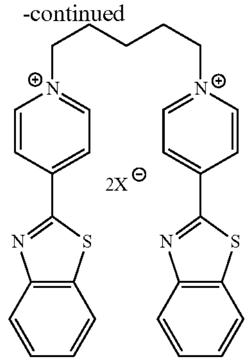

wherein $X^-$ is an anion.

In a specific example, $X^-$ may be tetrafluoroborate ($BF4^-$), hexafluorophosphate ($PF_6^-$), or bistriflimide ($TFSI^-$).

The heteroaryl-pyridinium compound according to an embodiment may undergo a reversible oxidation/reduction reaction, and has excellent redox stability and low negative potential redox properties together with excellent solubility in non-aqueous solvents as well as aqueous solvents, and thus, may be efficiently used in an electrolyte solution for a redox flow battery and may implement a redox flow battery having a high potential difference and a high energy density.

Another embodiment of the present disclosure provides an electrolyte solution for a redox flow battery including the heteroaryl-pyridinium compound.

The electrolyte solution for a redox flow battery according to an embodiment may include the heteroaryl-pyridinium compound alone or two or more thereof.

The electrolyte solution for a redox flow battery according to an embodiment may further include a solvent, and the solvent may be an aqueous solvent, a non-aqueous solvent, an ionic liquid, or a mixture thereof.

In an embodiment, the solvent may be an aqueous solvent, and as the aqueous solvent, sulfuric acid, hydrochloric acid, phosphoric acid, methanesulfonic acid, ithium hydroxide, sodium hydroxide, potassium hydroxide and cesium hydroxide, or a combination thereof may be used.

In an embodiment, the solvent may be a non-aqueous solvent, and the non-aqueous solvent acts as a medium in which ions involved in an electrochemical reaction of a battery may move and may be any one or more selected from the group consisting of carbonate-based solvents, ester-based solvents, ether-based solvents, ketone-based solvents, alcohol-based solvents, aprotic solvents, and ionic liquids.

In a specific example, the non-aqueous solvent may be any one or more selected from the group consisting of dimethylacetamide (DMA), acetonitrile (MeCN), dimethyl carbonate, diethyl carbonate, methylethyl carbonate, dimethyl formamide, propylene carbonate, ethylene carbonate, N-methyl-2-pyrrolidone, fluoroethylene carbonate, γ-butyrolactone, dimethylsulfoxide, diethyleneglycol dimethylether, triethyleneglycol, dimethylether, tetraethyleneglycol dimethylether, acetone, acetylacetone, 1,4-dioxane, 1,2-dimethoxyethane, 1,2-diethoxyethane, dichloromethane, 1,2-dichloroethane, nitrobenzene, nitromethane, tetrahydrofuran, 2-methyltetrahydrofuran, 2,4-dimethyltetrahydrofuran, methoxybenzene, diglyme, triglyme, tetraglyme, 4-methyl-2-pentanone, propionitrile, butyronitrile, isobutyronitrile, benzonitrile, sulfolane, dimethylthioformamide, methyl acetate, ethyl acetate, ethanol, and methanol.

In an embodiment, the solvent may be an ionic liquid, and the ionic liquid is a material which is only formed of a cation and an anion and has a melting point of 100° C. or lower. In an embodiment, the solvent imparts flame retardancy to the electrolyte or acts as a medium which may aid in ion movement in an electrolyte. The ionic liquid may be an ammonium, imidazolium, morpholinium, phosphonium, piperidinium, pyridinium, pyrrolidinium, or a sulfonium-based ionic liquid having a central element such as N, P, and S as a cation of the ionic liquid.

Specifically, the ionic liquid may include any one anion selected from the group consisting of tetrafluoroborate ($BF_4^-$), hexafluorophosphate ($PF_6^-$), triflate ($CF_3SO_3^-$), bis (trifluoromethanesulfonyl)imide (TFSI, $N(CF_3O_2)_2^-$), (bis (fluorosulfonyl)imide; FSI, $N(FSO_2)_2^-$), bis(pentafluoroethylsulfonyl)imide (BETI, $N(CF_3CF_2SO_2)_2^-$), trifluoroacetate ($CF_3COO^-$), acetate ($CH_3COO^-$), tosylate, methanesulfonate, halide, dicyanamide ($N(CN)_2^-$), and the like, and any one cation selected from the group consisting of trimethylammonium ($[TMHA]^+$), tetramethylammonium ($[TMA]^+$), tetraethylammonium ($[TEA]^+$), triethylmethylammonium ($[Et_3MeN]^+$), butyltrimethylammonium ($[Me_3BuN]^+$), methyltributylammonium ($[Bu_3MeN]^+$), hexyltributylammonium ($[HxBu_3N]^+$), N,N-diethyl-N-methyl-N-(2-methoxyethyl)ammonium ($[DEME]^+$), 1-ethyl-3-methylimidazolium ($[EMI]^+$), 1-butyl-3-methylimidazolium ($[BMI]^+$), 1-methylimidazolium ($[Hmim]^+$), 1-ethyl-2,3-dimethylimidazolium ($[EDiMIM]^+$), 2,3-dimethyl-1-propylimidazolium ($[DMPIM]^+$), 1-butyl-2,3-dimethylimidazolium ($[BDiMIM]^+$), tributylmethylphosphonium ($[Bu_3MeP]^+$), triethylpentylphosphonium ($[P2225]^+$), triethyloctylphosphonium ($[P2228]^+$), 1-ethyl-1-methyl piperidinium ($[C_2mPip]^+$), 1-methyl-1-propylpiperidinium ($[C_3mPip]^+$), 1-butyl-1-methylpiperidinium ($[C_4mPip]^+$), 1-methylpyridinium ($[MP]^+$), 1-ethylpyridinium ($[EP]^+$), 1-propylpyridinium ($[PP]^+$), 1-butyl pyridinium ($[BP]^+$), 1-ethyl-1-methylpyrrolidinium ($[C_2mpyr]^+$), 1-methyl--propylpyrrolidinium ($[C_3mpyr]^+$), 1-butyl-1-methylpyrrolidinium ($[C_4mpyr]^+$), trimethylsulfonium triethylsulfonium ($[TES]^+$), tributylsulfonium ($[TBS]^+$), and mixtures thereof.

More specifically, an example of the ionic liquid may include any one or more selected from butyltrimethylammonium bis(trifluoromethanesulfonyl)imide ($[Me_3BuN]^+[N(CF_3SO_2)_2]^-$), methyltributylammonium bi s(trifluoromethanesulfonyl)imi de ($[Bu_3MeN]^+[N(CF_3SO_2)_2]^-$), hexyltributylammonium bis(trifluoromethanesulfonyl)imide ($[HxBu_3N]^+[N(CF_3SO_2)_2]^-$), 1-ethyl-3-methylimidazolium bis(trifluoromethanesulfonyl)imide ($[EMI]^+[N(CF_3SO_2)_2]^-$), 1-ethyl-3-methylimidazolium tetrafluoroborate ($[EMI]^+[BF_4]^-$), 1-ethyl-3-methylimidazolium triflate ($[EMI]^+[CF_3SO_3]^-$), 1-butyl-3-methylimidazolium hexafluorophosphate ($[BMI]^+[PF_6]^-$), 1-butyl-3-methylimidazolium bis(trifluoromethanesulfonyl)imide ($[BMI]^+[N(CF_3SO_2)_2]^-$), 1-butyl-3-methylimidazolium tetrafluoroborate ($[BMI]^+[BF_4]^-$), 1-butyl-3-methylimidazolium trifluoroacetate ($[BMI]^+[CF_3COO]^-$, 1-butyl-3-methylimidazolium acetate ($[BMI]^+[CH_3COO]^-$), 1-butyl-3-methylimidazolium dicyanamide ($[BMI]^+[N(CN)_2]^-$), 1-butyl-3-methylimidazolium triflate ($[BMI]^+[CF_3SO_3]^-$), tributylmethylphosphonium bis(trifluoromethanesulfonyl) imide ($[Bu_3MeP]^+[N(CF_3SO_2)_2]^-$), 1-methyl-1-propylpiperidinium bis(trifluoromethanesulfonyl)imide ($[C_3mPip]^+[N(CF_3SO_2)_2]^-$), 1-butylpyridinium tetrafluoroborate ($[BP]^+[BF_4]^-$), 1-butylpyri dinium bis(trifluoromethanesulfonyl) imide ($[BP]^+[N(CF_3SO_2)_2]^-$), 1-methyl-1-propylpyrrolidinium bis(trifluoromethanesulfonyl)imide ($[C_3mpyr]+[N(CF_3SO_2)_2]^-$), 1-methyl-1-propylpyrrolidinium dicyanamide ($[C_3mpyr]^+[N(CN)_2]^-$), 1-butyl-1-methylpyrrolidinium bis(trifluoromethanesulfonyl)imide ($[C_4mpyr]^+[N(CF_3SO_2)_2]^-$), triethylsulfonium bis(trifluoromethanesulfonyl)imide ($[TES]+[N(CF_3SO_2)_2]^-$), and tributylsulfonium bis(trifluoromethanesulfonyl)imide ($[Bu_3S]^+[N(CF_3SO_2)_{2]}^-$).

In a specific example, the electrolyte solution for a redox flow battery may be an electrolyte solution for a non-aqueous redox flow battery including the heteroaryl-pyridinium compound and a non-aqueous solvent.

The electrolyte solution for a redox flow battery according to an embodiment may further include a supporting electrolyte, and the supporting electrolyte may be any one or more selected from the group consisting of an alkylammonium salt, a lithium salt, a sodium salt, and a potassium salt.

The alkylammonium salt may be formed of a combination of any one or more anions selected from a halide, $PF_6^-$, $BF_4^-$, $AsF_6^-$, $ClO_4^-$, $CF_3SO^-$, $C(SO_2CF_3)_3^-$, $N(CF_3SO_2)_2^-$, and $CH(CF_3SO_2)_2^-$ and a tetra$C_1$-$C_4$alkylammonium cation, but is not limited thereto.

As a specific example, the alkylammonium salt may be any one or more selected from tetrabuthylammonium tetrafluoroborate ($TBABF_4$), tetrabuthylammonium perchlorate ($TBAClO_4$), tetrabutylammonium hexafluorophosphate ($TBAPF_6$), tetrabutylammonium chloride (TBACl), tetrabutylammonium bromide (TBABr), tetrabutylammonium iodide (TBAI), tetrabutylammonium bistriflimide (TBATFSI), tetraethylammonium tetrafluoroborate ($TEABF_4$), tetraethylammonium hexafluorophosphate ($TEAPF_6$), tetraethylammonium perchlorate ($TEAClO_4$), and tetraethylammonium bistriflimide (TEATFSI).

The lithium salt, the sodium salt, and the potassium salt may be formed of a combination of any one anion selected from a halide, $NO_3^-$, $NO_2^-$, $PF_6^-$, $BF_4^-$, $AsF_6^-$, $SbF_6^-$, $ClO_4^-$, $CH_3SO_3^-$, $CF_3SO_3^-$, $C(SO_2CF_3)_3^-$, $N(CF_3SO_2)_2^-$, $N(SOF)_2^-$, $N(SO_2C_2F_5)_2^-$, and $CH(CF_3SO_2)_2^-$ and a lithium, sodium, or potassium cation.

Specifically, the lithium salt may be any one or more selected from LiCl, LiI, LiBr, $LiNO_3$, $LiNO_2$, $LiPF_6$, $LiBF_4$, $LiAsF_6$, $LiSbF_6$, $LiClO_4$, $LiCH_3SO_3$, $LiCF_3SO_3$, $LiC(SO_2CF_3)_3$, $LiN(CF_3SO_2)_2$, $LiN(SOF)_2$, $LiN(SO_2C_2F_5)_2$, and $LiCH(CF_3SO_2)_2$.

In a specific example, the sodium salt may be any one or more selected from NaCl, NaI, NaBr, $NaNO_3$, $NaNO_2$, $NaPF_6$, $NaBF_4$, $NaClO_4$, $NaCF_3SO_3$, $NaC(SO_2CF_3)_3$, $NaN(CF_3SO_2)_2$, $NaN(SOF)_2$, $NaN(SO_2C_2F_5)_2$, and $NaCH(CF_3SO_2)_2$.

In a specific example, the potassium salt may be any one or more selected from KCl, KI, KBr, $KNO_3$, $KNO_2$, $KPF_6$, $KBF_4$, $KClO_4$, $KCF_3SO_3$, $KC(SO_2CF_3)_3$, $KN(CF_3SO_2)_2$, $KN(SOF)_2$, $KN(SO_2C_2F_5)_2$, and $KCH(CF_3SO_2)_2$.

In a specific example, the solvent may be a non-aqueous solvent, specifically acetonitrile, and the supporting electrolyte may be an ammonium salt.

In the electrolyte solution for a redox flow battery according to an embodiment, the heteroaryl-pyridinium compound is an organic active material for a negolyte solution, that is, a negative electrode active material, and has an excellent solubility in a solvent, is chemically stable, and has a low negative potential to allow stable electron movement, and thus, the electrolyte solution for a redox flow battery may be used as a negolyte solution of a redox flow battery.

Another embodiment of the present disclosure provides a redox flow battery including the electrolyte solution.

The redox flow battery according to an embodiment includes a positive electrode cell including a positive electrode and a posolyte solution; a negative electrode cell including a negative electrode and a negolyte solution, disposed opposite to one side of the positive electrode cell; and a separator disposed between the positive electrode cell and the negative electrode cell, wherein the negolyte solution may be the electrolyte solution.

The redox flow battery is divided into a positive electrode cell and a negative electrode cell by a separator, and the positive electrode cell and the negative electrode cell may include a positive electrode and a negative electrode, respectively. The positive electrode cell is connected to a positive electrode tank for supplying and discharging a posolyte solution through a pipe, the negative electrode cell is connected to a negative electrode tank for supplying and discharging a negolyte solution through a pipe, the negolyte solution and the posolyte solution are circulated through the pump, respectively, and in the positive electrode and the negative electrode, charge and discharge may occur by a valence change reaction of ions.

In an embodiment, the posolyte solution may include one or more selected from 1,1'-dimethylferrocene, a salt of (ferrocenylmethyl)trimethylammonium, a salt of bis((3-trimethylammonio)propyl)ferrocene, 5,10-dimethyl-5,10-dihydrophenazine, 5,10-bis(2-methoxyethyl)-5,10-dihydrophenazine, (2,2, 6,6-tetramethylpiperidin-1-yl)oxyl (TEMPO), 4-hydroxy-(2,2,6,6-tetramethylpiperidin-1-yl) oxyl (4-hydroxy-TEMPO),4-amino-(2,2,6,6-tetramethylpiperidin-1-yl)oxyl (4-amino-TEMPO), a salt of N,N,N-2,2,6,6-heptamethylpiperidinyloxy-4-ammonium (TMA-TEMPO), a salt of $N^1,N^1,N^1,N^3,N^3$,2,2,6,6-nonamethyl-$N^3$-(piperidiny oxy)propane-1,3-bis(ammonium), a salt of 4-[3-(trimethylammonio)propoxy]-2,2,6,6-tetramethylpiperidine-1-oxyl (TMAP-TEMPO), N-ethylphenothiazine, N-ethyl-3,7-dimethylphenothiazine, N-ethyl-3,7-dimethoxyphenothiazine, N-(2-(2-methoxyethoxy)ethyl)phenothiazine, 3,7-dimethoxy-N-(2-(2-methoxyethoxy)ethyl) phenothiazine, 3 , 7-b i s(2-(2-methoxyethoxy)ethoxy)-N-(2-(2-methoxyethoxy)ethyl)phenothiazine, 2,3-dimethyl-1, 4-dimethoxybenzene, 2,5-dimethyl-1,4-dimethoxybenzene, 1,4-di-tert-butyl-2-methoxy-5-(2-methoxy ethoxy)benzene), 1,4-di-tert-butyl-2-methoxy-5-(2-(2-methoxyethoxy) ethoxy)benzene, 1,4-di-tert-butyl-2,5-bis(2-methoxyethoxy) benzene, 1,4-di-tent-butyl-2, 5-b i s(2-(2-methoxyethoxy) ethoxy)benzene, a salt of N-(2,3-bis(dii sopropylamino)cycl oprop-2-en- 1-yli dene)-N-isopropylpropan-2-aminium, a salt of 2,3-bis(diisopropylamino)-1-(methylthio)cycloprop-2-en-1-ylium, and the like.

The salt compound included in the posolyte solution, specifically, salt compounds of (ferrocenylm ethyl)trim ethyl amm onium, bis((3-trim ethyl amm oni o)propyl)ferro cene, N,N,N-2,2,6,6-heptamethylpiperidinyloxy-4-ammonium (TMA-TEMPO), nonamethyl-$N^3$-(piperidinyloxy)propane-1,3-bis(ammonium), 4-[3-(trimethylammonio)propoxy]-2, 2,6,6-tetramethylpiperidine-1-oxyl (TMAP-TEMPO), N-(2, 3-bis(diisopropylamino)cycloprop-2-en-1-ylidene)-N-isopropylpropan-2-aminium), and 2,3-bis(diisopropylamino)-1-(methylthio)cycloprop-2-en-1-ylium may be salts with a monovalent anion.

The monovalent anion forming the salt compound included in the posolyte solution may include a halide, tetrafluoroborate ($BF_4$), hexafluorophosphate ($PF_6$), acetate ($CH_3COO^-$), propionate ($CH_3CH_2COO^-$), trifluoroacetate ($CF_3COO^-$), benzoate ($C_6H5COO^-$), nitrate ($NO_3^-$), cyanide ($CN^-$), thiocyanate ($SCN^-$), cyanate ($OCN^-$), perchlorate ($ClO_4$), $C_1$-$C_{10}$alkoxide, $C_6$-$C_{12}$aryloxide, trifluoromethane sulfonate ($CF_3SO_3^-$), tosylate ($CH_3C_6H_4$ $SO_3$), hexafluoroantimonate ($SbF_6^-$), azide ($N_3^-$), tetraphenyl borate ($BPh_4^-$), bistriflimide ($TFSI^-$), and the like, but is not limited thereto.

In a specific example, the posolyte solution may include a salt compound of bis((3-trimethylammonio)propyl)ferrocene, and specifically, may include 1,1'-bis-[3-(trimethylammonio)propyl]ferrocene dibis-trifluoromethanesulfonimi date (BTMAP-Fc·$2TFSI^-$).

In an embodiment, the separator serves to prevent crossover between active material ions of the posolyte solution and the negolyte solution and allow only transfer of charge carrier ions of a supporting electrolyte, and may be an ion exchange membrane, and may be used without limitation as long as it is an ion exchange membrane used in a typical redox flow battery.

In an embodiment, the ion exchange membrane may be an anion exchange membrane (AEM) which mainly passes negative ions and blocks positive ion movement, and as a specific example, includes Fumasep FAS (FuMA-Tech GmbH, Germany), Fumasep®FAPQ (FuMA-Tech GmbH, Germany), and the like.

The redox flow battery according to an embodiment may have a high potential difference and a high energy density by adopting a negolyte solution including the heteroaryl-pyridinium compound having high redox stability, a low reduction potential, and excellent solubility as an organic active material for a negolyte solution. Thus, the redox flow battery is appropriate for a use requiring a high capacity and a high output such as electric vehicles as well as a typical use such as mobile phones and portable computers, and may be combined with internal combustion engines, fuel cells, supercapacitors, and the like to be used in hybrid vehicles, and the like. In addition, the redox flow battery may be used in all other uses requiring a high output and a high voltage.

Hereinafter, the present disclosure will be described in detail through the following examples. The following examples are only illustrative of the present disclosure and are not construed as limiting the present disclosure.

[Synthesis]

Materials

For syntheses, all chemicals were purchased from Sigma-Aldrich or TCI Korea. BTMAP-Fc (1,1-bis[3-(trimethylammonio)propyl]ferrocene dichloride) (>98.0%) and $TBAPF_6$ (tetrabutylammonium hexafluorophosphate) (>98.0%) were purchased from TCI Korea. LiTFSI (bis(trifluoromethane) sulfonimide lithium salt) (99.95%), TBATFSI (tetrabutylammonium bis-trifluoromethanesulfonimidate) (>99.0%), $TBABF_4$ (tetrabutylammonium tetraflouoroborate) (99%), and MeCN (anhydrous acetonitrile, 99.8%) were purchased from Sigma-Aldrich.

All salts were dried at 100° C. under vacuum for 24 h, and all solvents were dried using activated 4 Å molecular sieves in an argon (Ar)-filled glove box prior to use.

Instrumentation for the Characterization of Synthesized Compounds

Flash chromatography was performed on 40-63 μm silica gel using indicated eluents. $^1H$ and $^{13}C$ NMR spectra were recorded in $CDCl_3$, DMSO-$d_6$, and $CD_3CN$ using a Bruker AVANCE 300 MHz, 400 MHz, and 500 MHz Fourier transform NMR spectrometer. Infrared (IR) spectra are recorded using Agilent Cary 630 FTIR Spectrophotometer and reported as absorption wavenumbers ($cm^{-1}$). High-resolution mass spectra (HRMS) were acquired on high-resolution mass spectrometers: Q-TOF (Agilent Technologies, 6530Accurate-Mass Q-TOF LC/MS, ionization mode: ESI).

Preparation Example 1

Preparation of 2-(pyridin-4-yl)benzo[d]thiazole

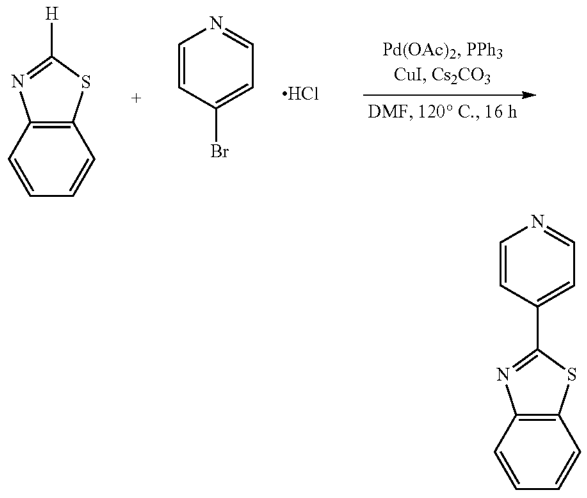

To a solution of benzothiazole (2.0 g, 14.8 mmol) and N,N-dimethylformamide (DMF) (30.0 mL, 0.50 M) in a 40 mL-glass vial were added 4-bromopyridine hydrochloride (4.3 g, 22.2 mmol), $Cs_2CO_3$ (14.5 g, 44.4 mmol), CuI (317.0 mg, 1.7 mmol), $Pd(OAc)_2$ (41.5 mg, 0.2 mmol), and $PPh_3$ (97.0 mg, 0.4 mmol) under an Ar atmosphere. After the reaction mixture was stirred in a preheated reaction block at 120° C. for 16 h, it was cooled to 25° C. The reaction mixture was treated with an ammonium hydroxide solution (15% $NH_3$ in $H_2O$, 25 mL) and EtOAc (25 mL) and transferred to a 250 mL separatory funnel. The organic layer was collected, and the aqueous layer was extracted with EtOAc (15 mL×2). The combined organic layers were washed with brine (15 mL), dried over sodium sulfate, and filtered. Purification by flash column chromatography (hexanes/EtOAc=2:1) provided 2-(pyridin-4-yl)benzo[d]thiazole as a white solid (2.9 g, 91% yield).

$^1H$ NMR (400 MHz, $CDCl_3$) δ 8.78 (d, J=6.2 Hz, 2H), 8.16-8.11 (m, 1H), 7.98-7.93 (m, 3H), 7.58-7.53 (m, 1H), 7.50-7.44 (m, 1H).

Preparation Example 2

Preparation of 2-(pyridin-4-yl)benzo[d]oxazole

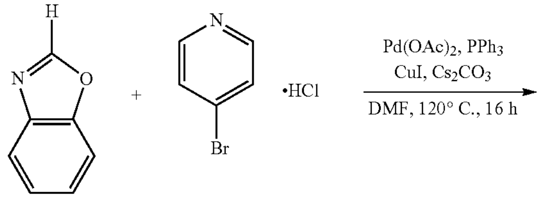

-continued

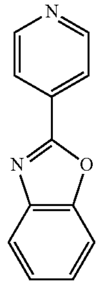

To a solution of benzoxazole (500 mg, 4.2 mmol) and DMF (8.4 mL, 0.50M) in a 40 mL-glass vial were added 4-bromopyridine hydrochloride (1.2 g, 6.3 mmol), $Cs_2CO_3$ (4.1 g, 12.6 mmol), CuI (89.9 mg, 0.5 mmol), $Pd(OAc)_2$ (11.8 mg, 0.05 mmol), and $PPh_3$ (27.5 mg, 0.1 mmol) under an Ar atmosphere. After the reaction mixture was stirred in a preheated reaction block at 120° C. for 16 h, it was cooled to 25° C. The reaction mixture was treated with an ammonium hydroxide solution (15% $NH_3$ in $H_2O$, 25 mL) and EtOAc (25 mL) and transferred to a 250 mL separatory funnel. The organic layer was collected, and the aqueous layer was extracted with EtOAc (15 mL×2). The combined organic layers were washed with brine (15 mL), dried over sodium sulfate, and filtered. Purification by flash column chromatography (hexanes/EtOAc=2:1) provided 2-(pyridin-4-yl)benzo[d]oxazole as a white solid (620 mg, 75% yield). $^1H$ NMR (400 MHz, $CDCl_3$) δ 8.85-8.81 (m, 2H), 8.12-8.08 (m, 2H), 7.86-7.81 (m, 1H), 7.67-7.62 (m, 1H), 7.46-7.43 (m, 1H), 7.43-7.39 (m, 1H).

Preparation Example 3

Preparation of 1-methyl-2-(pyridin-4-yl)-1H-benzo[d]imidazole

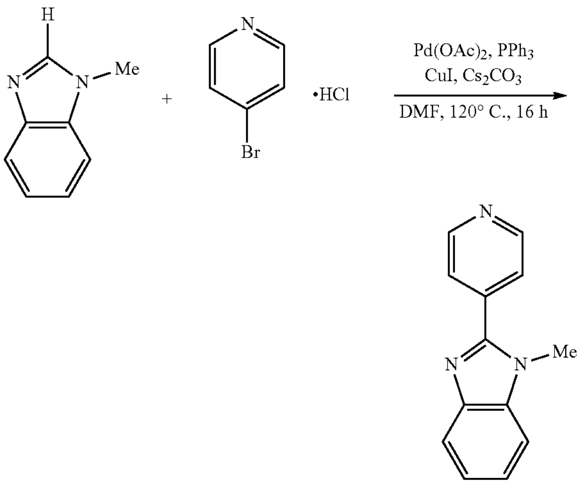

To a solution of 1-methylbenzimidazole (500 mg, 3.8 mmol) and DMF (8 mL, 0.50 M) in a 40 mL-glass vial were added 4-bromopyridine hydrochloride (1.1 g, 5.7 mmol), $Cs_2CO_3$ (3.7 g, 11.3 mmol), CuI (81.1 mg, 0.4 mmol), $Pd(OAc)_2$ (10.6 mg, 0.05 mmol), and $PPh_3$ (24.8 mg, 0.1 mmol) under an Ar atmosphere. After the reaction mixture was stirred in a preheated reaction block at 120° C. for 16 h, it was cooled to 25° C. The reaction mixture was treated with an ammonium hydroxide solution (15% $NH_3$ in $H_2O$, 25 mL) and EtOAc (25 mL) and transferred to a 250 mL separatory funnel. The organic layer was collected, and the aqueous layer was extracted with EtOAc (15 mL×2). The combined organic layers were washed with brine (15 mL), dried over sodium sulfate, and filtered. Purification by flash column chromatography (hexanes/EtOAc=2:1) provided 1-methyl-2-(pyridin-4-yl)-1H-benzo[d]imidazole as a yellow solid (316 mg, 40% yield).

$^1H$ NMR (300 MHz, DMSO-$d_6$) δ 8.82 (d, J=4.6 Hz, 2H), 7.92-7.82 (m, 1H), 7.72 (d, J=4.5 Hz, 2H), 7.46-7.41 (m, 1H), 7.40-7.32 (m, 2H), 3.95 (s, 3H).

Preparation Example 4

Preparation of 2-(pyridin-4-yl)thiazole

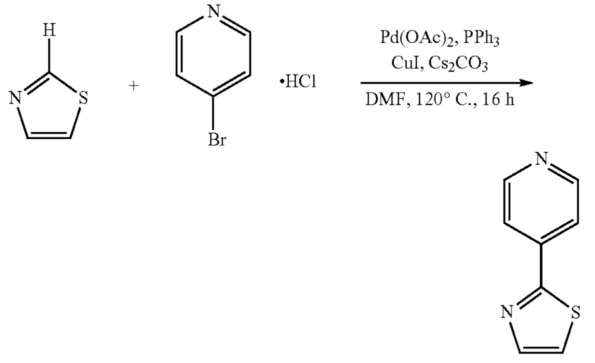

To a solution of thiazole (500 mg, 5.9 mmol) and DMF (11.8 mL, 0.50 M) in a 40 mL-glass vial were added 4-bromopyridine hydrochloride (1.7 g, 8.8 mmol), $Cs_2CO_3$ (5.7 g, 17.6 mmol), CuI (126 mg, 0.7 mmol), $Pd(OAc)_2$ (16.5 mg, 0.07 mmol), and $PPh_3$ (38.5 mg, 0.15 mmol) under an Ar atmosphere. After the reaction mixture was stirred in a preheated reaction block at 120° C. for 16 h, it was cooled to 25° C. The reaction mixture was treated with an ammonium hydroxide solution (15% $NH_3$ in $H_2O$, 25 mL) and EtOAc (25 mL) and transferred to a 250 mL separatory funnel. The organic layer was collected, and the aqueous layer was extracted with EtOAc (15 mL×2). The combined organic layers were washed with brine (15 mL), dried over sodium sulfate, and filtered. Purification by flash column chromatography (hexanes/EtOAc=3:1) provided 2-(pyridin-4-yl)thiazole as a yellow solid (400 mg, 42% yield).

mp 53-55° C.; IR (film) 3035, 1590, 1402, 1254, 1211, 1149 $cm^{-1}$; $^1H$ NMR (400 MHz, $CDCl_3$) δ 8.74-8.70 (m, 2H), 7.97 (d, J=3.2 Hz, 1H), 7.85-7.82 (m, 2H), 7.48 (d, J=3.2 Hz, 1H); $^{13}C$ NMR (100 MHz, DMSO-$d_6$) δ 165.4, 150.7, 144.5, 140.3, 120.8, 120.4; HRMS$^+$ (ESI) calcd. for $C_8H_7N_2S^+$ $[M]^+$ 163.0324, found 163.0321.

Preparation Example 5

Preparation of 2-(2,6-dimethylpyridin-4-yl)benzo[d]thiazole

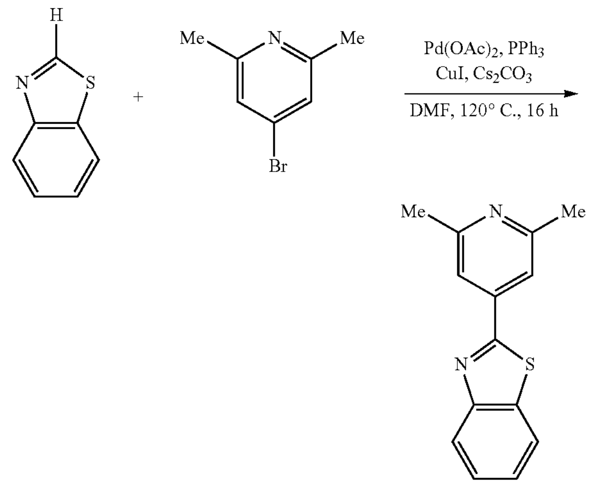

To a solution of benzothiazole (1.5 g, 11.1 mmol) and DMF (22 mL, 0.50M) in a 40 mL-glass vial were added 4-bromo-2,6-dimethylpyridine (3.1 g, 16.6 mmol), $Cs_2CO_3$ (5.4 g, 16.6 mmol), CuI (238.1 mg, 1.3 mmol), $Pd(OAc)_2$ (31.4 mg, 0.14 mmol), and $PPh_3$ (73.4 mg, 0.28 mmol) under an Ar atmosphere. After the reaction mixture was stirred in a preheated reaction block at 120° C. for 16 h, it was cooled to 25° C. The reaction mixture was treated with an ammonium hydroxide solution (15% $NH_3$ in $H_2O$, 25 mL) and EtOAc (25 mL) and transferred to a 250 mL separatory funnel. The organic layer was collected, and the aqueous layer was extracted with EtOAc (15 mL×2). The combined organic layers were washed with brine (15 mL), dried over sodium sulfate, and filtered. Purification by flash column chromatography (hexanes/EtOAc=2:1) provided 2-(2,6-dimethylpyridin-4-yl)benzo[d]thiazole as a white solid (2.5 g, 93% yield).

$^1H$ NMR (300 MHz, $CDCl_3$) δ 8.12 (d, J=8.1 Hz, 1H), 7.95 (d, J=8.0 Hz, 1H), 7.62 (s, 2H), 7.54 (t, J=7.7 Hz, 1H), 7.45 (t, J=7.6 Hz, 1H), 2.64 (s, 6H).

Preparation Example 6

Preparation of 1,1'-bis[3-(trimethylammonio)propyl] ferrocene dibis-trifluoromethanesulfonimidate (B TMAP-Fc·2TFSI$^-$)

To a solution of 1,1' -bis[3-(trimethylammonio)propyl] ferrocene dichloride (1.0 g, 2.2 mmol) and DI-water (22 mL, 0.10 M) in a 70 mL-glass vial was added LiTFSI (1.9 g, 6.6 mmol). The reaction mixture was stirred at 25° C. for 16 h. The reaction mixture was treated with DI-water (20 mL), and the precipitated solid was filtered by reduced pressure. The resulting residue was collected and dried under a vacuum. After drying, BTMAP-Fc2TFSI$^-$ was obtained as a yellow solid (2.0 g, 95% yield).

$^1H$ NMR (500 MHz, $CD_3CN$) δ 4.08-4.07 (t, J=1.8 Hz, 4H), 4.05 (t, J=1.85 Hz, 4H), 3.19 (m, 4H), 2.99 (s, 18H), 2.38 (t, J=7.62 Hz, 4H), 1.91-1.85 (m, 4H).

Example 1

Preparation of 4-(benzo[d]thiazol-2-yl)-1-methylpyridin-1-ium iodide ($BTP^+ \cdot I^-$)

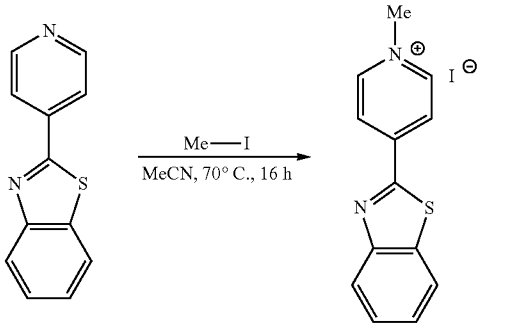

$BTP^+ \bullet I$-

To a solution of 2-(pyridin-4-yl)benzo[d]thiazole (Preparation Example 1, 1.0 g, 4.7 mmol) and MeCN (9.4 mL, 0.50 M) in a 40 mL-glass vial was added iodomethane (1.1 g, 5.7 mmol) under an Ar atmosphere. After the reaction mixture was stirred in a preheated reaction block at 70° C. for 16 h, it was cooled to 25° C. The reaction mixture was treated with EtOAc (10 mL), and the precipitated solid was filtered by reduced pressure. The resulting residue was collected and under a vacuum. After drying, $BTP^+ \cdot I^-$ was obtained as a yellow solid (1.5 g, 65% yield). $BTP^+ \cdot I^-$ displayed identical $^1H$ and $^{13}C$ NMR spectra as $BTP^+ \cdot TFSI^-$.

Example 2

Preparation of 4-(benzo[d]thiazol-2-yl)-1-methylpyridin-1-ium tetrafluoroborate ($BTP^+ \cdot BF_4^-$)

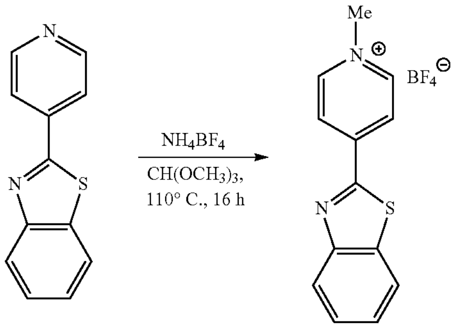

$BTP^+ \bullet BF_4$-

$BTP^+ \cdot BF_4^-$ was prepared according to the literature [Green Chem. 2014, 16, 4098-4101.].

To a solution of 2-(pyridin-4-yl)benzo[d]thiazole Preparation Example 1, 1.0 g, 4.7 mmol) and trimethyl orthoformate (2.5 g, 24 mmol) in a 40 mL-glass vial was added ammonium tetrafluoroborate (593 mg, 5.7 mmol) under an Ar atmosphere. After the reaction mixture was stirred in a preheated reaction block at 110° C. for 16 h, it was cooled to 25° C. The reaction mixture was treated with EtOAc (10 mL), and the precipitated solid was filtered by reduced pressure. The resulting residue was collected and under a vacuum. After drying, $BTP^+ \cdot BF_4^-$ was obtained as a white solid (1.5 g, 96% yield). $BTP^+ \cdot BF_4^-$ displayed identical $^1H$ and $^{13}C$ NMR spectra as $BTP^+ \cdot TFSI^-$.

Example 3

Preparation of 4-(benzo[d]thiazol-2-yl)-1-methylpyridin-1-ium bistriflimide ($BTP^+ \cdot TFSI^-$)

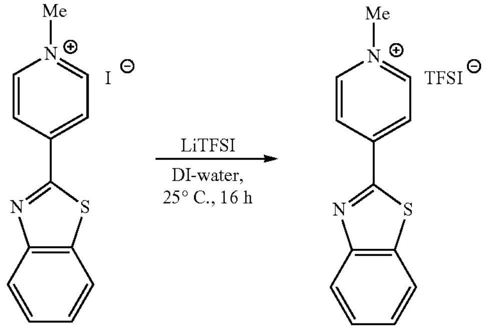

$BTP^+ \bullet I$- $BTP^+ \bullet TFSI$-

To a solution of 4-(benzo[d]thiazol-2-yl)-1-methylpyridin-1-ium iodide (Example 1, 500 mg, 1.4 mmol) and DI-water (14 mL, 0.10 M) in a 40 mL-glass vial was added LiTFSI (Lithium bistrifluoromethanesulfonimidate) (608 mg, 2.1 mmol). The reaction mixture was stirred at 25° C. for 16 h. The reaction mixture was treated with DI-water (10 mL), and the precipitated solid was filtered by reduced pressure. The resulting residue was collected and dried under vacuum. After drying, $BTP^+ \cdot TFSI^-$ was obtained as a white solid (683 mg, 95% yield).

mp 110-112° C.; IR (film) 3377, 1644, 1526, 1487, 1346, 1183 $cm^{-1}$; $^1H$ NMR (400 MHz, DMSO-$d_6$) δ 9.12 (d, J=6.9 Hz, 2H), 8.75 (d, J=6.9 Hz, 2H), 8.39-8.31 (m, 1H), 8.30-8.23 (m, 1H), 7.74-7.68 (m, 1H), 7.68-7.62 (m, 1H), 4.40 (s, 3H); $^{13}C$ NMR (100 MHz, DMSO-$d_6$) δ 161.3, 153.4, 146.6, 146.0, 136.2, 127.8, 127.7, 124.5, 124.4, 123.1, 119.6 (q, J=321.9 Hz, $CF_3$), 47.9; $HRMS^+$ (ESI) calcd. for $C_{11}H_{11}N_2S^+$ $[M]^+$ 227.0637, found 227.0635; $HRMS^-$ (ESI) calcd. for $C_2F_6NO_4S_2^-$ $[M]^{-279.9178}$, found 279.9177.

Example 4

Preparation of 4-(benzo[d]thiazol-2-yl)-1-(3-(trimethylammonio)propyl)pyridin-1-ium bromide ($TMAP\text{-}BTP^{2+} \cdot 2Br^-$)

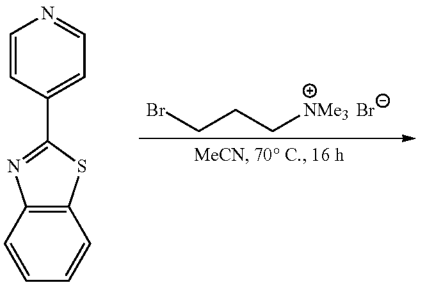

-continued

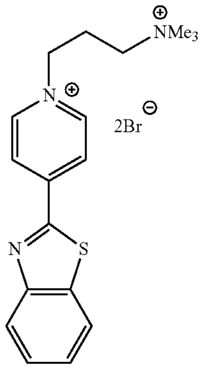

TMAP-BTP$^{2+}$•2Br-

To a solution of 2-(pyridin-4-yl)benzo[d]thiazole (Preparation Example 1, 1.0 g, 4.7 mmol) and MeCN (9.4 mL, 0.50 M) in a 40 mL-glass vial was added (3-bromopropyl) trimethylammonium bromide (1.5 g, 5.7 mmol) under an Ar atmosphere. After the reaction mixture was stirred in a preheated reaction block at 70° C. for 16 h, it was cooled to 25° C. The reaction mixture was treated with EtOAc (10 mL), and the precipitated solid was filtered by reduced pressure. After drying, TMAP-BTP$^{2+}$·2Br$^-$ was obtained as a white solid (2.1 g, 97% yield). TMAP-BTP$^{2+}$·2Br$^-$ displayed identical $^1$H and $^{13}$C NMR spectra as TMAP-BTP$^{2+}$ ·2TSFI$^-$.

Example 5

Preparation of 4-(benzo[d]thiazol-2-yl)-1-(3-(trimethylammonio)propyl)pyridin-1-ium hexafluorophosphate (TMAP-BTP$^{2+}$·2PF$_6^-$)

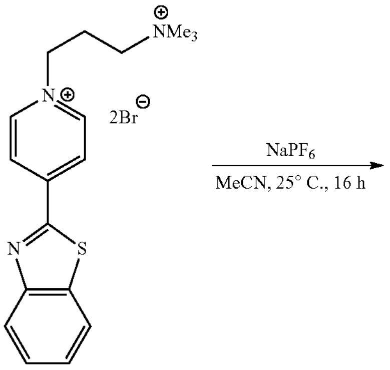

TMAP-BTP$^{2+}$•2Br$^-$

-continued

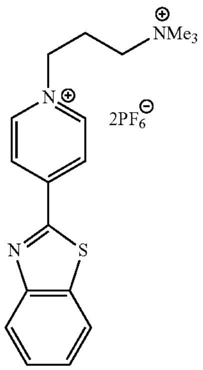

TMAP-BTP$^{2+}$•2PF$_6^-$

To a solution of 4-(benzo[d]thiazol-2-yl)-1-(3-(trimethylammonio)propyl)pyridin-1-ium bromide (Example 4, 1.9 g, 4.0 mmol) and MeCN (8.0 mL, 0.50 M) in a 40 mL-glass vial was added NaPF$_6$ (1.5 g, 8.7 mmol). The reaction mixture was stirred at 25° C. for 16 h. The reaction mixture was treated with DI-water (10 mL), and the precipitated solid was filtered by reduced pressure. The resulting residue was collected and dried under a vacuum. After drying, TMAP-BTP$^{2+}$·2Pf$_6^-$ was obtained as a white solid (1.2 g, 50% yield). TMAP-BTP$^{2+}$·2PF$_6^-$ displayed identical $^1$H and $^{B}$C NMR spectra as TMAP-BTP$^{2+}$·2TFSI$^-$.

Example 6

Preparation of 4-(benzo[d]thiazol-2-yl)-1-(3-(trimethylammonio)propyl)pyridin-1-ium bistriflimide (TMAP-BTP$^{2+}$·2TFSI$^-$)

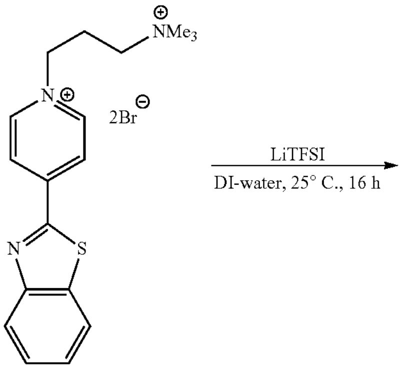

TMAP-BTP$^{2+}$•2Br$^-$

-continued

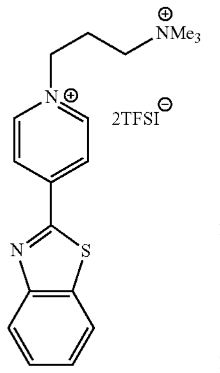

TMAP-BTP$^{2+}$•2TFSI$^{-}$

To a solution of 4-(benzo[d]thiazol-2-yl)-1-(3-(trimethylammonio)propyl)pyridin-1-ium bromide (Example 4, 1.0 g, 2.1 mmol) and DI-water (21 mL, 0.10 M) in a 40 mL-glass vial was added LiTFSI (1.8 g, 6.3 mmol). The reaction mixture was stirred at 25° C. for 16 h. The reaction mixture was treated with DI-water (20 mL), and the precipitated solid was filtered by reduced pressure. The resulting residue was collected and dried under vacuum. After drying, TMAP-BTP$^{2+}$·2TFSI$^{-}$ was obtained as a white solid (1.7 g, 97% yield).

mp 131-133° C.; IR (film) 3064, 1637, 1520, 1483, 1324, 1052 cm$^{-1}$; $^{1}$H NMR (400 MHz, DMSO-d$_6$) δ 9.23 (d, J=7.0 Hz, 2H), 8.85 (d, J=7.0 Hz, 2H), 8.39-8.34 (m, 1H), 8.30-8.26 (m, 1H), 7.74-7.69 (m, 1H), 7.69-7.63 (m, 1H), 4.73 (t, J=7.3 Hz, 2H), 3.45-3.37 (m, 2H), 3.08 (s, 9H), 2.50-2.43 (m, 2H); $^{13}$C NMR (100 MHz, DMSO-d$_6$) δ 161.2, 153.4, 146.7, 146.1, 136.2, 127.9, 127.8, 125.1, 124.4, 124.3, 119.5 (q, J=321.9 Hz, CF$_3$), 61.8, 57.7, 52.5, 24.2; HRMS$^{+}$ (ESI) calcd. for $C_{18}H_{23}N_3S^{2+}$ [M]$^{2+}$ 313.1602, found 313.1600; HRMS$^{-}$ (ESI) calcd. for $C_2F_6NO_4S_2^{-}$ [M]$^{-279.9178}$, found 279.9177.

Example 7

Preparation of 4-(benzo[d]oxazol-2-yl)-1-methylpyridin-1-ium tetrafluoroborate (BOP$^{+}$·BF$_4^{-}$)

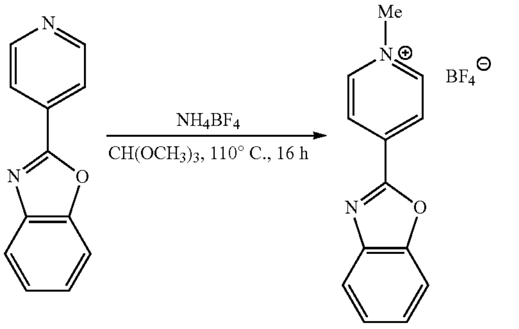

BOP$^{+}$•BF$_4^{-}$

To a solution of 2-(pyridin-4-yl)benzo[d]oxazole (Preparation Example 2, 300 mg, 1.5 mmol) and trimethyl orthoformate (812 mg, 7.7 mmol) in a 40 mL-glass vial was added ammonium tetrafluoroborate (192 mg, 1.8 mmol) under an Ar atmosphere. After the reaction mixture was stirred in a preheated reaction block at 110° C. for 16 h, it was cooled to 25° C. The reaction mixture was treated with EtOAc (10 mL), and the precipitated solid was filtered by reduced pressure. The resulting residue was collected and dried under vacuum. After drying, BOP$^{+}$·BF$_4^{-}$ was obtained as a white solid (374 mg, 82% yield).

mp 283-285° C.; IR (film) 3093, 1645, 1506, 1475, 1349, 1281 cm$^{-1}$; $^{1}$H NMR (400 MHz, DMSO-d$_6$) δ 9.20-9.11 (m, 2H), 8.77-8.6 (m, 2H), 8.00-7.93 (m, 1H), 7.92-7.86 (m, 1H), 7.65-7.58 (m, 1H), 7.57-7.50 (m, 1H), 4.44 (s, 3H); $^{13}$C NMR (100 MHz, DMSO-d$_6$) δ 157.6, 150.8, 146.8, 141.1, 140.0, 128.2, 126.1, 124.5, 121.2, 111.7, 48.1; HRMS (ESI) calcd. for $C_{13}H_{11}N_2O^{+}$ [M]$^{+}$ 211.0866, found 211.0868.; HRMS$^{+}$ (ESI) calcd. BF$_4^{-}$ [M]$^{-}$ 87.0035, found 87.0036.

Example 8

Preparation of 1-methyl-4-(1-methyl-1H-benzo[d]imidazol-2-yl)pyridin-1-ium tetrafluoroborate (BIP$^{+}$·BF$_4^{-}$)

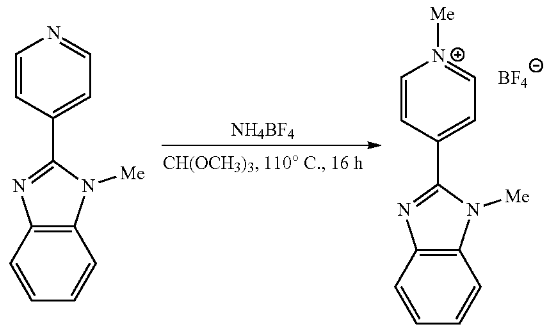

BIP$^{+}$•BF$_4^{-}$

To a solution of 1-methyl-2-(pyridin-4-yl)-1H-benzo[d]imidazole (Preparation Example 3, 647 mg, 3.1 mmol) and trimethyl orthoformate (1.6 g, 15.4 mmol) in a 40 mL-glass vial was added ammonium tetrafluoroborate (388 mg, 3.7 mmol) under an Ar atmosphere. After the reaction mixture was stirred in a preheated reaction block at 110° C. for 16 h, it was cooled to 25° C. The reaction mixture was treated with EtOAc (10 mL), and the precipitated solid was filtered by reduced pressure. The resulting residue was collected and under a vacuum. After drying, BIP$^{+}$·BF$_4^{-}$ was obtained as a white solid (500 mg, 52% yield).

$^{1}$H NMR (300 MHz, DMSO-d$_6$) δ 9.12 (d, J=6.6 Hz, 2H), 8.63 (d, J=6.6 Hz, 2H), 7.92-7.72 (m, 2H), 7.46 (t, J=7.6 Hz, 1H), 7.37 (t, J=7.2 Hz, 1H), 4.41 (s, 3H), 4.09 (s, 3H).

Example 9

Preparation of 1-methyl-4-(thiazol-2-yl)pyridin-1-ium tetrafluoroborate ($TP^{+}\cdot BF_4^{-}$)

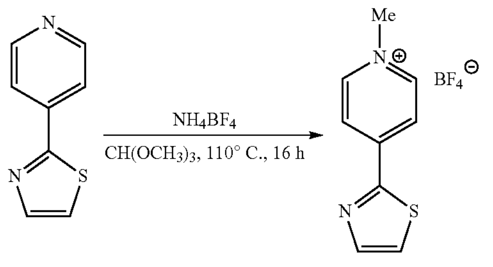

$TP^{+}\cdot BF_4^{-}$

To a solution of 2-(pyridin-4-yl)thiazole (Preparation Example 4, 200 mg, 1.2 mmol) and trimethyl orthoformate (654 mg, 6.2 mmol) in a 40 mL-glass vial was added ammonium tetrafluoroborate (155 mg, 1.5 mmol) under an Ar atmosphere. After the reaction mixture was stirred in a preheated reaction block at 110° C. for 16 h, it was cooled to 25° C. The reaction mixture was treated with EtOAc (10 mL), and the precipitated solid was filtered by reduced pressure. The resulting residue was collected and under a vacuum. After drying, $TP^{+}\cdot BF_4^{-}$ was obtained as a white solid (280 mg, 86% yield).

mp 132-134° C.; IR (film) 3113, 1646, 1343, 1173, 1129, 1051 $cm^{-1}$; $^{1}H$ NMR (400 MHz, DMSO-$d_6$) δ 9.03 (d, J=6.9 Hz, 2H), 8.60 (d, J=7.0 Hz, 2H), 8.32-8.25 (m, 2H), 4.35 (s, 3H); $^{13}C$ NMR (100 MHz, DMSO-$d_6$) δ 160.8, 146.4, 146.1, 145.8, 127.2, 123.3, 47.6; $HRMS^{+}$ (ESI) calcd. for $C_9H_9N_2S^{+}$ $[M]^{+}$ 177.0481, found 177.0481; $HRMS^{-}$ (ESI) calcd. for $BF_4^{-}$ $[M]^{-}$ 87.0035, found 87.0037.

Example 10

Preparation of 4-(benzo[d]thiazol-2-yl)-1,2,6-trimethylpyridin-1-ium tetrafluoroborate ($DiMe\text{-}BTP^{+}\cdot BF_4^{-}$)

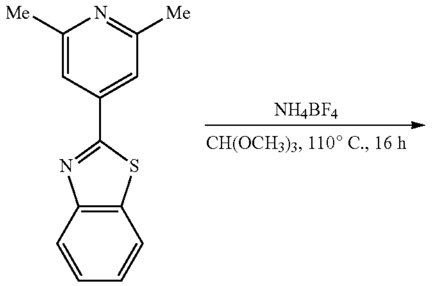

-continued

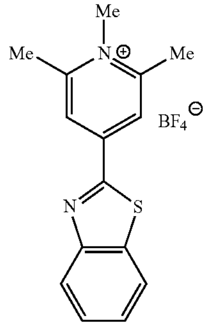

$DiMe\text{-}BTP^{+}\bullet BF_4^{-}$

To a solution of 2-(2,6-dimethylpyridin-4-yl)benzo[d]thiazole (Preparation Example 5, 1.0 g, 4.2 mmol) and trimethyl orthoformate (2.2 g, 20.8 mmol) in a 40 mL-glass vial was added ammonium tetrafluoroborate (524 mg, 5.0 mmol) under an Ar atmosphere. After the reaction mixture was stirred in a preheated reaction block at 110° C. for 16 h, it was cooled to 25° C. The reaction mixture was treated with EtOAc (10 mL), and the precipitated solid was filtered by reduced pressure. The resulting residue was collected and under a vacuum. After drying, $DiMe\text{-}BTP^{+}\cdot BF_4^{-}$ was obtained as a white solid (1.5 g, 96% yield).

mp 252-254° C.; IR (film) 3083, 1635, 1576, 1504, 1375, 1054 $cm^{-1}$; $^{1}H$ NMR (400 MHz, DMSO-$d_6$) δ 8.56 (s, 2H), 8.39-8.33 (m, 1H), 8.29-8.22 (m, 1H), 7.73-7.63 (m, 2H), 4.09 (s, 3H), 2.92 (s, 6H); $^{13}C$ NMR (100 MHz, DMSO-$d_6$) δ 161.5, 157.2, 153.2, 144.6, 136.0, 127.7, 127.6, 124.1, 123.4, 123.1, 40.4, 21.3; $HRMS^{+}$ (ESI) calcd. for $C_{15}H_{15}N_2S^{+}$ $[M]^{+}$ 255.0950, found 255.0950; $HRMS^{-}$ (ESI) calcd. for $BF_4^{-}$ $[M]^{-}$ $^{87.0035}$, found 87.0033.

Example 11

Preparation of 4-(benzo[d]thiazol-2-yl)-1-hexylpyridin-1-ium bromide ($Hex\text{-}BTP^{+}\cdot Br^{-}$)

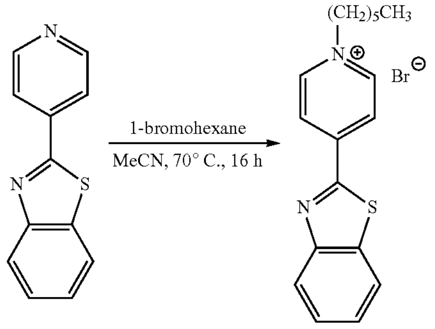

$Hex\text{-}BTP^{+}\bullet Br^{-}$

To a solution of 2-(pyridin-4-yl)benzo[d]thiazole (Preparation Example 1, 1.0 g, 4.7 mmol) and MeCN (9.4 mL, 0.50 M) in a 40 mL-glass vial was added 1-bromohexane (933 mg, 5.7 mmol) under an Ar atmosphere. After the reaction mixture was stirred in a preheated reaction block at 70° C. for 16 h, it was cooled to 25° C. The reaction mixture was treated with EtOAc (10 mL), and the precipitated solid was filtered by reduced pressure. The resulting residue was collected and d under a vacuum. After drying, $Hex\text{-}BTP^{+}$ $\cdot Br^-$ was obtained as a yellow solid (602 mg, 34% yield). Hex-BTP$^+\cdot$Br$^-$ displayed identical $^1$H and $^{13}$C NMR spectra as Hex-BTP$^+\cdot BF_4^-$.

Example 12

Preparation of 4-(benzo[d]thiazol-2-yl)-1-hexylpyridin-1-ium tetrafluoroborate (Hex-BTP$^+\cdot BF_4^-$)

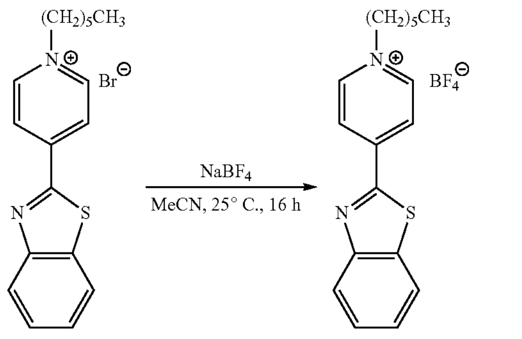

Hex-BTP$^+$•Br$^-$ Hex-BTP$^+$•BF$_4^-$

To a solution of 4-(benzo[d]thiazol-2-yl)-1-hexylpyridin-1-ium bromide (Example 11, 0.6 g, 1.6 mmol) and MeCN (3.2 mL, 0.50 M) in a 40 mL-glass vial was added $NaBF_4$ (193 mg, 1.8 mmol). The reaction mixture was stirred at 25° C. for 16 h. The reaction mixture was treated with DI-water (10 mL), and the precipitated solid was filtered by reduced pressure. The resulting residue was collected and dried under a vacuum. After drying, Hex-BTP$^+\cdot BF_4^-$ was obtained as a white solid (550 mg, 89% yield).

mp 165-167° C.; IR (film) 3075, 2927, 1640, 1490, 1312, 1034 cm“‘; $^1$H NMR (400 MHz, DMSO-d$_6$) δ 9.24-9.17 (m, 2H), 8.77-8.69 (m, 2H), 8.37-8.29 (m, 1H), 8.27-8.21 (m, 1H), 7.72-7.60 (m, 2H), 4.66 (t, J=7.5 Hz, 2H), 2.02-1.89 (m, 2H), 1.36-1.23 (m, 6H), 0.92-0.82 (m, 3H); $^{13}$C NMR (100 MHz, DMSO-d$_6$) δ 161.4, 153.3, 146.2, 145.8, 136.2, 127.8, 127.7, 124.9, 124.3, 123.2, 60.7, 30.7, 30.6, 21.9, 13.8; HRMS$^+$ (ESI) calcd. for $C_{18}H_{21}N_2S^+$ [M]$^+$ 297.1420, found 297.1424; FIRMS” (ESI) calcd. for $BF_4^-$ [M]$^-$ 87.0035, found 87.0032.

Example 13

Preparation of 4-(benzo[d]thiazol-2-yl)-1-decylpyridin-1-ium bromide (Dec-BTP$^+\cdot$Br$^-$)

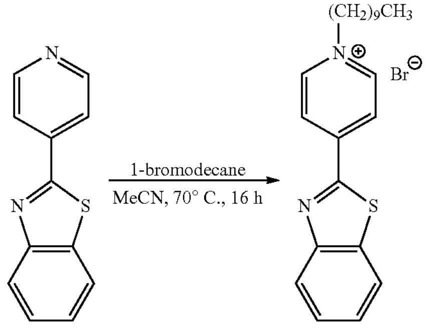

Dec-BTP$^+$•Br$^-$

To a solution of 2-(pyridin-4-yl)benzo[d]thiazole (Preparation Example 1, 0.9 g, 4.3 mmol) and MeCN (8.6 mL, 0.50 M) in a 40 mL-glass vial was added 1-bromodecane (1.3 mg, 5.1 mmol) under an Ar atmosphere. After the reaction mixture was stirred in a preheated reaction block at 70° C. for 16 h, it was cooled to 25° C. The reaction mixture was treated with EtOAc (10 mL), and the precipitated solid was filtered by reduced pressure. The resulting residue was collected and under a vacuum. After drying, Dec-BTP$^+\cdot$Br$^-$ was obtained as a yellow solid (1.3 g, 70% yield). Dec-BTP$^+\cdot$Br$^-$ displayed identical $^1$H and $^{13}$C NMR spectra as Dec-B TP$^+$BE$_4^-$.

Example 14

Preparation of 4-(benzo[d]thiazol-2-yl)-1-decylpyridin-1-ium tetrafluoroborate (Dec-BTP$^+\cdot BF_4^-$)

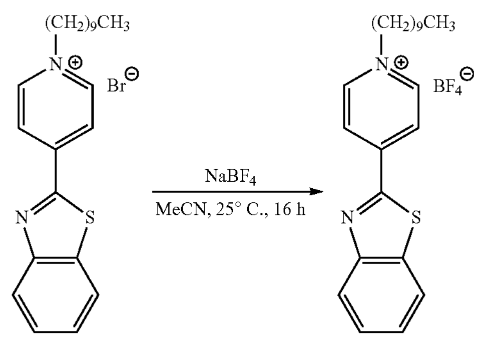

Dec-BTP$^+$•Br$^-$ Dec-BTP$^+$•BF$_4^-$

To a solution of 4-(benzo[d]thiazol-2-yl)-1-decylpyridin-1-ium bromide (Example 13, 1.3 g, 3.0 mmol) and MeCN (6.0 mL, 0.50 M) in a 40 mL-glass vial was added $NaBF_4$ (364 mg, 3.3 mmol). The reaction mixture was stirred at 25° C. for 16 h. The reaction mixture was treated with DI-water (10 mL), and the precipitated solid was filtered by reduced pressure.

The resulting residue was collected and dried under a vacuum. After drying, Dec-Dec-BTP$^+\cdot BF_4^-$ was obtained as a white solid (1.1 g, 81% yield).

mp 154-156° C.; IR (film) 3444, 2916, 1640, 1484, 1319, 1030 cm$^{-1}$; $^1$H NMR (400 MHz, DMSO-d$_6$) δ 9.27-9.18 (m, 2H), 8.79-8.69 (m, 2H), 8.38-8.29 (m, 1H), 8.27-8.19 (m, 1H), 7.73-7.60 (m, 2H), 4.67 (t, J=7.4 Hz, 2H), 2.02-1.88 (m, 2H), 1.35-1.27 (m, 4H), 1.27-1.15 (m, 10H), 0.89-0.78 (m, 3H); $^{13}$C NMR (100 MHz, DMSO-d$_6$) δ 161.4, 153.4, 146.2, 145.8, 136.2, 127.8, 127.7, 124.9, 124.3, 123.2, 60.7, 31.3, 30.8, 28.9, 28.8, 28.7, 28.4, 25.4, 22.1, 13.9; HRMS$^+$ (ESI) calcd. for $C_{22}H_{29}N_2S^+$ [M]$^+$ 353.2046, found 353.2049; HRMS$^-$ (ESI) calcd. for $BF_4^-$ [M]$^-$ 87.0035, found 87.0034.

Example 15

Preparation of 4-(benzo[d]thiazol-2-yl)-1-(2-methoxyethyl)pyridin-1-ium bromide (MOE-BTP$^+$·Br$^-$ )

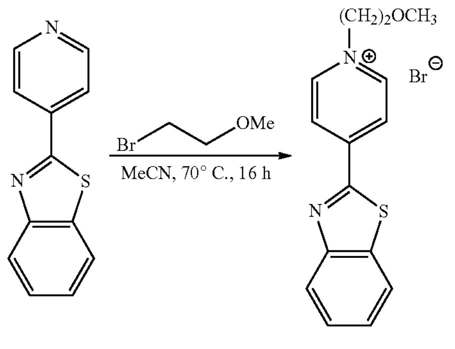

MOE-BTP$^+$•Br$^-$

To a solution of 2-(pyridin-4-yl)benzo[d]thiazole (Preparation Example 1, 1.0 g, 4.7 mmol) and MeCN (9.4 mL, 0.50 M) in a 40 mL-glass vial was added 2-bromoethyl methyl ether (786 mg, 5.7 mmol) under an Ar atmosphere. After the reaction mixture was stirred in a preheated reaction block at 70° C. for 16 h, it was cooled to 25° C. The reaction mixture was treated with EtOAc (10 mL), and the precipitated solid was filtered by reduced pressure. The resulting residue was collected and under a vacuum. After drying, MOE-BTP$^+$·Br$^-$ was obtained as a yellow solid (623 mg, 38% yield). MOE-BTP$^+$·Br$^-$ displayed identical $^1$H and $^{13}$C NMR spectra as MOE-BTP$^+$·$BF_4^-$.

Example 16

Preparation of 4-(benzo[d]thiazol-2-yl)-1-(2-methoxyethyl)pyridin-1-ium tetrafluoroborate (MOE-BTP$^+$·$BF_4^-$)

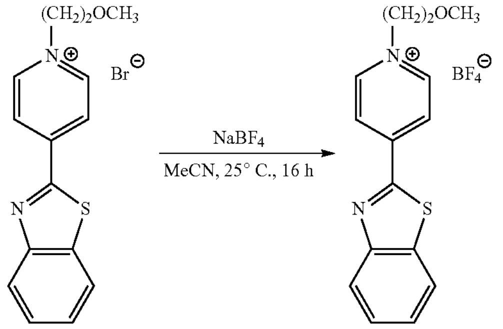

MOE-BTP$^+$•Br$^-$ MOE-BTP$^+$•$BF_4^-$

To a solution of 4-(benzo[d]thiazol-2-yl)-1-(2-methoxyethyl)pyridin-1-ium bromide (Example 15, 0.6 g, 1.8 mmol) and MeCN (3.6 mL, 0.50 M) in a 40 mL-glass vial was added $NaBF_4$ (214 mg, 2.0 mmol). The reaction mixture was stirred at 25° C. for 16 h. The reaction mixture was treated with DI-water (10 mL), and the precipitated solid was filtered by reduced pressure. The resulting residue was collected and dried under a vacuum. After drying, MOE-BTP$^+$·$BF_4^-$ was obtained as a white solid (323 mg, 51% yield).

mp 134-136° C.; IR (film) 3449, 2936, 1640, 1485, 1219, 1037 cm$^{-1}$; $^1$H NMR (400 MHz, DMSO-$d_6$) δ 9.23-9.16 (m, 2H), 8.77-8.71 (m, 2H), 8.37-8.30 (m, 1H), 8.26-8.20 (m, 1H), 7.71-7.58 (m, 2H), 4.91 (t, J=4.9 Hz, 2H), 3.88 (t, J=4.9 Hz, 2H), 3.29 (s, 3H); $^{13}$C NMR (100 MHz, DMSO-$d_6$) δ 161.3, 153.3, 146.5, 146.3, 136.2, 127.8, 127.7, 124.6, 124.3, 123.2, 70.1, 60.1, 58.3; HRMS$^+$ (ESI) calcd. for $C_{14}H_{15}N_2OS^+$ [M]$^+$ 271.0900, found 271.0904; HRMS$^-$ (ESI) calcd. for $BF_4^-$ [M]$^-$ $^{87.0035}$, found 87.0036.

Example 17

Preparation of 1,1'-(pentane-1,5-diyl)bis(4-(benzo[d]thiazol-2-yl)pyridin-1-ium) bromide (Di-BTP$^{2+}$·2Br$^-$)

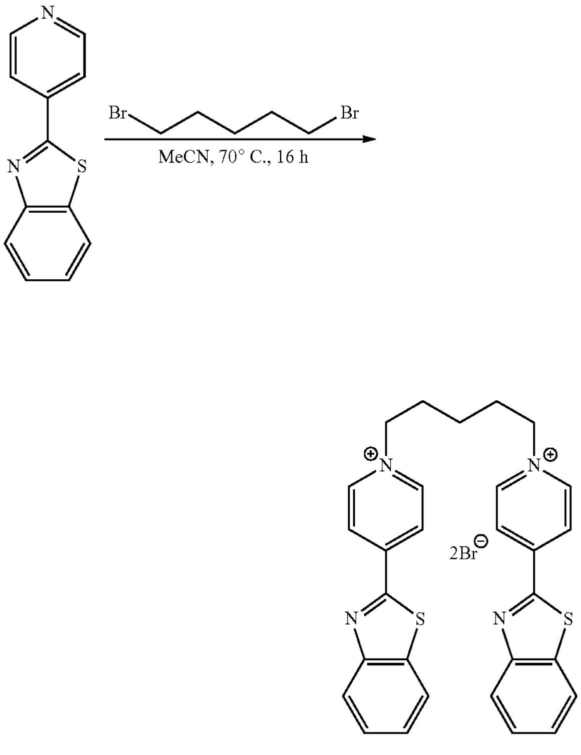

Di-BTP$^{2+}$•2Br$^-$

To a solution of 2-(pyridin-4-yl)benzo[d]thiazole (Preparation Example 1, 0.5 g, 2.4 mmol) and MeCN (4.8 mL, 0.50 M) in a 40 mL-glass vial was added 1,5-dibromopentane (271 mg, 1.2 mmol) under an Ar atmosphere. After the reaction mixture was stirred in a preheated reaction block at 70° C. for 16 h, it was cooled to 25° C. The reaction mixture was treated with EtOAc (10 mL), and the precipitated solid was filtered by reduced pressure. The resulting residue was collected and under a vacuum. After drying, Di-BTP$^{2+}$·2Br$^-$ was obtained as a yellow solid (567 mg, 73% yield). Di-BTP$^{Z+}$2Br$^-$ displayed identical $^1$H and $^{13}$C NMR spectra as Di-BTP$^{2+}$·$2PF_6^-$.

Example 18

Preparation of 1,1'-(pentane-1,5-diyl)bis(4-(benzo[d]thiazol-2-yl)pyridin-1-ium) hexafluorophosphate (Di-BTP$^{2+}$·2PF$_6^-$)

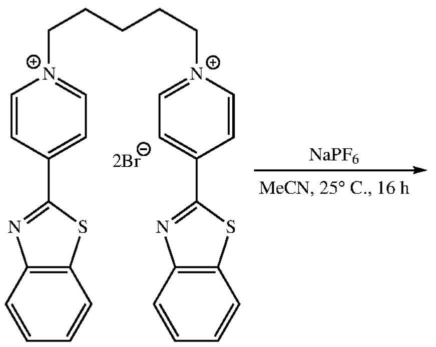

Di-BTP$^{2+}$•2Br$^-$

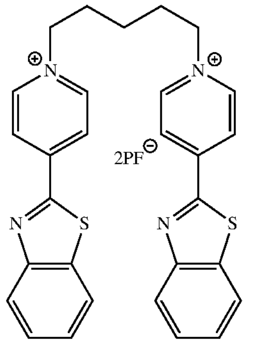

Di-BTP$^{2+}$•2PF$_6^-$

To a solution of 1,1'-(pentane-1,5-diyl)bis(4-(b enzo[d]thiazol-2-yl)pyridin-1-ium) bromide (Example 17, 567 mg, 0.9 mmol) and MeCN (1.8 mL, 0.50 M) in a 40 mL-glass vial was added NaPF$_6$ (320 mg, 1.9 mmol). The reaction mixture was stirred at 25° C. for 16 h. The reaction mixture was treated with DI-water (10 mL), and the precipitated solid was filtered by reduced pressure. The resulting residue was collected and dried under a vacuum. After drying, Di-BTP$^{2+}$·2PF$_6^-$ was obtained as a white solid (620 mg, 91% yield).

mp 270-272° C.; IR (film) 3390, 1638, 1483, 1168, 985, 834 cm"'; $^1$H NMR (400 MHz, DMSO-d$_6$) δ 9.25-9.19 (m, 4H), 8.83-8.77 (m, 4H), 8.37-8.32 (m, 2H), 8.28-8.23 (m, 2H), 7.74-7.63 (m, 4H), 4.68 (t, J=7.3 Hz, 4H), 2.07-1.98 (m, 4H), 1.41-1.32 (m, 2H); $^{13}$C NMR (100 MHz, DMSO-d$_6$) δ 161.3, 153.4, 146.3, 145.9, 136.2, 127.9, 127.8, 125.0, 124.3, 123.2, 60.2, 29.9, 21.8; HRMS$^+$ (ESI) calcd. for $C_{29}H_{26}N_4S_2^{2+}$ [M]$^{2+}$494.1588, found 494.1593; FIRMS" (ESI) calcd. for PF$_6^-$ [M]$^-$ 144.9647, found 144.9647.

[General Procedures for the Analysis]

Solubility Test

To prepare concentration calibration curves, a known amount of each redox-active molecule (TMAP-BTP$^{2+}$·2PF$_6^-$ (Example 5), TMAP-BTP$^{2+}$·2TFSI$^-$ (Example 6), BTP$^+$·BF$_4^-$ (Example 2), BTP$^+$·TFSI$^-$ (Example 3) and BTMAP-Fc·2TFSI$^-$ (Preparation Example 6)) was dissolved in a small amount of MeCN, following by dilution to be a total solution volume of 5 mL. 1 mL of this solution was injected to a vial, and a fresh aliquot of 1 mL MeCN was added to reduce the concentration to half. 1 mL of this solution was injected to a vial, and a fresh aliquot of 1 mL MeCN was added to reduce the concentration to half. This process was repeated a few times until UV-vis absorbance was below 1 arbitrary unit (a.u.). Calibration curves were drawn at λ=345 nm for TMAP-BTP$^{2+}$·2PF$_6^-$ (Example 5) and TMAP-BTP$^{2+}$·2TFSI$^-$ (Example 6), at λ=341 nm for BTP$^+$·BF$_4^-$ (Example 2) and BTP$^+$·TFSI$^-$ (Example 3), and at λ=435 nm for BTMAP-Fc 2TF (Preparation Example 6).

To measure the maximum solubility, each chemical was added to 0.5 mL of MeCN or electrolyte solution until supersaturation at ambient condition. The electrolyte solution indicates 0.5 M TBA$^+$and anion in MeCN, where the anion is the same as that of the sample. After filtration, 20 μL of the solution was diluted using fresh MeCN and adjust the UV-vis absorbance to below one a.u. The maximum solubility was estimated by using the calibration curves.

Electrochemical Characterizations

All electrochemical examinations were carried out using a Biologic VMP3 electrochemical workstation in an Ar-filled glove box (MOTek, negligible O$_2$ and H$_2$O, tested by the ketyl solution).

Cyclic voltammetry (CV) was conducted in three-electrode cells comprised of glassy carbon (GC; diameter (d)=3 mm) as the working electrode (WE), a platinum wire as the counter electrode (CE), and a leak-free Ag/AgCl as the reference electrode (RE). The GC electrodes were polished using alumina slurry before testing (ALS Co., Ltd).

After CV analysis, ferrocene (Fc, ferrocene, 98%, Sigma-Aldrich) was added to the cell to measure its redox potential, and the measured sample potential was converted to the Fc/Fc$^+$.

To measure diffusion coefficient (D), rotating disk electrode (RDE; ALS Co., Ltd) measurements were conducted with the same three-electrode cells. Linear sweep voltammetry (LSV) was achieved at 50 mV s$^{-1}$ through electrode rotating from 400 rpm to 2025 rpm. Limited mass-transport provides a current plateau ($i_L$) of redox processes, which is linearly proportional to the square root of the rotating rates ($\omega^{1/2}$). The diffusion coefficient (D) was calculated by plotting IL as a function of $\omega^{1/2}$ and through the Levich equation (equation S1).

$$i_L=0.620nFAD^{2/3}\omega^{1/2}\eta^{-1/6}C_o \quad \text{(equation S1)}$$

where $I_L$ is the limiting current (A cm$^{-2}$), n is the number of electrons transferred during the redox reaction, F is the Faraday's constant (96485 C mol$^{-1}$), A is the area of the electrode (0.0707 cm$^2$), D is the diffusion coefficient (cm$^2$ s$^{p31\ 1}$), ω is the angular rotation rate (rad s$^{-1}$), η is the kinematic viscosity (0.00442 cm$^2$ s$^{-1}$, referred to 0.1 M TBAPF$_6$/MeCN), and $C_o$ is the concentration of the sample chemical.

The electron-transfer rate ($k^0$) was calculated from CV curves and using the Nicholson method(equation S2).

$$\Psi = k^o\left(\frac{\pi DnF}{RT}\right)^{-1/2} v^{-1/2} \quad \text{(equation S2)}$$

where $k^o$ is the electron-transfer constant (cm/s), D is the diffusion coefficient estimated from the above RDE studies, R is the gas constant (8.314 J K$^{-1}$ mol$^{-1}$), T is the temperature (298 K), v is the scan rate of the CVs (mV s$^{-1}$).

The Ψ value was obtained by Kingler and Kochi relation (equation S3).

$$\Psi = \left(\frac{-0.6288 + 0.0021\Delta E_p}{1 - 0.017\Delta E_p}\right) \quad \text{(equation S3)}$$

where $\Delta E_p$ is the peak-to-peak potential for the corresponding reduction or oxidation event.

Permeability Tests

Permeability tests were performed by referring to the literature [*Adv. Energy* Mater. 2020, 10, 2000100.]. Permeability tests of TMAP-$BTP^{2+}$, TMAP-$BTP^{\cdot+}$, $BTP^{+}$, or $BTP^{\cdot}$ were conducted using an H-cell installed with anion exchange membrane (AEM; FAPQ-275-PET, Fumasep) and analyzed by UV-Vis spectrometry.

For permeability of TMAP-$BTP^{2+}$, a 6 mL solution of 0.05 M TMAP-$BTP^{2+}$ in 0.5 M TBATFSI/MeCN was added to the one side (donating part), and a 6 mL of 0.575 M TBATFSI/MeCN electrolyte solution was added to the other side (receiving part). For permeability of $BTP^{+}$, a 6 mL solution of 0.05 M $BTP^{+}$ in 0.5 M TBATFSI/MeCN was added to the donating part, and a 6 mL of 0.55 M TBATFSI/MeCN electrolyte solution was added to the receiving part.

In order to prepare TMAP-$BT^{\cdot+}$ or $BTP^{\cdot}$ from TMAP-$BTP^{2+}$ or $BTP^{+}$, a full redox flow battery (full RFB) including 15 mL of a solution including 0.05 M TMAP-$BTP^{2+}$ $\cdot 2TFSI^{-}$ in 0.5 M TBATFSI/MeCN and 15 mL of a solution including 0.05 M $BTP^{+}\cdot TFSI^{-}$ in 0.5 M TBATFSI/MeCN, respectively as a negolyte solution, and 10 mL of 0.1 M BTMAP-Fc$\cdot 2TFSI^{-}$ as a posolyte solution was installed. An anion exchange membrane (AEM; FAPQ-275-PET, Fumasep) was used as a separator. The installed full RFB was slowly charged at a current density of 2 $mA/cm^2$ and a flow velocity of 60 mL/min. A cutoff potential was 1.5 V. It was assumed that the battery was fully charged in a $1^{st}$ charging process and there was no crossover of each species. After terminating the $1^{st}$ charging process, the resulting TMAP-$BTP^{\cdot+}$ or $BTP^{\cdot}$ electrolyte solution was extracted from the negolyte, followed by adding a 6 mL solution to the donating part, and a 6 mL of 0.55 M or 0.525 M TBATFSI/MeCN electrolyte solution was added to the receiving part.

The concentration of TBATFSI in the electrolyte solution parts was designed to rule out the osmotic effects. The osmotic pressure was calculated through the following equation (equation S4).

$$\pi=(i_aC_a+i_sC_s)RT \quad \text{(equation S4)}$$

where H is the osmotic pressure (atm), a is the active materials, s is the salt, i is the van't Hoff's factor (TMAP-$BTP^{2+}\cdot 2TFSI^{-}$: 3, TMAP-$BTP^{\cdot+}\cdot TFSI^{-}$ or $BTP^{+}\cdot TFSI^{-}$: 2, $BTP^{\cdot}$: 1, and TBATFSI: 2), C is the concentration (mol $L^{-1}$), R is the gas constant (0.08206 L atm $mol^{-1}$ $K^{-1}$), and Tis the temperature (298 K).

Each side was stirred, and the crossover of TMAP-$BTP^{2+}$, TMAP-$BTP^{\cdot+}$, $BTP^{+}$ or $BTP^{\cdot}$ was analyzed by taking 0.5 mL of the electrolyte solution in the receiving part, which was then diluted until UV-Vis absorbance reached below 1 a.u. The fresh electrolyte solution (0.5 mL) was filled in the receiving part for continuous testing.

The permeability was calculated by Fick's law (equation S5).

$$P=\frac{\Delta\ln\left(1-\frac{2C_r}{C_0}\right)\left(\frac{V_0L}{2A}\right)}{\Delta t} \quad \text{(equation S5)}$$

where P is the permeability ($cm^2$ $s^{-1}$), $C_r$ is the concentration of TMAP-$BTP^{2+}$, TMAP-$BTP^{\cdot+}$, $BTP^{+}$, or $BTP^{\cdot}$ in the receiving side at time t, $C_0$ is the initial concentration of TMAP-$BTP^{2+}$, TMAP-$BTP^{\cdot+}$, $BTP^{+}$, or $BTP^{\cdot}$ (0.05 M) in the donating side, $V_0$ is the initial volume (6 mL), L is the thickness of the membrane (75 μm), A is the area of the membrane (0.2827 $cm^{-2}$), and t is the time (s).

Redox Flow Battery (RFB) Tests

Preparation of carbon felt electrode: Carbon felt (CF, thickness (t)=3 mm, $XF_{30}A$, Toyobo) was immersed in deionized (DI) water and sonicated for 1 h. Subsequently, the CF was sonicated for 1 h in acetone and dried under vacuum at 80° C. for 24 h.

Preparation of anion exchange membrane (AEM): The AEM (FAPQ-275-PET, t=75 μm, counter ion: $Cl^{-}$/$MeOSO_3^{-}$, fumasep) was immersed in 1 M TBATFSI/MeCN for 1 day to replace the anions to TFSI".

Preparation of unbalanced compositionally symmetric electrolyte solutions: Reference was made to the literature [*ACS Energy Lett.* 2019, 4, 2220-2240]. TMAP-$BTP^{\cdot+}$ was used in both a negolyte solution and a posolyte solution for a symmetric redox flow battery (RFB). To prepare TMAP-$BTP^{\cdot+}$ from the as-prepared TMAP-$BTP^{2+}$, a full RFB was installed including 13 mL of 0.1 M TMAP-$BTP^{2+}\cdot 2TFSI^{-}$ with 0.5 M TBATFSI/MeCN as the negolyte and 13 mL of 0.12 M of BTMAP-Fc$\cdot 2TFSI^{-}$ as the posolyte. AEM (FAPQ-275-PET) was used as the separator. The full RFB was slowly charged at a current density of 3 mA $cm^{-2}$ and a flowing rate of 60 mL $min^{-2}$. The cutoff potential was 1.5 V. After terminating the $1^{st}$ charging process, the resulting TMAP-$BTP^{\cdot+}$ electrolyte solution was extracted from the negolyte, followed by mixing with 13 mL of 0.1 M original TMAP-$BTP^{2+}$ solution. This mixture of TMAP-$BTP^{2+}$ and TMAP-$BTP^{\cdot+}$ was used in both the negolyte and posolyte in the symmetric RFB tests. Afterward, the symmetric RFB was installed with 10 mL of the mixture as the negolyte, 16 mL of the mixture as the posolyte, and the AEM.

Preparation of Electrolyte Solutions for Full RFBs:

1. 0.1 M full cells: 10 mL of a negolyte solution including 0.1 M TMAP-$BTP^{Z+}\cdot 2TFSI^{-}$ or $BTP^{+}\cdot TFSI^{-}$ in 0.5 M TBATFSI/MeCN and 10 mL of a posolyte solution including 0.15 M BTMAP-Fc2TFSI$^{-}$ in 0.5 M TBATFSI/MeCN were separately prepared. Both solutions in customized containers were purged with Ar gas for 10 min before sealing.

2. 0.2 M full cells: 10 mL of a negolyte solution including 0.2 M TMAP-$BTP^{2+}\cdot 2TFSI^{-}$ in 0.5 M TBATFSI/MeCN and 15 mL of a posolyte solution including 0.2 M BTMAP-Fc$\cdot 2TFSI^{-}$ in 0.5 M TBATFSI/MeCN were separately prepared. Both solutions in customized containers were purged with Ar gas for 10 min before sealing.

3. 0.3 M full cells: 10 mL of a negolyte solution including 0.3 M TMAP-$BTP^{2+}\cdot 2TFSI^{-}$ in 0.5 M TBATFSI/MeCN and 15 mL of a posolyte solution including 0.3 M BTMAP-Fc$\cdot 2TFSI^{-}$ in 0.5 M TBATFSI/MeCN were separately prepared. Both solutions in customized containers were purged with Ar gas for 10 min before sealing.

Preparation of mixed solution of negolyte solution and posolyte solution for symmetric RFB: 0.025 M $TP^{+}\cdot TFSI^{-}$ was simply mixed with 0.025 M BTMAP-Fc$\cdot 2TFSI^{-}$ in 0.1 M TBATFSI/MeCN. Similarly, 0.025 M TMAP-$BTP^{2+}$ $\cdot 2TFSI^{-}$ or $BTP^{+}\cdot TFSI^{-}$ was mixed with 0.025 M BTMAP-Fc$\cdot 2TFS1^{-}$ in 0.1 M TBATFSI/MeCN for control experiment. 10 mL of the solution was used for each side electrolyte solution. Before the cell assembly, all solutions were purged with Ar gas for 10 min.

Figure 16:
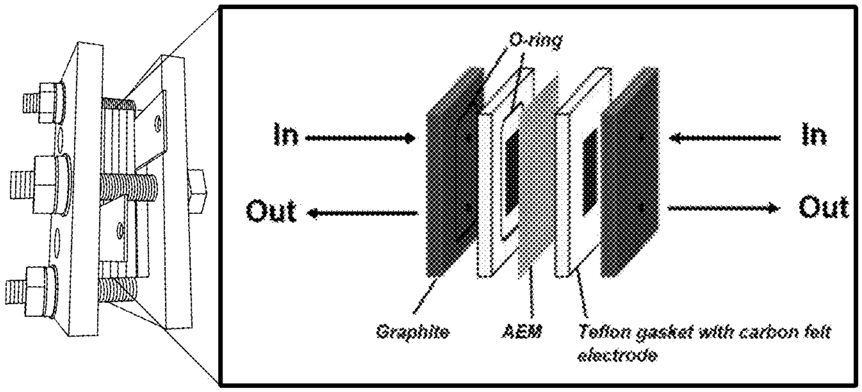
FIG. 16—Digital image and configuration of RFB.

Assembly of zero-gap RFB: The RFBs were purchased from the ES group (Republic of Korea). The prepared CF electrode was installed to Teflon gasket (surface area of CF=6 $cm^2$). The cell was assembled with graphite flow plates having a non-flow field pattern and the CF with Teflon gasket for both negative and positive electrode side, which were sandwiched with the pre-treated AEM as depicted in FIG. 16. Perfluoro elastomer O-ring (HYUNJIN PS, Republic of Korea) was used in the graphite flow plates for complete sealing of the non-aqueous RFB. Peristaltic pump (Masterflex® L/S® Standard Digital Pump, Cole-Parmer, USA) with norprene tubing (Cole-Parmer, USA) was used for circulating electrolyte solutions from both containers.

Galvanostatic examinations of RFB: Before tests, electrolyte solutions were circulated over 12 h for wetting of CF electrodes. The applied current densities were various, while a flowing rate was constantly held to 60 mL $min^{-1}$. A volumetric capacity was calculated through the following equation (equation S6):

$$\text{Theoretical capacity } (Q_{th}) = nFMV \quad \text{(equation S6)}$$

where n is the number of electrons, F is the Faraday's constant (26.8 Ah), M is the concentration of the redox molecule (mol $L^1$), and V is the volume of the negolyte (L). For 10 mL of 0.1 M TMAP-$BTP^{2+}$·2$TFSI^-$ negolyte, the theoretical Qth is estimated to 0.0268 Ah (volumetric theoretical capacity=2.68 Ah $L^{-1}$).

Coulombic efficiency (CE), voltage efficiency (VE), Energy efficiency (EE) of RFB were calculated through the following equation (equation S7-S9):

$$\text{Coulombic efficiency } (CE) = \frac{Q_{dc}}{Q_{cc}} \quad \text{(equation S7)}$$

where $Q_{dc}$ is the discharge capacity, and $Q_{cc}$ is the charge capacity.

$$\text{Voltage efficiency } (VE) = \frac{V_{dc}}{V_{cc}} \quad \text{(equation S8)}$$

where $V_{dc}$ is the discharge voltage, and $V_{cc}$ is the charge voltage.

$$\text{Energy efficiency } (EE) = \frac{E_{dc}}{E_{cc}} = CE \times VE \quad \text{(equation S9)}$$

where $E_{dc}$ is the discharge energy density, and $E_{cc}$ is the charge energy density.

Capacity-fading rate per cycle of TMAP-$BTP^{2+}$ or $BTP^+$ RFB was calculated through the following equation (equation S10):

$$Q_{fadpercycle} = \left(1 - e^{\frac{ln\left(\frac{Q_{final}}{Q_{initial}}\right)}{n-1}}\right) \times 100 \quad \text{(equation S10)}$$

where $Q_{fad\ per\ cycle}$ is the capacity-fading rate per cycle, $Q_{final}$ is the cell capacity at final cycle, $Q_{initial}$ is the cell capacity at initial cycle, and n is the number of cycles.

Area Specific Resistance (ASR), Polarization, and Power Density

Full RFBs with TMAP-$BTP^{2+}$ and BTMAP-Fc were electrochemically charged with a different state of charges (SOCs) to measure open-circuit voltage (OCV) and polarization. At the desired SOC, electrochemical impedance spectroscopy (EIS) was measured at OCV with a dc voltage of 10 mV and a frequency ranging from 1 to 100,000 Hz. The impedance at the high-frequency region (imaginary impedance=0) indicates the area-specific resistance (ASR) of the AEM in the given 6 $cm^2$ area. In addition, LSV was measured at 100 mV $s^{-1}$ for polarization. The proximity of polarization ASR was calculated from linear slopes of polarization curves in a voltage range of 0.9-1.1 V. Power density was estimated by multiplying potential and current density in the polarization curves.

Post-Mortem CV and $^1$H NMR Analyses

After galvanostatic cycling, 2 mL of negolyte- and posolyte-side electrolyte solutions from the container were separately extracted. Afterward, a CV diagnosis was performed in the aforementioned three-electrode cells to investigate the crossover of the negolyte.

$^1$H NMR was also analyzed for both negolyte- and posolyte-side electrolyte solutions. After drying the electrolyte solutions under the vacuum, the resulting solid powder was dissolved in 0.5 mL of $CD_3CN$ to take $^1$H NMR.

[Results]

Results of measuring solubility of various pyridinium compounds in acetonitrile are shown in the following Tables 1 and 2.

In the case of pyridinium compounds including a $BF_4^-$ or $PF_6^-$ counter anion, introduction of a hydrophilic group such as methyl, hexyl, decyl, or methoxyethyl, and oligomerization showed a solubility of 0.07 to 0.26 M in MeCN. However, TMAP-$BTP^{2+}$ including a cationic TMAP group provided a high solubility comparable to BTP+ including a $BF_4^-$ or $PF_6^-$ counter anion. In addition, by changing the counter anion from $BF_4^-$ or $PF_6^-$ to $TFSI^-$, the solubility of the pyridinium compound in MeCN was significantly increased up to ~1.0 M.

Figure 2:
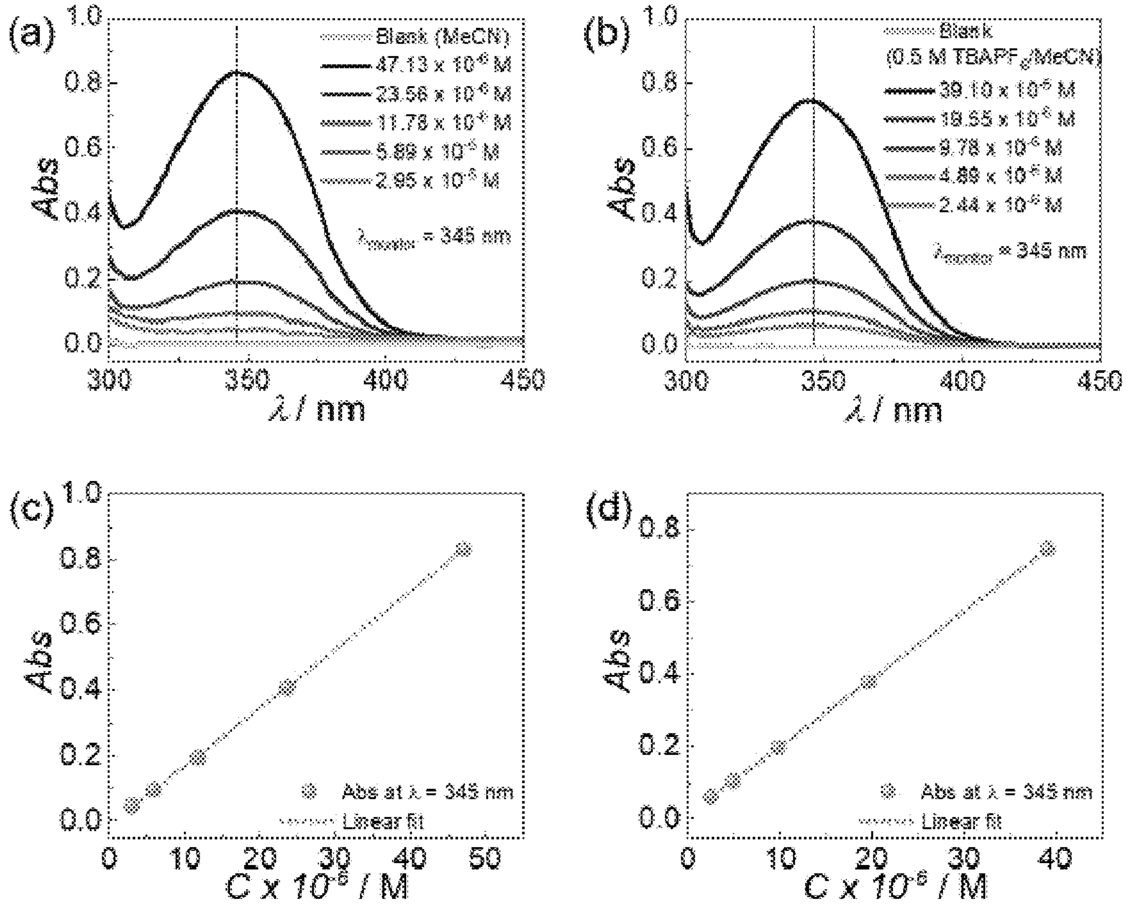
FIG. 2—UV-Vis spectra of TMAP-$BTP^{2+}\cdot 2PF_6^-$ with different concentrations in (a) MeCN and (b) electrolyte solution (0.5 M $TBAPF_6$/MeCN). Corresponding calibration curves of TMAP-$BTP^{2+}\cdot 2PF_6^-$ in (c) MeCN and (d) the electrolyte solution. The maximum solubility of TMAP-$BTP^{2+}\cdot 2PF_6^-$ is 0.25 M and 0.026 M in MeCN and electrolyte solution, respectively.
Figure 3:
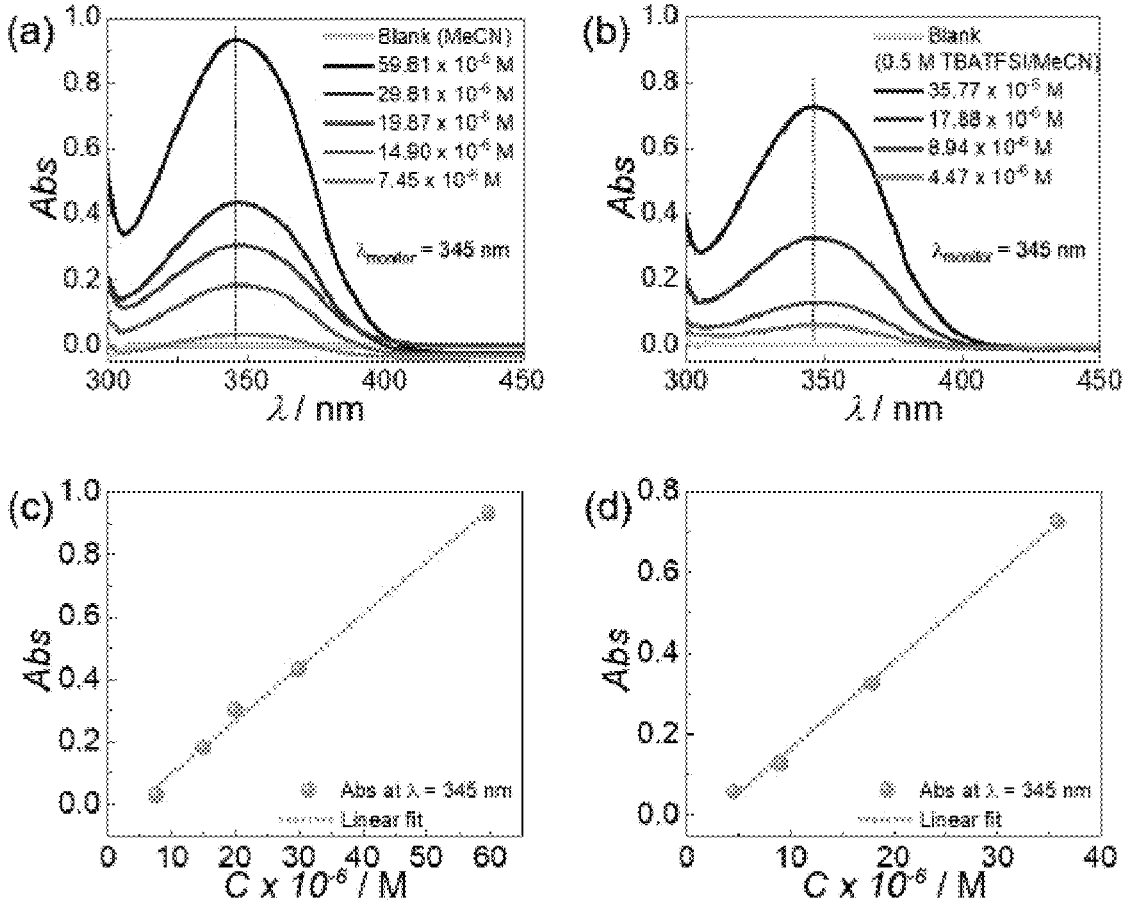
FIG. 3—UV-Vis spectra of TMAP-$BTP^{2+}\cdot 2TFSI^-$ with different concentrations in (a) MeCN and (b) electrolyte solution (0.5 M TBATFSI/MeCN). Corresponding calibration curves of TMAP-$BTP^{2+}\cdot 2TFSI^-$ in (c) MeCN and (d) the electrolyte solution. The maximum solubility of TMAP-$BTP^{2+}\cdot 2TFSI^-$ is 0.89 M and 0.34 M in MeCN and the electrolyte solution, respectively.
Figure 4:
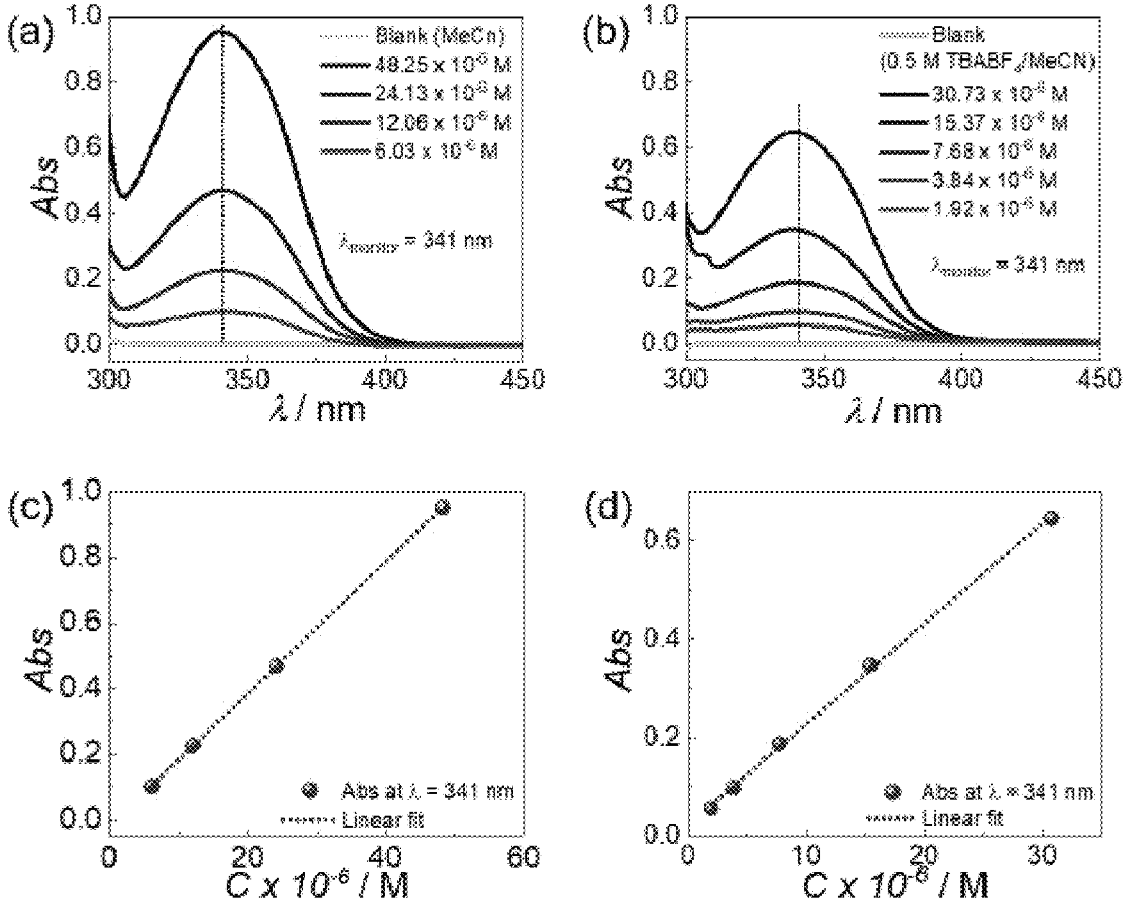
FIG. 4—UV-Vis spectra of $BTP^+\cdot BF_4^-$ with different concentrations in (a) MeCN and (b) electrolyte solution (0.5 M TBABF4/MeCN). Corresponding calibration curves of $BTP^+\cdot BF_4^-$ in (c) MeCN and (d) the electrolyte solution. The maximum solubility of $BTP^+\cdot BF_4^-$ is 0.26 M and 0.087 M in MeCN and the electrolyte solution, respectively.
Figure 5:
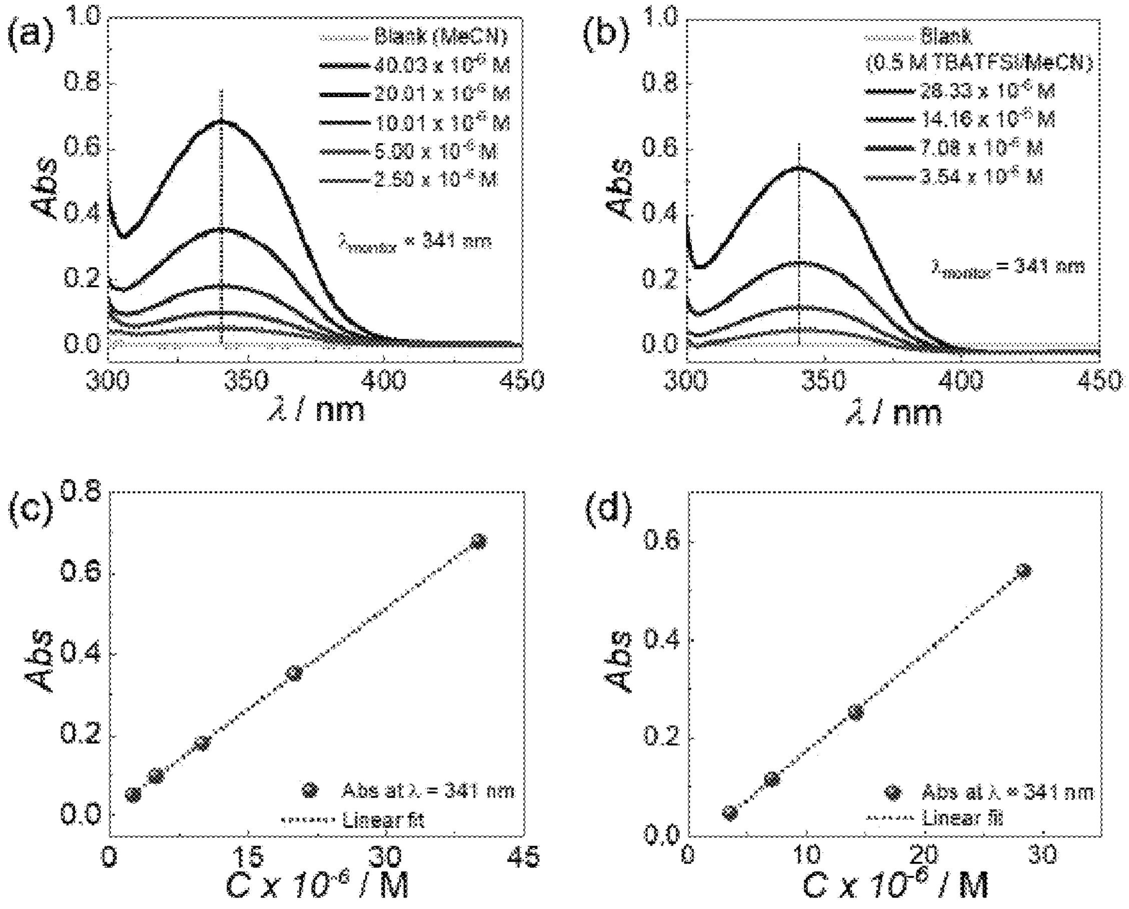
FIG. 5—UV-Vis spectra of $BTP^+\cdot TFSI^-$ with different concentrations in (a) MeCN and (b) electrolyte solution (0.5 M TBATFSI/MeCN). Corresponding calibration curves of $BTP^+\cdot TFSI^-$ in (c) MeCN and (d) the electrolyte solution. The maximum solubility of $BTP^+\cdot TFSI^-$ is 1.0 M and 0.47 M in MeCN and the electrolyte solution, respectively.

In addition, when the corresponding $BF_4^-$, $PF_6^-$, and $TFSI^-$ salts were provided by anion exchange, it was confirmed that the solubility of the pyridinium compound was significantly increased (Table 2). In particular, when a counter anion was $PF_6^-$, the solubility of TMAP-$BTP^{2+}$was 0.25 M in MeCN and 0.026 M in a 0.5 M $TBAPF_6$/MeCN electrolyte solution (FIG. 2), but when a counter anion was $TFSI^-$, the solubility was significantly improved to a maximum of 0.89 M in MeCN and 0.34 M in 0.5 M TBATFSI/MeCN (FIG. 3). Similarly, the solubility of $BTP^+$ was also significantly improved to 1.00 M and 0.5 M in MeCN and 0.47 M in TBATFSI/MeCN, by changing $BF_4^-$ to $TFSI^-$ (Table 2, FIGS. 4 and 5).

That is, it is recognized that the pyridinium compound according to the present disclosure may substantially increase the solubility without a structural change of a redox-active core by anion exchange.

TABLE 1]

Solubility (M) of pyridinium compounds in MeCN

| Pyridinium compound | Solubility (M) in MeCN |
|---|---|
| $BTP^+$•$BF_4^-$ (Example 2) | 0.26 |
| $BTP^+$• $FSI^-$ (Example 3) | 1.00 |
| TMAP-$BTP^{2+}$•2$PF_6^-$ (Example 5) | 0.25 |
| TMAP-$BTP^{2+}$•2$TFSI^-$ (Example 6) | 0.89 |
| Hex-$BTP^+$•$BF_4^-$ (Example 12) | 0.23 |
| Dec-$BTP^+$•$BF_4^-$ (Example 14) | 0.07 |
| MOE-$BTP^+$•$BF_4^-$ (Example 16) | 0.10 |
| Di-$BTP^{2+}$•2$PF_6^-$ (Example 18) | 0.10 |

TABLE 2]

Solubility (M) of pyridinium compound of $BTP^+$ and TMAP-$BTP^{2+}$ for counter anion in MeCN and electrolyte solution

| | Pyridinium compound | Solubility (M) MeCN | Solubility (M) 0.5M $TBAPF_6$/ MeCN |
|---|---|---|---|
| $BTP^+$ | $BTP^+$•$BF_4^-$ (Example 2) | 0.26 | 0.087 |
| | $BTP^+$•$TFSI^-$ (Example 3) | 1.00 | 0.47 |
| TMAP-$BTP^{2+}$ | TMAP-$BTP^{2+}$•2$PF_6^-$ (Example 5) | 0.25 | 0.026 |
| | TMAP-$BTP^{2+}$•2$TFSI^-$ (Example 6) | 0.89 | 0.34 |

Figure 6:
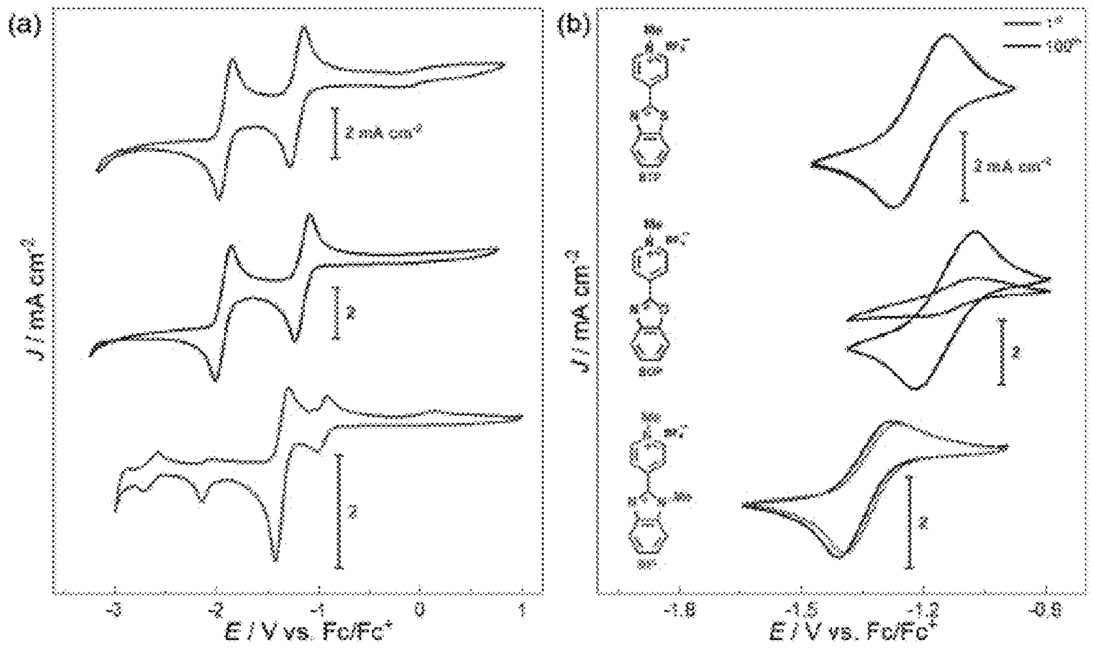
FIG. 6—CVs of 10 mM $BTP^+\cdot BF_4^-$ (green, top), $BOP^+$ $\cdot$BF4$^-$ (blue, middle), and $BIP^+\cdot BF_4^-$ (red, bottom) in 0.1 M TBABF4/MeCN at a scan rate of 50 mV $s^{-1}$. (a) Wide CV scan and (b) the 1st (black) and the 100th cycles for the 1 electron-transfer process.
Figure 7:
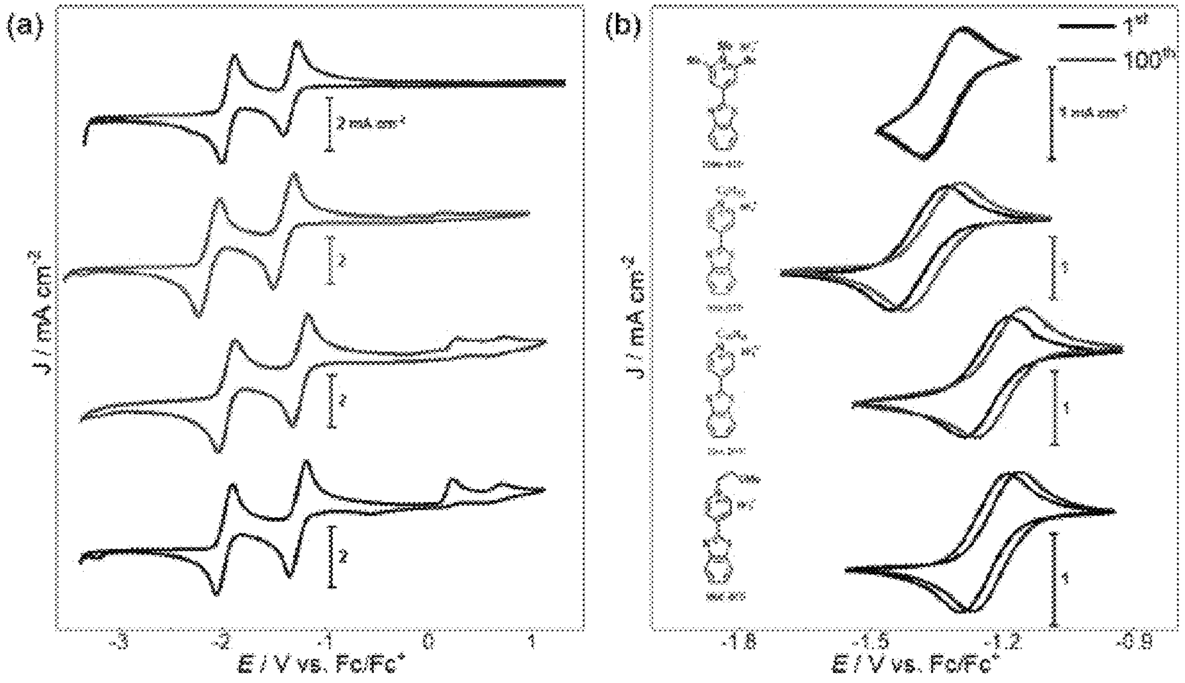
FIG. 7—CVs of 10 mM DiMe-$BTP^+\cdot BF_4^-$ (brown, top), Hex-$BTP^+\cdot BF_4^-$ (pink, upper middle), Dec-$BTP^+\cdot BF_4^-$ (purple, lower middle), and MOE-$BTP^+\cdot BF_4^-$ (dark blue, lower) in 0.1 M TBABF4/MeCN. (a) Wide CV scan at a scan rate of 50 mV $s^{-1}$. (b) The $1^{st}$ (black) and the $100^{th}$ cycles for the 1 electron-transfer process at a scan rate of 10 mV $s^{-1}$.

In addition, electrochemical properties for various pyridinium compounds prepared in the examples were confirmed (Table 3, FIG. 6, and FIG. 7). The electrochemical stability of $BTP^+$ during one electron and two electron-transfer processes was better than that of a benzoxazole-containing counterpart, that is, $BOP^+$ and a benzimidazole-containing counterpart, that is, $BIP^+$ in a cyclic voltammetry (CV) test (FIG. 6 and Table 3). Both $BTP^+$ and DiMe-$BTP^+$ showed excellent cyclability in the CV profile (FIGS. 6 and 7). Sufficient stability of $BTP^+$ itself was confirmed therefrom. In addition, Hex-BTP, Dec-BTP and MOE-BTP showed positive (+) potential shift after CV cycles (FIG. 7).

TABLE 3

[][]Electrochemical properties of pyridinium compound.
Values in parentheses are those obtained after 100 cycles.

| | Electrochemical characteristics | | |
|---|---|---|---|
| | Formal potential ($E^{o'}$) (V vs. $Fc/Fc^+$) | Ratio of anodic peak current ($I_{pa}$) to cathodic peak current ($I_{pc}$) ($I_{pa}/I_{pc}$) @50 mV $s^{-1}$ | Peak to peak potential difference ($\Delta E_p$) (mV) |
| $BOP^+\bullet BF_4^-$ (Example 7) | $1^{st}$ = −1.15<br>$2^{nd}$ = n.d. | $1^{st}$ = 0.79 (0.46)<br>$2^{nd}$ = n.d. | $1^{st}$ = 105 (105)<br>$2^{nd}$ = n.d. |
| $BIP^+\bullet BF_4^-$ (Example 8) | −1.41 | 0.71 (0.73) | 99 (99) |
| DiMe-$BTP^+\bullet BF_4^-$ (Example 10) | $1^{st}$ = −1.33<br>$2^{nd}$ = −1.94 | $1^{st}$ = 0.89 (0.88)<br>$2^{nd}$ = n.d. | $1^{st}$ = 89 (81)<br>$2^{nd}$ = n.d. |
| Hex-$BTP^+\bullet BF_4^-$ (Example 12) | $1^{st}$ = −1.36<br>$2^{nd}$ = −2.13 | $1^{st}$ = 0.98 (0.99)<br>$2^{nd}$ = n.d. | $1^{st}$ = 125 (124)<br>$2^{nd}$ = n.d. |
| Dec-$BTP^+\bullet BF_4^-$ (Example 14) | $1^{st}$ = −1.24<br>$2^{nd}$ = −1.96 | $1^{st}$ = 0.93 (0.91)<br>$2^{nd}$ = n.d. | $1^{st}$ = 99 (102)<br>$2^{nd}$ = n.d. |
| MOE-$BTP^+\bullet BF_4^-$ (Example 16) | $1^{st}$ = −1.24<br>$2^{nd}$ = −1.97 | $1^{st}$ = 1.00 (0.98)<br>$2^{nd}$ = n.d. | $1^{st}$ = 104 (107)<br>$2^{nd}$ = n.d. |

The electrochemical properties of TMAP-$BTP^{2+}$, $BTP^+$, and BTMAP-Fc were confirmed (Table 4).

TABLE 4

Electrochemical properties of TMAP-$BTP^{2+}$, $BTP^+$, and BTMAP-Fc
Values in parentheses are those obtained after 100 cycles.

| | Solubility | | Electrochemical characteristics | | | | |
|---|---|---|---|---|---|---|---|
| | MeCN (M) | 0.5M TBATFSI/MeCN (M) | $E^{o'}$ (V vs. $Fc/Fc^+$) | $I_{pa}/I_{pc}$ @50 mV $s^{-1}$ | $\Delta E_p$ (mV) | D (X$10^{-6}$ $cm^2$ $s^{-1}$) | $k^o$ (cm $s^{-1}$) |
| TMAP-$BTP^{2+}\cdot 2TFSI^-$ (Example 6) | 0.89 | 0.34 | $1^{st}$ = −1.19<br>$2^{nd}$ = −1.87 | $1^{st}$ = 0.97 (0.97)<br>$2^{nd}$ = 1.08 (1.18) | $1^{st}$ = 105 (105)<br>$2^{nd}$ = 94 (85) | $c_1$ = 1.91<br>$c_2$ = 1.91 | $c_1$ = 0.114<br>$c_2$ = 0.124 |
| $BTP^+\cdot TFSI^-$ (Example 3) | 1.00 | 0.47 | $1^{st}$ = −1.21<br>$2^{nd}$ = −1.90 | $1^{st}$ = 1.01 (0.99)<br>$2^{nd}$ = 0.95 (0.87) | $1^{st}$ = 99 (99)<br>$2^{nd}$ = 93 (84) | $c_1$ = 3.71<br>$c_2$ = 3.32 | $c_1$ = 0.086<br>$c_2$ = 0.090 |
| BTMAP-$Fc\cdot 2TFSI^-$ | 2.0 | 1.6 | −0.03 | 1.03 (1.03) | 149 (149) | 2.00 | 0.034 |

Electrochemical characterizations of the TMAP-$BTP^-$ were investigated using CV in the three-electrode cells. The CV curve of TMAP-$BTP^-$ demonstrated two redox waves at the formal potentials ($E^{o'}$)) of −1.19 V and −1.87 V vs. $Fc/Fc^+$ and indicated diffusion-limited processes (Table 4, (a)-(b) of FIG. 8). The presence of a benzothiazole ring in the pyridinium compound stabilized a redox-active pyridinium core during a first electron-transfer process. Although the second electron-transfer process possibly occurred via the delocalization of electron density to the benzothiazole ring (FIG. 9), the CV curve revealed unstable profiles for 100 cycles ((a) of FIG. 8). Each of first and second reduction/oxidation events was indicated as redox peak-current $c_1/a_1$ and $c_2/a_2$, but only the stable first electron-transfer process was focused. The diffusion coefficient (D) and electron-transfer constant ($k^o$) of TMAP-$BTP^{2+}$ were $1.91\times10^{-6}$ $cm^2$ $s^{-1}$ and ~0.1 cm $s^{-1}$, respectively ((b) and (d) of FIG. 8).

Figure 8:
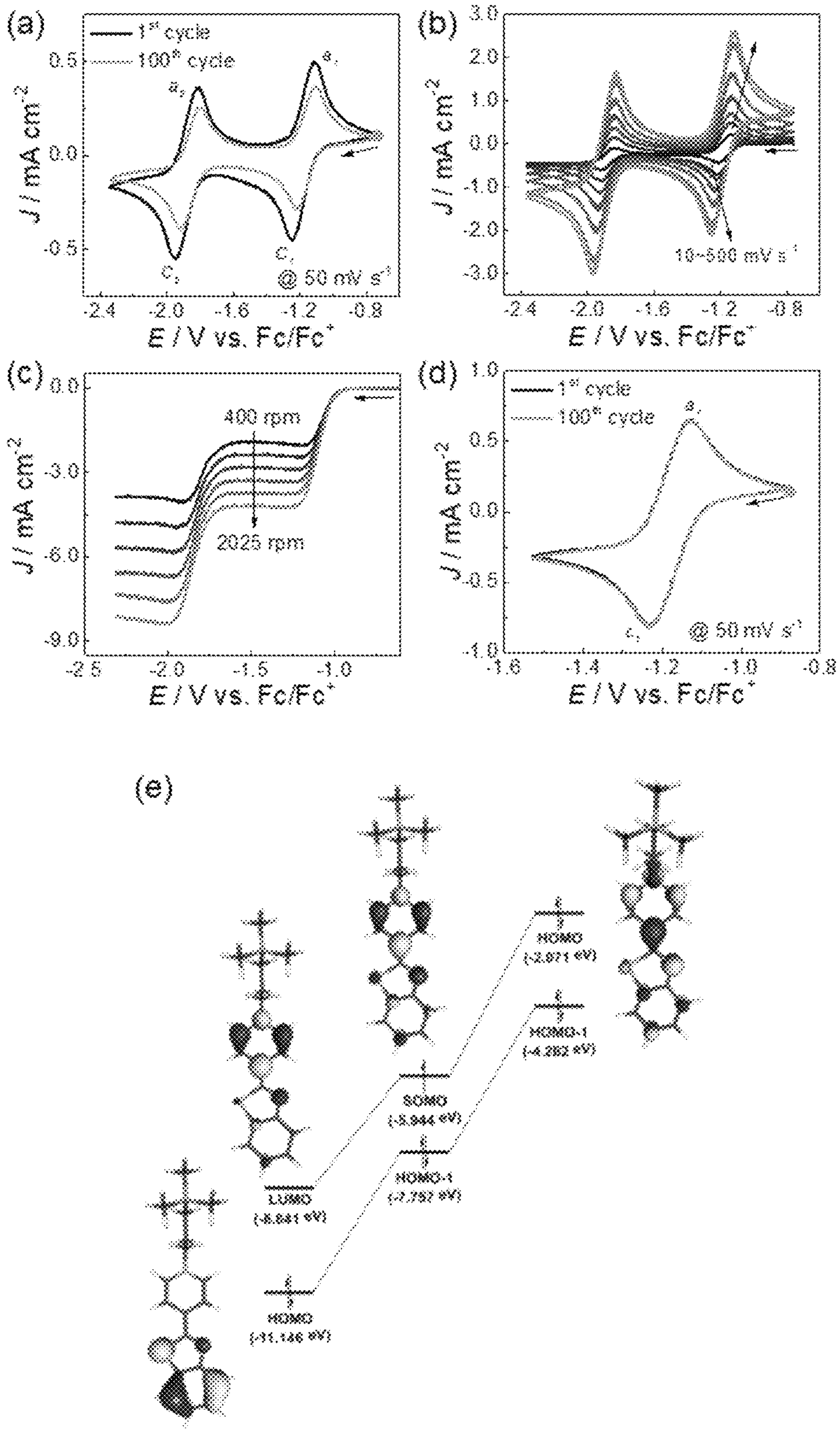
FIG. 8—Electrochemical characteristics of 4 mM TMAP-$BTP^{2+}\cdot 2TFSI^-$ in 0.1 M TBATFSI/MeCN electrolyte solution. (a) CV curves of TMAP-$BTP^{2+}$for the $1^{st}$ (black) and $100^{th}$ (orange) cycles at a scan rate of 50 mV $s^{-1}$. The $c_1/a_1$ and $c_2/a_2$ indicate the first and second cathodic/anodic events, respectively. The orange circle and the adjacent arrow indicate the starting point and direction of the potential scan, respectively. (b) Scan rate-dependent CV curves from 10 to 500 mV $s^1$. (c) CV curves concentrated on the ci/ai events for 100 cycles at 50 mV (d) Cathodic linear sweep voltammetries (LSVs) for single electron-transfer process with increasing rotating rates of an electrode from 400 to 2025 rpm. (e) DFT-calculated redox potentials and frontier orbitals of TMAP-$BTP^{2+}$ and TMAP-$BTP^{\cdot+}$.
Figure 9:
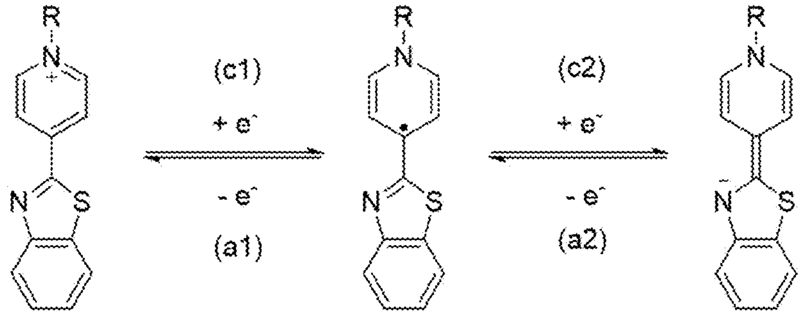
FIG. 9—Redox process of BTP derivatives through two-step electron transfer.

The anodic-to-cathodic peak current ratio ($I_{pa}/I_{pc}$) was close to unity, and the peak-to-peak potential difference (66 $E_p$) was maintained at 105 mV for 100 cycles ((c) of FIG. 8). This reflects a stable pyridinium redox reaction. Furthermore, the reduced form of TMAP-$BTP^{2+}$ (i.e., TMAP-$BTP^{\cdot+}$ as the distonic radical cation) remained stable for 4 days in the electrolyte solution (0.22% per day, FIG. 10). Density functional theory (DFT) calculations were conducted employing the B3LYP-D3/6-31G/cc-pVTZ(-f) level of theory, as implemented in the Jaguar software package, to better understand the redox-properties of TMAP-$BTP^{2+}$. The calculated redox potential for the first TMAP-$BTP^{2+/\cdot+}$ redox couple was −1.18 V vs. $Fc/Fc^+$ ((e) of FIG. 8**), in excellent agreement with the experimental results.

The redox-active molecular orbitals (RAMO) of TMAP-$BTP^{2+}$ and its reduced form illustrate that the resonance-based delocalization of excess electrons established through the H-accepting benzothiazole moiety lowers the singly occupied molecular orbital (SOMO) and the highest occupied molecular orbital (HOMO) energies during the reduction process. The electron delocalization as such strengthens the planar molecular structure of the redox couple and suppresses structural distortion due to a plane, thereby greatly contributing to stabilization of various redox states.

Figure 11:
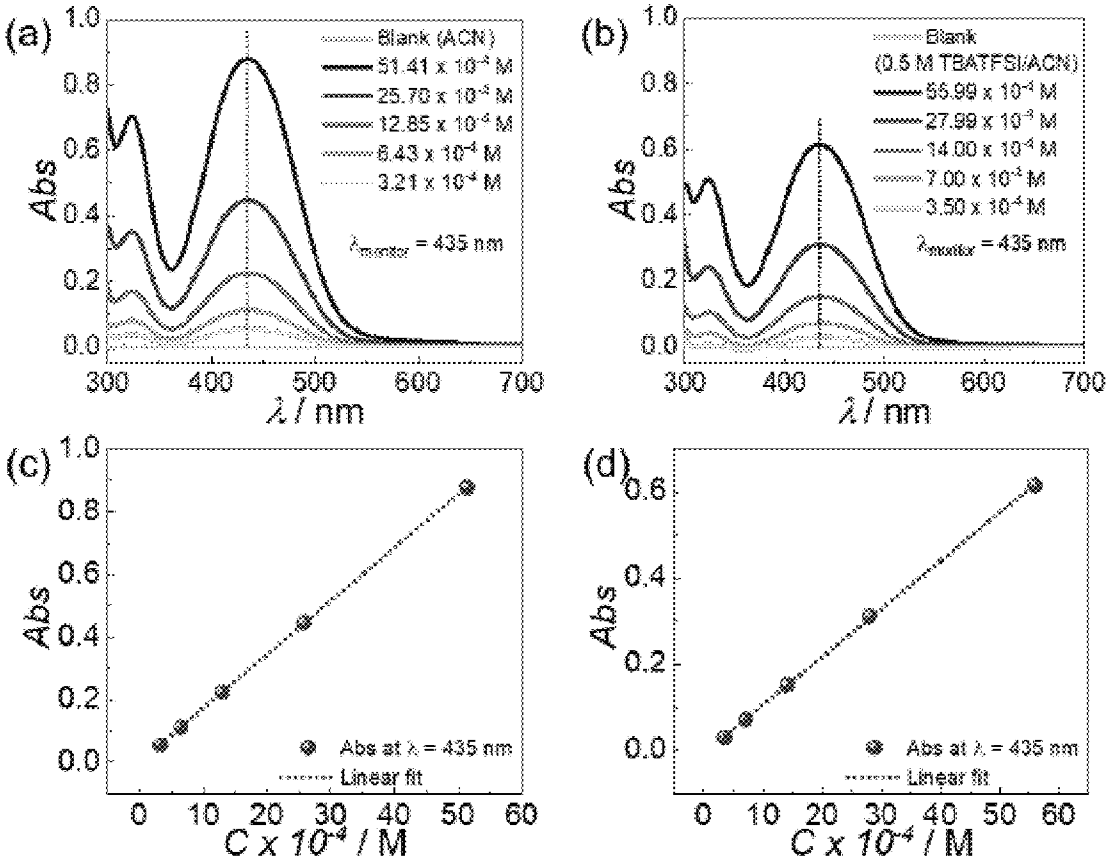
FIG. 11—UV-Vis spectra of BTMAP-$Fc\cdot 2TFSI^-$ with different concentrations in (a) MeCN and (b) electrolyte solution (0.5 M TBATFSI/MeCN). Corresponding calibration curves of BTMAP-$Fc\cdot 2TFSI^-$ in (c) MeCN and (d) the electrolyte solution. The maximum solubility of BTMAP-$Fc\cdot 2TFSI^-$ is 2.0 M and 1.58 M in MeCN and the electrolyte solution, respectively.
Figure 12:
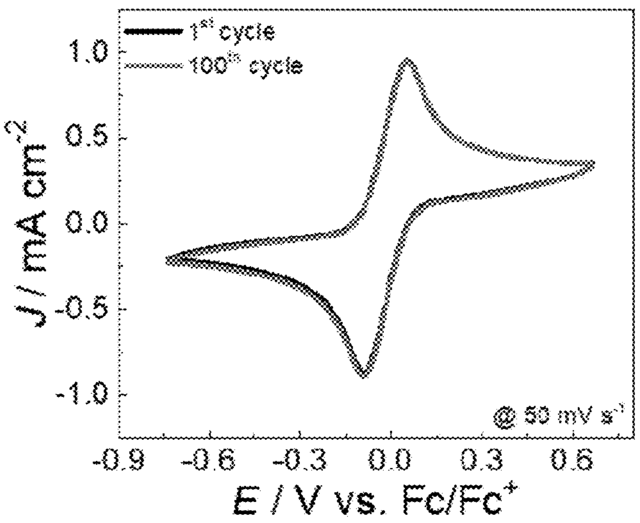
FIG. 12—CVs of 4 mM BTMAP-$Fc\cdot 2TFSI^-$ in 0.1 M TBATFSI/MeCN at a scan rate of 50 mV $s^{-1}$.

Meanwhile, the solubility of BTMAP-Fc having $2TFSI^-$ was ~2.0 M in MeCN and ~1.6 M in the electrolyte solution, was −0.03 V vs. $Fc/Fc^+$, and D and $k^o$ for the oxidation process were $2.0\times10^{-6}$ $cm^2$ $s^{-1}$ and 0.034 cm $s^{-1}$, respectively (Table 4, FIG. 11, FIG. 12). During 100 CV cycles, $I_{pa}/I_{pc}$ of about 1 and $\Delta E_p$ of ~150 mV were maintained, and thus, BTMAP-Fc also showed high stability.

Stability of TMAP-$BTP^{2+/\cdot+}$ was further analyzed using the galvanostatic mode in unbalanced compositionally symmetric RFBs. An AEM (FAPQ-275-PET, Fumasep) was applied to the RFB, which ideally interferes with the crossovers of $TMAP-BTP^{2+}$ and $TMAP-BTP^{\cdot+}$ while enabling the entry and exit of anion and neutral molecules. The permeability of $TMAP-BTP^{2+}$ and $TMAP-BTP^{\cdot+}$ through AEM was $3.64\times10^{-9}$ $cm^2$ $s^{-1}$ and 1.44x 10' $cm^2$ $s^{-1}$, respectively, and thus, was confirmed to have a very slow permeability (FIG. 13).

Figure 13:
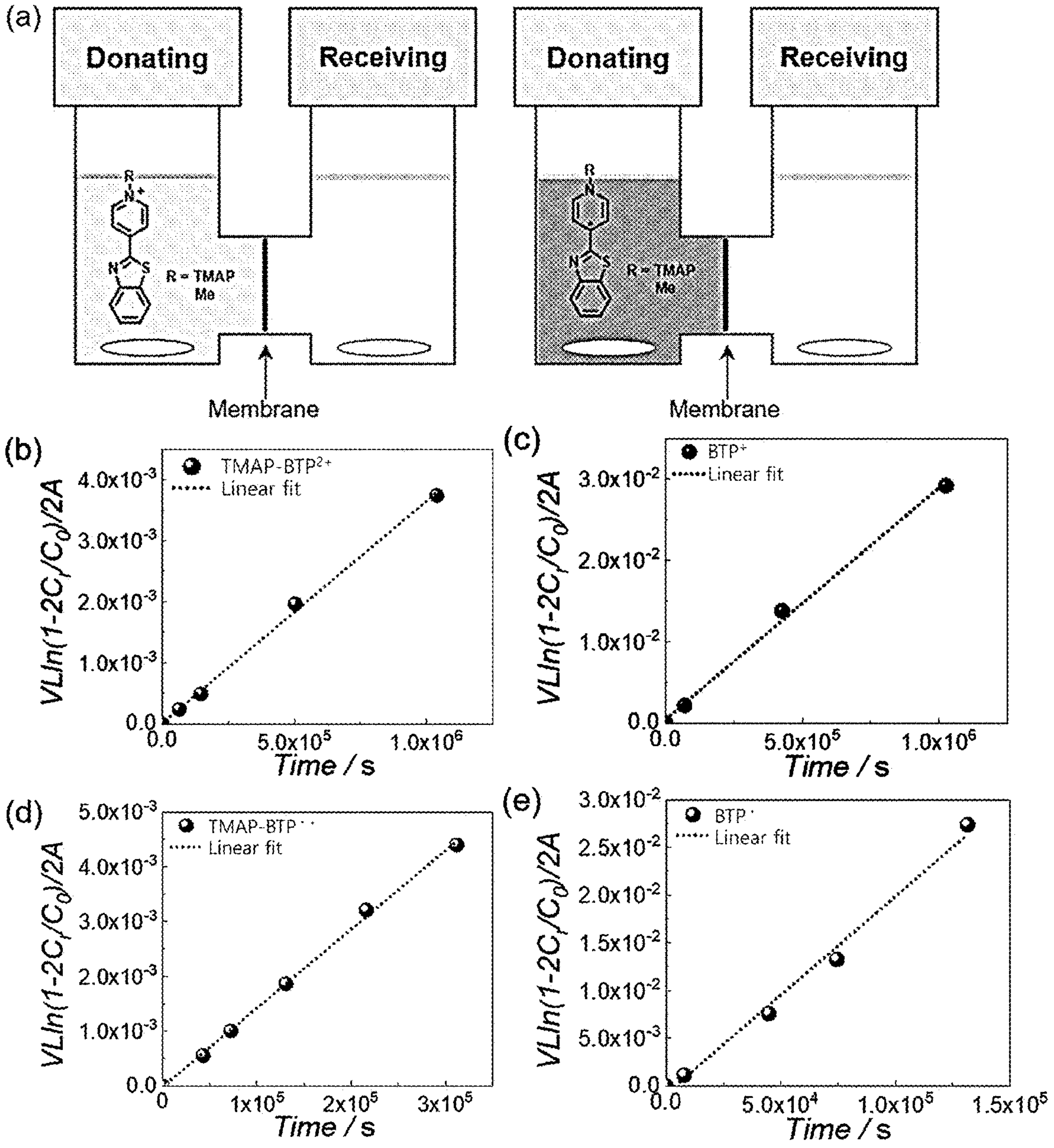
FIG. 13—Time-dependent crossover tests. (a) Schematic illustration of H-cell tests to investigate the permeability of TMAP-$BTP^{2+}$, $BTP^+$, and their reduced forms. 50 mM redox molecule examined in a static H-cell where a blank electrolyte solution was positioned on the other side, the receiving part. The ionic strengths for both sides of the electrolyte solutions were balanced to rule out the osmosis effect. (b-e) Permeability curves of (b) 50 mM TMAP-$BTP^{2+}$, (c) 50 mM $BTP^+$, (d) 50 mM TMAP-$BTP^{\cdot+}$, and (e) 50 mM $BTP^{\cdot}$. Permeability was measured to $3.64\times10^{-9}$ $_{cm}{}^2$ $s^{-1}$, $2.85\times10^{-8}$ $cm^2$ $s^{-1}$, $1.44\times10^{-8}$ $cm^2$ $s^1$, and $2.07\times10^{-7}$ $cm^2$ $s^{-1}$, respectively. It is expected 0.37, 0.047, 0.094 and 0.0065 year required for 10% decay associated with the crossover, respectively.
Figure 14:
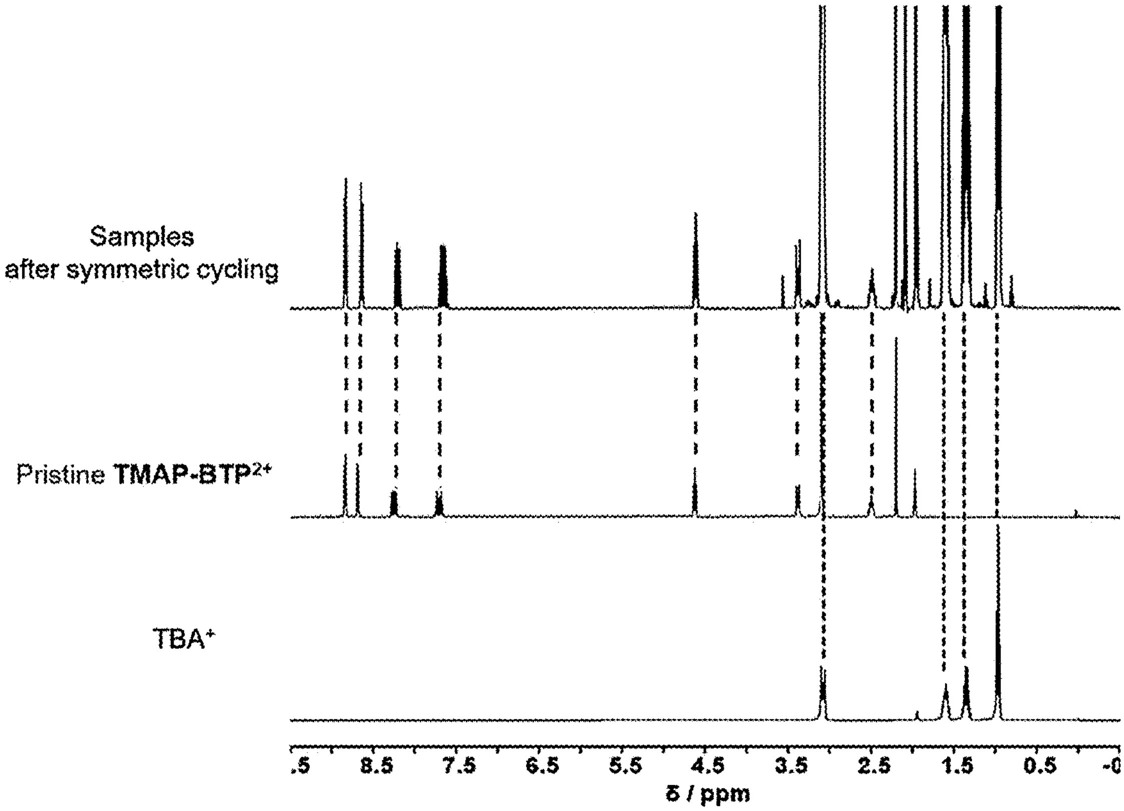
FIG. 14—Post-mortem $^{1-}$El NMR analysis of negolyte-side solution in the symmetric RFB s.

For symmetric RFB tests, we used a 1:1 $TMAP-BTP^{2+}$ and $TMAP-BTP^{\cdot+}$ mixture, which was reduced on the negolyte side and oxidized on the posolyte side during the charging process ((a) of FIG. 13). The first charging capacity approached 2.314 Ah $L^{-1}$, reflecting ~86% utilization of the redox couple ((b) of FIG. 13). The galvanostatic cyclability of $TMAP-BTP^{2+/\cdot+}$ were confirmed to be excellent since a capacity of ~90% was maintained for 250 cycles or more (total 106.4 hours of operation) and CE of ~99.85% was shown at a current density of 18 mA $cm^{-2}$ (equal to 4 C rate) ((b)-(c) of FIG. 13). The capacity-fading rate estimated per cycle was ~0.0083% for 250 cycles or more, and as confirmed by post-mortem $^1H$ nuclear magnetic resonance ($^1H$ NMR) spectroscopy (FIG. 14), insignificant chemical disproportionation and minimal undesired reactions were shown. It was confirmed therefrom that the cationic TMAP group repelled the redox molecule and prevented a chemical reaction, in addition to the stabilization of the pyridinyl radical by benzothiazole.

A posolyte solution including $BTMAP-Fc^{2+}$ having $2TFSI^-$ (that is, BTMAP-Fc2·$TFSI^-$, hereinafter, referred to as "BTMAP-Fc") as a positive electrode active material and a negolyte solution including $TMAP-BTP^{2+}$ as a negative electrode active material were used to evaluate full RFB performance. A redox potential of BTMAP-Fc (−0.03 V vs. $Fc/Fc^+$) was not sufficiently high, but BTMAP-Fc is one of a few positive electrode active materials having sufficient solubility and stability with the crossover-suppressing ability of the TMAP group.

Figure 15:
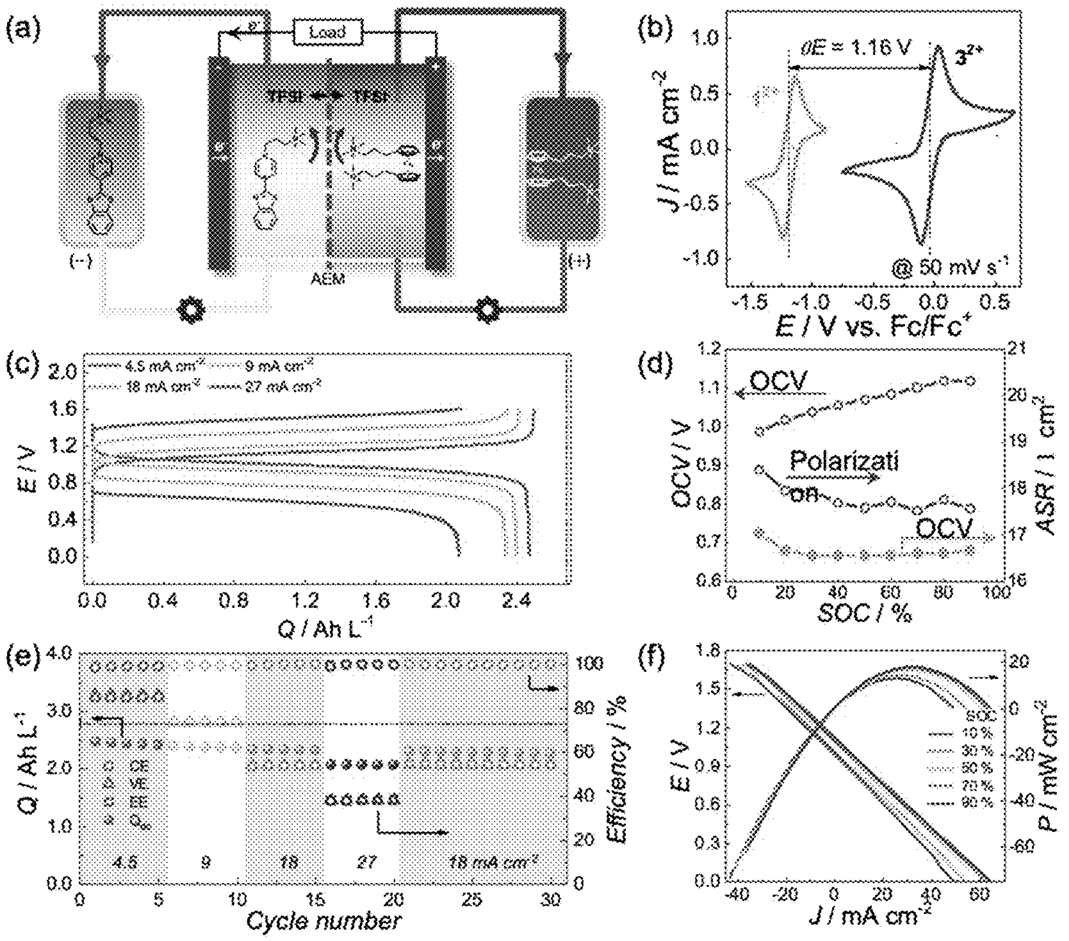
FIG. 15—Rate capability and polarization curves of full RFBs consisting of 0.1 M TMAP-$BTP^{2+}\cdot 2TFSI^-$||0.15 M BTMAP-$Fc\cdot 2TFSI^-$ in 0.5 M TBATFSI/MeCN solution. AEM was used as the separator. 10 mL of each negolyte and posolyte solution was circulated at a flow rate of 60 mL/min in an Ar-filled glove box. (a) Schematic illustration of a full RFB. (b) Combined CV curves of TMAP-$BTP^{2+}$ (orange) and BTMAP-Fc (black) at a scan rate of 50 mV $s^1$. (c) Galvanostatic curves at current density of 4.5 $mA/cm^2$ (brown), 9 $mA/cm^2$ (yellow), 18 $mA/cm^2$ (pale green), and 27 $mA/cm^2$ (green). (d) OCV and area-specific resistances (ASRs) at OCV and polarization tests from 10 to 90% SOC. (e) Rate capability tests in the range of 4.527 $mA/cm^2$ current density. VE and EE indicate voltage efficiency and energy efficiency, respectively. (f) Polarization curves with different SOCs acquired after the charging process at 9 $mA/cm^2$.

The assembled full RFBs consisted of 0.1 M $TMAP-BTP^{2+}$ negolyte and 0.15 M BTMAP-Fc posolyte in a 0.5 M TBATFSI/MeCN solution, which were separated through the AEM (FIGS. 15 and 16). $TMAP-BTP^{2+}$ played a decisive role in the determination of the RFB performance with an excess of BTMAP-Fc. A working voltage of ~1.16 V was employed, estimated from the CV profiles ((b) of FIG. 15). The AEMs were stable, as demonstrated by the constant area-specific resistance (ASR) of 16.5-17.0 Ω $cm^2$ at open-circuit voltage (OCV), throughout the growing state of charge (SOC) ((d) of FIG. 15). In addition, the full RFB provided a first charging capacity of 2.50 Ah/L which is 93.28% of the theoretical capacity at a current density of 4.5 mA/$cm^2$, and showed CE of >98.96% and an energy efficiency (EE) of ~86% (c of FIG. 15). Rate capability verified the stable RFB performance ((e) of FIG. 15). Notably, when the current rate was increased to 27 mA $cm^{-2}$, the capacity decreased by only 14% as compared to that at 4.5 mA $cm^{-2}$. A polarization curve showed a maximum power density (MPD) of 17.8 mW/$cm^2$ at 90% SOC ((f) of FIG. 15). An ASR was 17.5-18.5 Ω $cm^2$ in the polarization curves, where the resistance of AEM accounted for ~94% ((c) of FIG. 15). Although the ASR of the AEM in the non-aqueous medium is higher than that in the aqueous medium (<2.5 Ω $cm^2$ in 0.5 M NaCl), the resistance was similar to the resistance of a commercial porous membrane (Daramic, 5-23 Ω $cm^2$) and a cross-linked microporous polymer (~10 Ω $cm^2$), and was largely lower than the resistance of a nanoporous aramid membrane.

Figure 17:
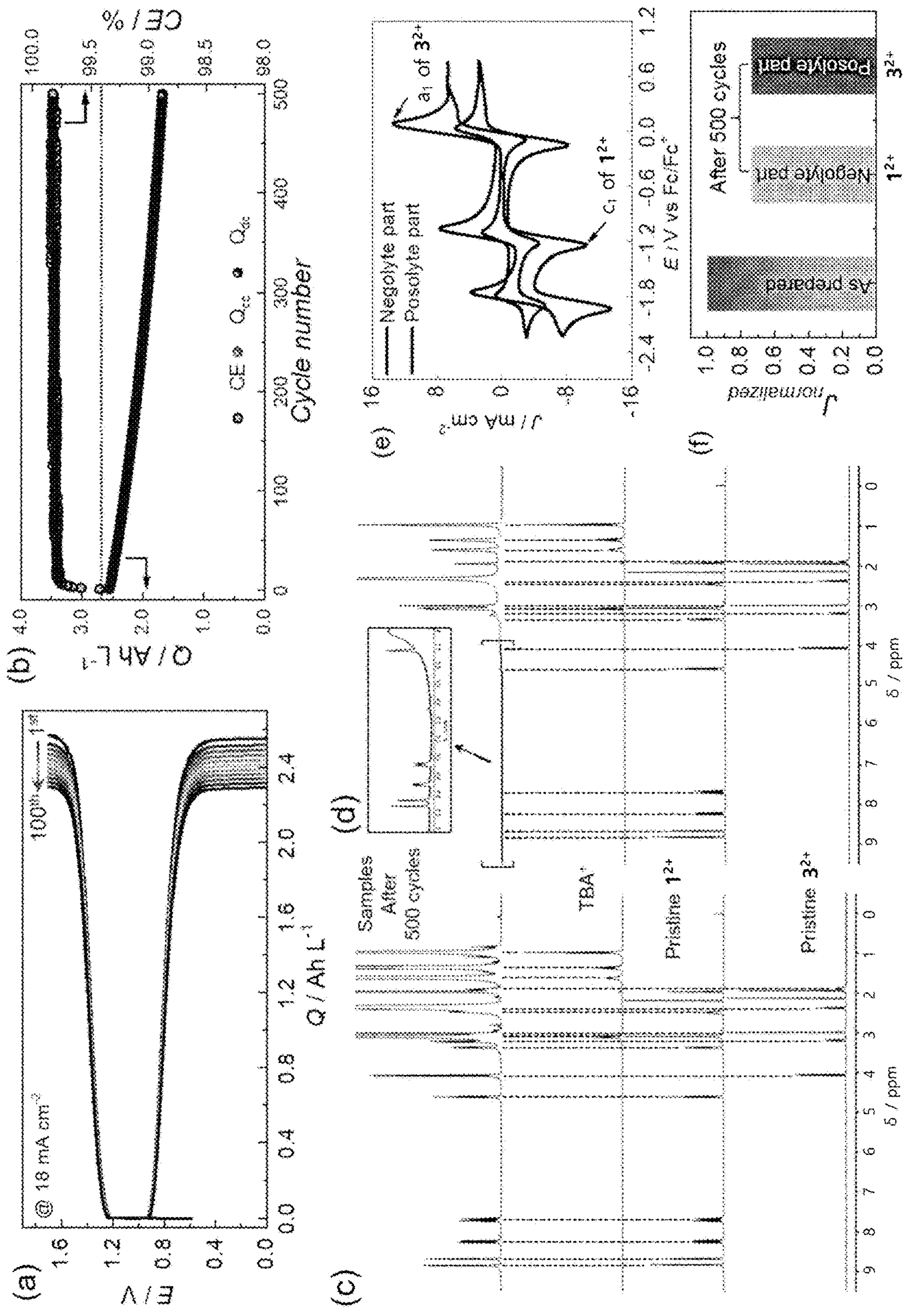
FIG. 17—Long-term cyclability of full RFBs comprised of 0.1 M TMAP-$BTP^{2+}\cdot 2TFSI^-$||0.15 M BTMAP-$Fc\cdot 2TFSI^-$ in 0.5 M TBATFSI/MeCN solution. 10 mL of each negolyte and posolyte solution was circulated at a flow rate of 60 mL/min in an Ar-filled glove box. (a) Galvanostatic curves for 100 cycles at a current density of 18 $mA/cm^2$. (b) Corresponding cycling profile for 500 cycles. (c-d) $^1$I-INMR spectra of (c) 500-times cycled negolyte-side solution, and (d) 500-times cycled posolyte-side solution. The inset is a high-magnified spectrum in 4~10 ppm. (e) Post-mortem CV analysis of negolyte- (brown) and posolyte-side electrolyte solution (pale green) after 500 cycles. A scan rate was 50 mV $s^1$. (f) Comparative current density of the emerging $c_1$ of TMAP-$BTP^{2+}$ in the negolyte-side and the $a_1$ of BT-MAP-Fc 의 in the posolyte-side solution.
Figure 18:
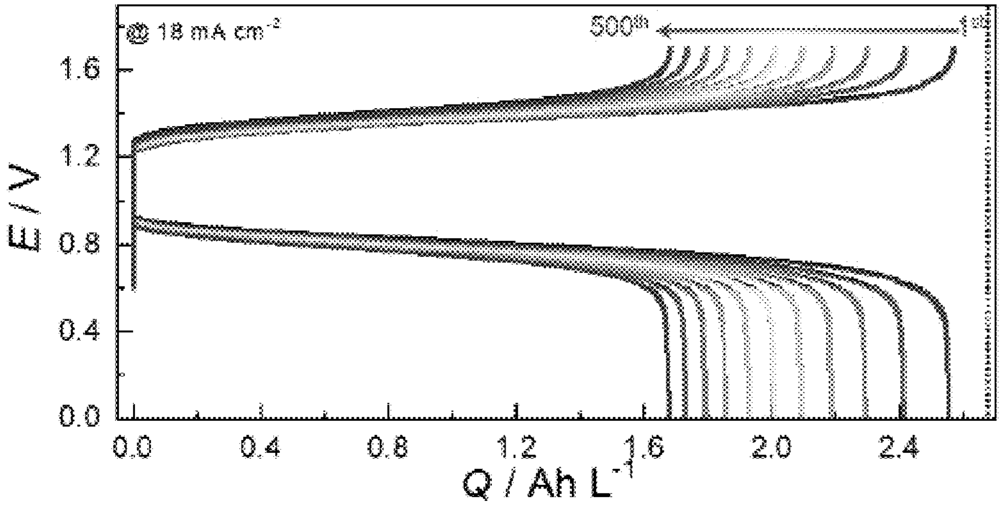
FIG. 18—Full-cell galvanostatic cycles of 0.1 M TMAP-$BTP^{2+}\cdot 2TFSI^-$||0.15 M BTMAP-$Fc\cdot 2TFSI^-$ in 0.5 M TBATFSI/MeCN for 500 cycles. 10 mL of each negolyte and posolyte solution was circulated at a flow rate of 60 mL/min and at a current density of 18 $mA/cm^2$ in an Ar-filled glove box.

Long-term cyclability of the full RFBs was evaluated at a current density of 18 mA $cm^{-2}$. After 100 and 500 cycles, 89.8 and 65.7% of the first charging capacity (2.57 Ah $L^{-1}$) was maintained ((a) of FIG. 17), with the average CE exceeding 99.80% for 500 cycles (FIG. 18). The capacity-fading rate was 0.08% per cycle for 500 cycles ((b) of FIG. 17), superior to previously reported negolytes in terms of cyclability and utilized concentration. After 500 cycles, post-mortem analyses were conducted on both sides of the electrolyte solutions. $^1H$ NMR spectrum of the negolyte-side solution exhibited a negligible side product related to $TMAP-BTP^{2+}$ ((c) of FIG. 17), indicating excellent chemical stability of $TMAP-BTP^{2+}$. Monotonous capacity fading over 500 cycles implied that a gradual crossover occurred throughout the long-term cycles. The signals of $TMAP-BTP^{2+}$ and BTMAP-Fc were found in both the negolyte solution and the posolyte solution ((d) of FIG. 17). Consistent with this, CV analysis also showed cl wave of $TMAP-BTP^{2+}$ in both solutions; however, a ~2.75 times higher current density was noticed on the negolyte side ((e)-(f) of FIG. 17). It is recognized therefrom that a loss of $TMAP-BTP^{2+}$ (about 26.7% after 500 cycles) by crossover was resulted from a loss of a total capacity (~34.3%).

Figure 10:
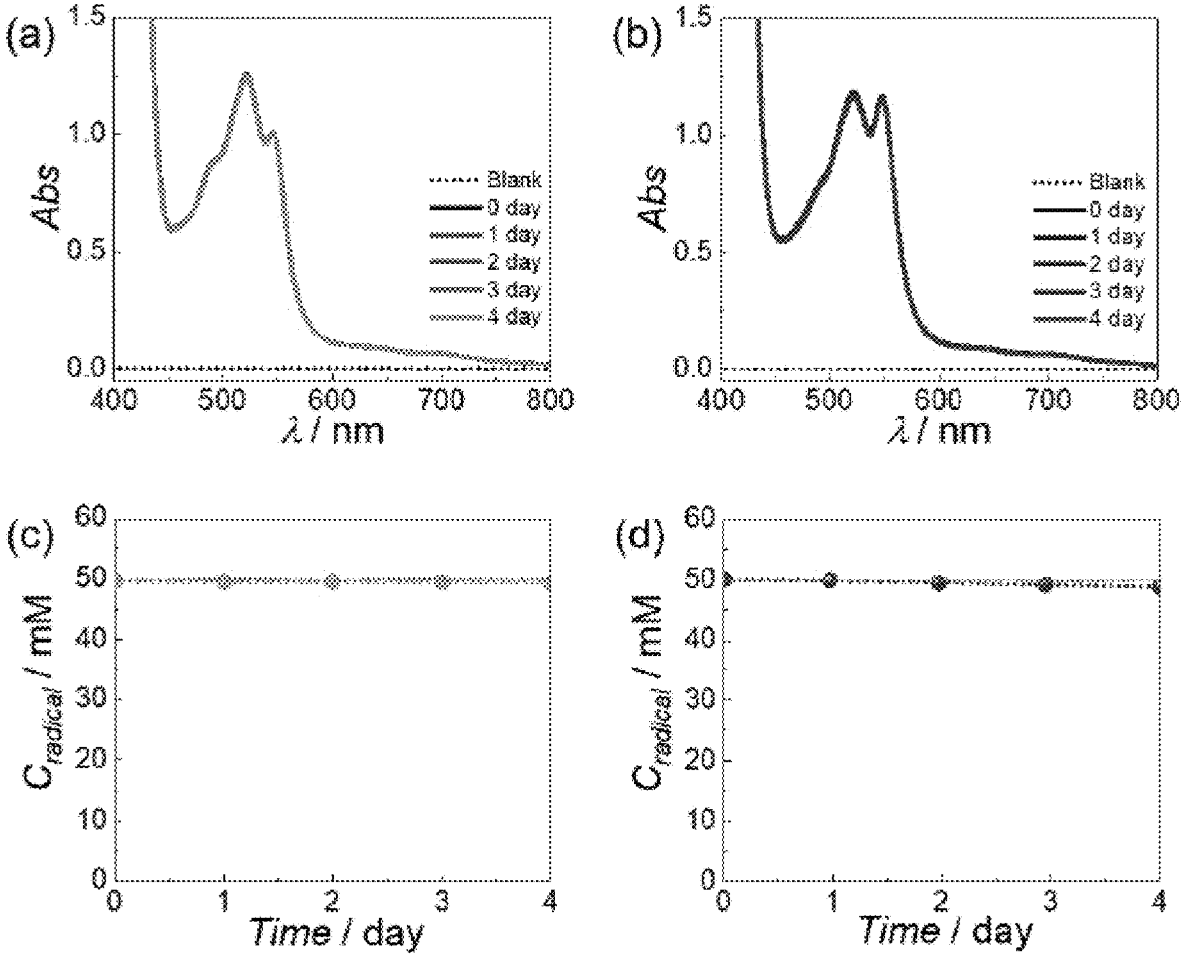
FIG. 10—Radical stability of TMAP-$BTP^{\cdot+}$ and $BTP^{\cdot}$. (a-b) UV-Vis spectra of (a) TMAP-$BTP^{\cdot+}$ and (b) $BTP^{\cdot}$ in 0.5 M TBATFSI/MeCN. (c-d) Calculated time-dependent concentration decay of (c) TMAP-$BTP^{\cdot+}$ (0.22%/day) and (d) BTP (0.63%/day). Better stability of TMAP-$BTP^{\cdot+}$ than $BTP^{\cdot}$ is presumably attributed to the cationic TMAP groups, which repel the redox molecules and prevent chemical reactions.
Figure 19:
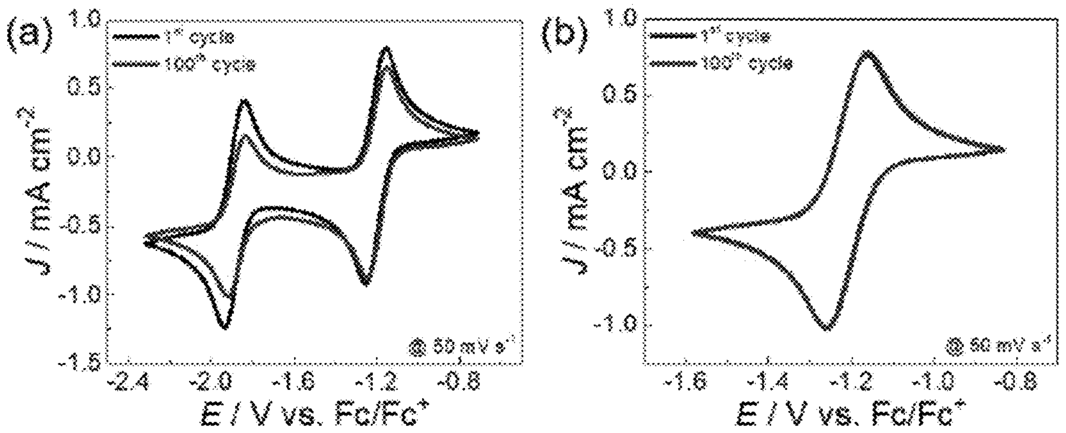
FIG. 19—CVs of 4 mM $BTP^+\cdot TFSI^-$ in 0.1 M TBATFSI/MeCN at a scan rate of 50 mV $s^{-1}$ with (a) consecutive two redox processes and (b) single redox reaction. The formal potentials for the first and second redox events are −1.21 V and −1.90 V vs. $Fc/Fc^+$, respectively. For 100 CV, 1.01 of $I_{pa}/I_{pc}$ and ~99 mV of $\Delta E_p$ were preserved.
Figure 20:
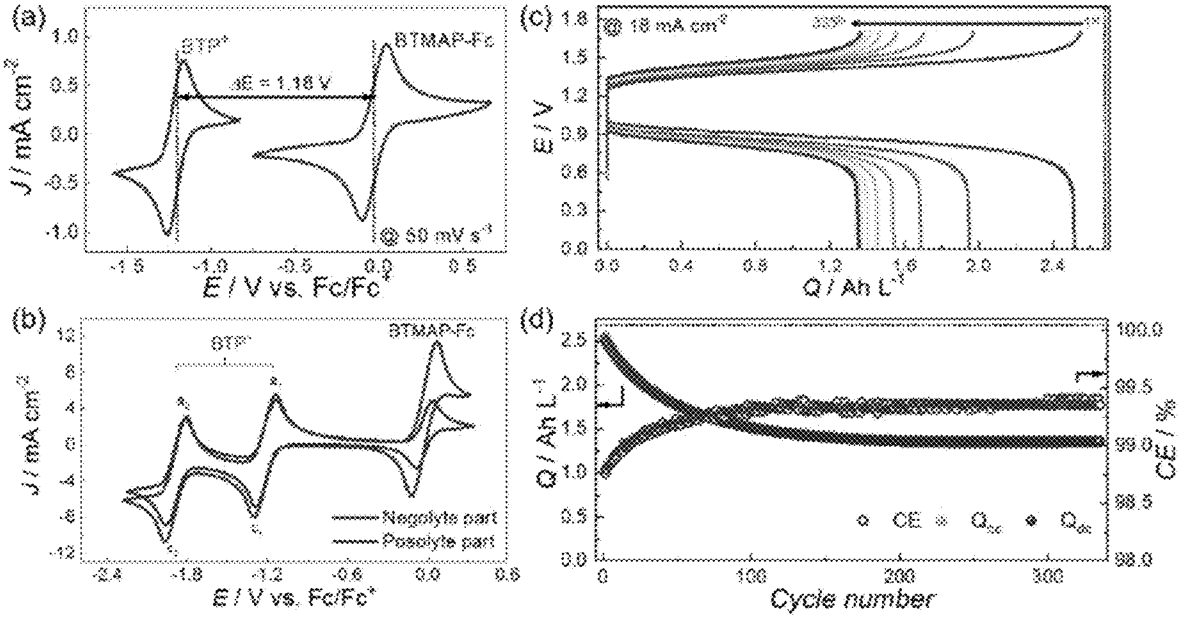
FIG. 20—Full redox-cell performance of 0.1 M $BTP^+\cdot TFSI^-$||0.15 M BTMAP-$Fc\cdot 2TFSI^-$ in 0.5 M TBATFSI/MeCN. 10 mL of each negolyte and posolyte solution was circulated at a flow rate of 60 mL/min in an Ar-filled glove box. (a) Combined CV curves of $BTP^+$ and BTMAP-Fc at a scan rate of 50 mV (b) Post-mortem CV analysis of negolyte-part (green) and posolyte-part (black) solution after galvanostatic 335 cycles. (c) Galvanostatic curves for 335 cycles at a current density of 18 mA $cm^{-2}$. (d) Corresponding cycling profile. CE, $Q_{cc}$, and $Q_{ac}$ indicate Coulombic efficiency, charging capacity, and discharging capacity, respectively.
Figure 21:
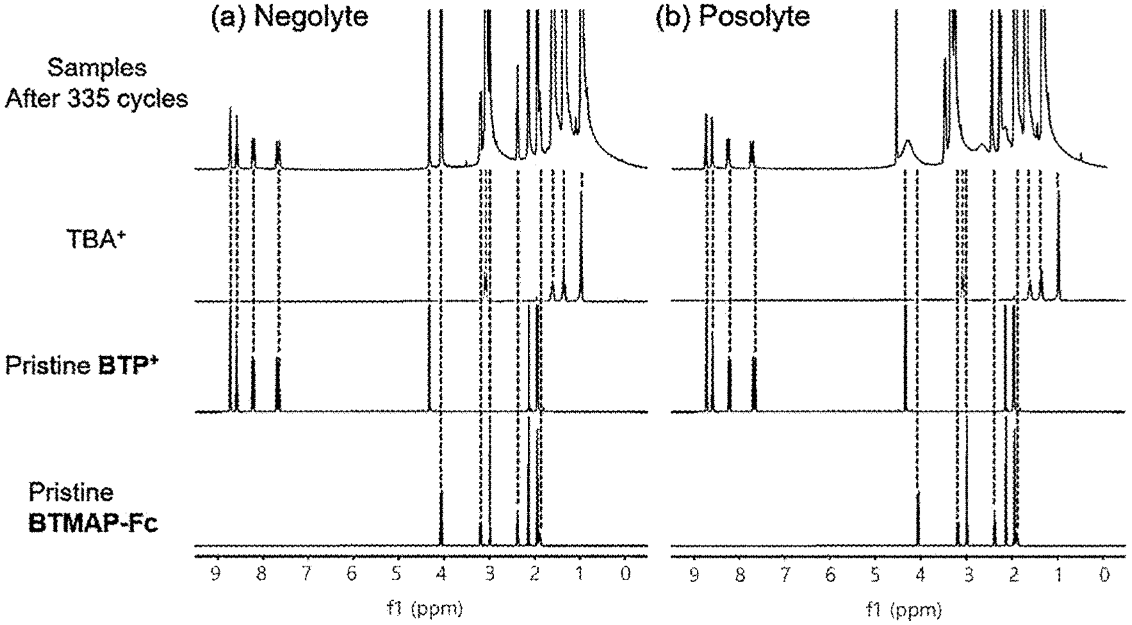
FIG. 21—$^1$H NMR analysis of (a) negolyte and (b) posolyte-side electrolyte solutions of full RFBs including $BTP^+$and BTMAP-Fc.
Figure 22:
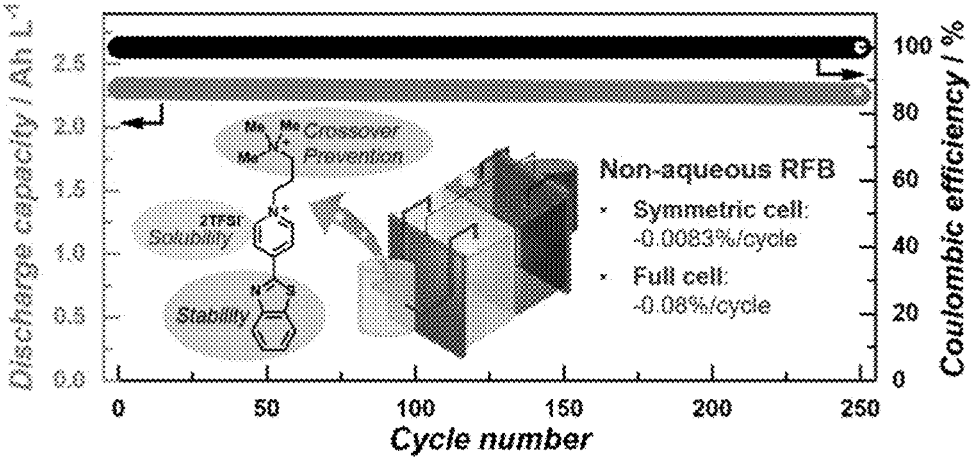
FIG. 22—A Representative drawing of the disclosure.

Nevertheless, as a result of using $TMAP-BTP^{2+}$, crossover was significantly suppressed as compared with the case of a pyridinium ion $BTP^+$ with a neutral methyl group loaded (FIG. 10, FIG. 19, and Table 4). The permeabilities of $BTP^+$and the neutral pyridinyl radical $BTP^{\cdot}$ through the AEM were $2.85\times10^{-8}$ and $2.07\times10^{-7}$ $cm^2$ $s^{-1}$, respectively (FIG. 13), higher than those of $TMAP-BTP^{2+}$ and $TMAP-BTP^{\cdot+}$ species. As expected, the full RFBs comprising the $BTP^+$ negolyte and the BTMAP-Fc posolyte demonstrated rapid decay of capacity, approaching ~60% of the initial capacity after 100 cycles. However, in the subsequent cycles, the capacity fading retarded, and ~50% capacity was maintained after 220 and 335 cycles (FIG. 20). Though the $^1H$ NMR spectrum did not show formation of by-products after 335 cycles, a clear BTMAP-Fc signal was found in the spectrum of a negolyte-side solution, and a $BTP^+$ peak was found in the spectrum of a posolyte-side solution (FIG. 21). The CV curve showed $BTP^+$ having similar cl intensity for both the negolyte solution and the posolyte solution ((b) of FIG. 20), and it was shown that a capacity loss occurred until the same concentration of $BTP^+$ was present in the negolyte- and posolyte-side tanks. In contrast, the anodic CV wave of BTMAP-Fc was 2.3 times more intense in the posolyte solution than in the negolyte solution, and thus, the advantage of TMAP itself in conjunction with the AEM system was confirmed.

The heteroaryl-pyridinium compound according to the present disclosure has a structure in which a 5-membered heteroazole is introduced to a C4-position of pyridinium and has further improved molecular stability due to extension of π-conjugation of a pyridinium molecule. In addition, the heteroaryl-pyridinium compound according to the present disclosure has a high solubility in various solvents, in particular, in non-aqueous solvents. Besides, the heteroaryl-pyridinium compound according to the present disclosure may be included in an electrolyte solution of a redox flow battery to suppress crossover.

In particular, the heteroaryl-pyridinium compound according to the present disclosure, that is, a divalent dicationic heteroaryl-pyridinium compound in which an ammonium functional group is introduced to a N-substituent of a pyridinium core may be used as a negative electrode active material to form a negolyte solution of a redox flow battery, and in this case, crossover of the negolyte solution through an anion exchange membrane may be significantly suppressed and undesired intermolecular interaction may be suppressed.

In addition, when an electrolyte solution including the heteroaryl-pyridinium compound according to the present disclosure as a negative electrode active material is adopted in a redox flow battery, crossover was suppressed, and capacity-fading rates of about 0.0083% per cycle for 250 cycles in a symmetric cell and about 0.08% for 500 cycles in a full cell were implemented.

Hereinabove, the embodiments of the present disclosure have been described in more detail with reference to the attached drawings; however, the present disclosure is not necessarily limited to the embodiments and may be variously modified and carried out within the scope not departing from the spirit of the present disclosure. Accordingly, the embodiments disclosed in the present disclosure are not for limiting but for describing the spirit of the present disclosure, and the scope of the spirit of the present disclosure is not limited by the embodiments. The scope of the present disclosure should be interpreted by the following claims and it should be interpreted that all spirits equivalent to the following claims fall within the scope of the present disclosure.

What is claimed is:

1. A heteroaryl-pyridinium compound represented by the following Chemical Formula 1 or Chemical Formula 2:

[Chemical Formula 1]

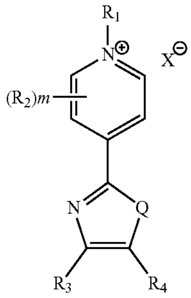

[Chemical Formula 2]

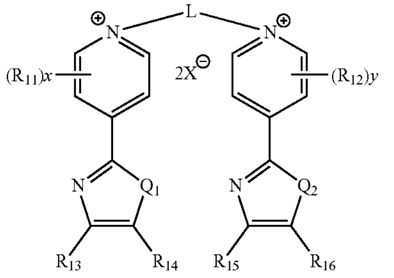

wherein $R_1$ is $C_1$-$C_{20}$alkyl and the alkyl of $R_1$ may be further substituted with $C_1$-$C_{20}$ alkoxy, cyano, or $* - \overset{\oplus}{N}R^aR^bR^cX^{\ominus}$;

$R^a$, $R^b$, and $R^c$ are independently of one another hydrogen or $C_1$-$C_{20}$alkyl;

L is $C_1$-$C_{20}$alkylene;

$R_2$, $R_{11}$, and $R_{12}$ are independently of one another $C_1$-$C_{20}$alkyl;

m, x, and y are independently of one another an integer of 0 to 4;

Q, $Q_1$, and $Q_2$ are independently of one another NR', O, or S;

R' is hydrogen or $C_1$-$C_{20}$alkyl;

$R_3$, $R_4$, and $R_{13}$ to $R_{15}$ are hydrogen, or $R_3$ and $R_4$, $R_{13}$ and $R_{14}$, and $R_{15}$ and $R_{16}$ may be connected to each other to form a fused ring; and $X^-$ is tetrafluoroborate ($BF_4^-$), hexafluorophosphate ($PF_6^-$), or bistriflimide ($TFSI^-$).

2. The heteroaryl-pyridinium compound of claim 1, wherein $R_3$ and $R_4$, $R_{13}$ and $R_{14}$, and $R_{15}$ and $R_{16}$ are connected by

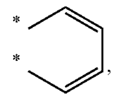

respectively to form a fused ring.

3. The heteroaryl-pyridinium compound of claim 1, wherein the heteroaryl-pyridinium compound is represented by the following Chemical Formula 3, Chemical Formula 4, or Chemical Formula 5:

[Chemical Formula 3]

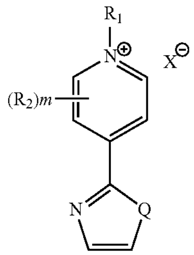

[Chemical Formula 4]

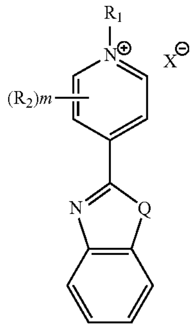

[Chemical Formula 5]

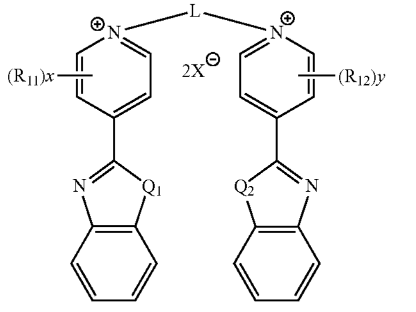

wherein $R_1$ is $C_1$-$C_{10}$ alkyl, $C_1$-$C_{10}$alkoxy$C_1$-$C_{10}$alkyl, cyano$C_1$-$C_{10}$alkyl, or -$L_1$-$N^+R^aR^bR^cX^-$;

$L_1$ is $C_1$-$C_{10}$alkylene;

$R^a$, $R^b$, and $R^c$ are independently of one another hydrogen or $C_1$-$C_{10}$alkyl;

L is $C_1$-$C_{10}$alkylene;

$R_2$, $R_{11}$, and $R_{12}$ are independently of one another $C_1$-$C_{10}$alkyl;

m, x, and y are independently of one another an integer of 0 to 2;

Q, $Q_1$, and $Q_2$ are independently of one another NR', O, or S;

R' is hydrogen or $C_1$-$C_{10}$alkyl; and $X^-$ is tetrafluoroborate ($BF_4^-$), hexafluorophosphate ($PF_6^-$), or bistriflimide ($TFSI^-$).

4. The heteroaryl-pyridinium compound of claim 3, wherein in Chemical Formula 3, $R_1$ is $C_1$-$C_{10}$alkyl, m is 0, and Q is S.

5. The heteroaryl-pyridinium compound of claim 3, wherein in Chemical Formula 4, $R_1$ is $C_1$-$C_{10}$alkyl, $C_1$-$C_{10}$alkoxy$C_1$-$C_{10}$alkyl, or $-L_1-N^+R^aR^bR^cX^-$, $L_1$ is $C_1$-$C_{10}$alkylene, $R^a$, $R^b$, and $R^c$ are independently of one another $C_1$-$C_{10}$alkyl, $R_2$ is $C_1$-$C_{10}$alkyl, m is an integer of 0 to 2, Q is NR', O, or S, R' is $C_1$-$C_{10}$alkyl, and $X^-$ is tetrafluoroborate ($BF_4^-$), hexafluorophosphate ($PF_6^-$), or bistriflimide ($TFSI^-$).

6. The heteroaryl-pyridinium compound of claim 3, wherein in Chemical Formula 5, L is $C_3$-$C_{10}$alkylene, x and y are 0, and $Q_1$ and $Q_2$ are S.

7. The heteroaryl-pyridinium compound of claim 5, wherein the heteroaryl-pyridinium compound is represented by the following Chemical Formula 4-1 or Chemical Formula 4-2:

[Chemical Formula 4-1]

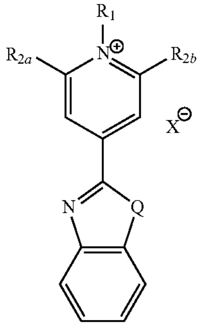

[Chemical Formula 4-2]

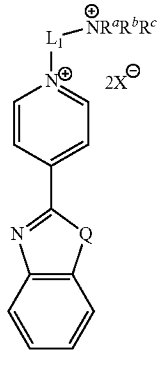

wherein $R_1$ is $C_1$-$C_{10}$alkyl or $C_1$-$C_{10}$alkoxy$C_1$-$C_{10}$alkyl;

$L_1$ is $C_1$-$C_{10}$alkylene;

$R^a$, $R^b$, and $R^c$ are independently of one another $C_1$-$C_{10}$alkyl;

$R_{2a}$ and $R_{2b}$ are hydrogen or $C_1$-$C_{10}$alkyl;

Q is NR', O, or S;

R' is $C_1$-$C_{10}$alkyl; and $X^-$ is tetrafluoroborate ($BF_4^-$), hexafluorophosphate ($PF_6^-$), or bistriflimide ($TFSI^-$).

8. The heteroaryl-pyridinium compound of claim 1, wherein the heteroaryl-pyridinium compound is selected from the following:

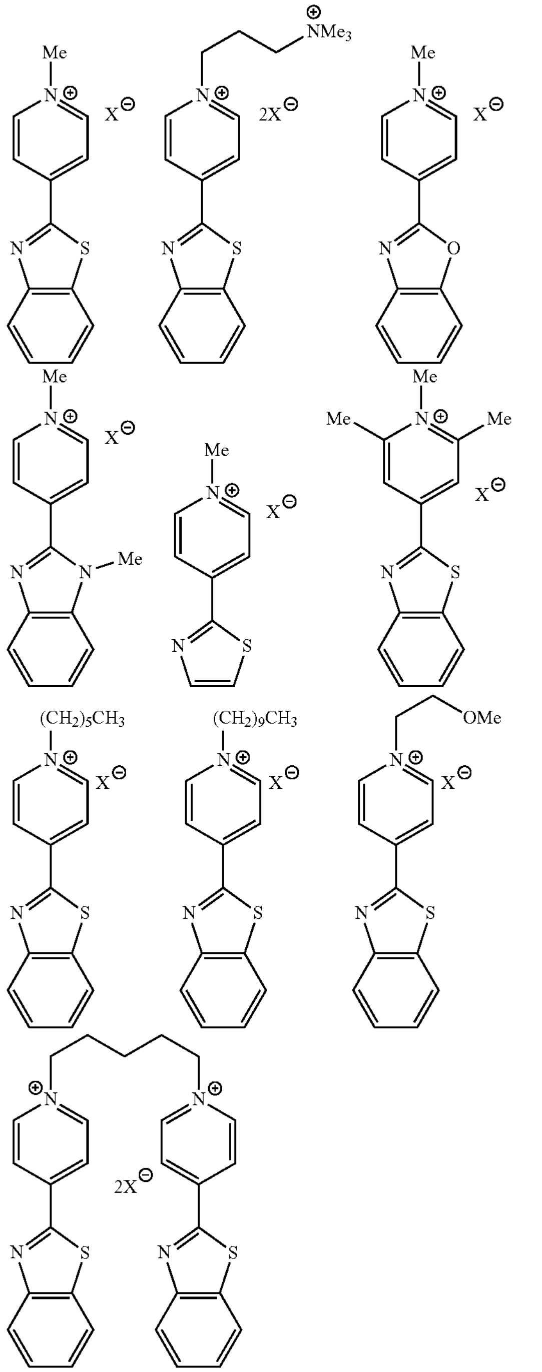

wherein $X^-$ is tetrafluoroborate ($BF_4^-$), hexafluorophosphate ($PF_6^-$), or bistriflimide ($TFSI^-$).

9. An electrolyte solution for a redox flow battery comprising the heteroaryl-pyridinium compound of claim 1.

10. The electrolyte solution for a redox flow battery of claim 9, further comprising: a solvent.

11. The electrolyte solution for a redox flow battery of claim 10, wherein the solvent is an aqueous solvent, a non-aqueous solvent, an ionic liquid, or a mixture thereof.

12. The electrolyte solution for a redox flow battery of claim 9, further comprising: a supporting electrolyte.

13. The electrolyte solution for a redox flow battery of claim 11, wherein the aqueous solvent is any one or more selected from the group consisting of sulfuric acid, hydrochloric acid, phosphoric acid, methanesulfonic acid, ithium hydroxide, sodium hydroxide, potassium hydroxide and cesium hydroxide;

the non-aqueous solvent is any one or more selected from the group consisting of dimethylacetamide (DMA), acetonitrile (MeCN), dimethyl carbonate, diethyl carbonate, methylethyl carbonate, dimethyl formamide, propylene carbonate, ethylene carbonate, N-methyl-2-pyrrolidone, fluoroethylene carbonate, γ-butyrolactone, dimethyl sulfoxide, diethyleneglycol dimethylether, triethyleneglycol, dimethylether, tetraethyleneglycol dimethylether, acetone, acetylacetone, 1,4-dioxane, 1,2-dimethoxyethane, 1,2-diethoxyethane, dichloromethane, 1,2-dichloroethane, nitrobenzene, nitromethane, tetrahydrofuran, 2-methyltetrahydrofuran, 2,4-dimethyltetrahydrofuran, methoxybenzene, diglyme, triglyme, tetraglyme, 4-methyl-2-pentanone, propionitrile, butyronitrile, isobutyronitrile, benzonitrile, sulfolane, dimethylthioformamide, methyl acetate, ethyl acetate, ethanol, and methanol; and the ionic liquid is an ammonium, imidazolium, morpholinium, phosphonium, piperidinium, pyridinium, pyrrolidinium, or a sulfonium-based ionic liquid.

14. The electrolyte solution for a redox flow battery of claim 12, wherein the supporting electrolyte is any one or more selected from the group consisting of an alkylammonium salt, a lithium salt, a sodium salt, and a potassium salt.

15. The electrolyte solution for a redox flow battery of claim 14, wherein the alkylammonium salt is any one or more selected from tetrabuthylammonium tetrafluoroborate ($TBABF_4$), tetrabuthylammonium perchlorate ($TBAClO_4$), tetrabutylammonium hexafluorophosphate ($TBAPF_6$), tetrabutylammonium chloride (TBACl), tetrabutylammonium bromide (TBABr), tetrabutylammonium iodide (TBAI), tetrabutylammonium bistriflimide (TBATFSI), tetraethylammonium tetrafluoroborate ($TEABF_4$), tetraethylammonium hexafluorophosphate ($TEAPF_6$), tetraethylammonium perchlorate ($TEAClO_4$), and tetraethylammonium bistriflimide (TEATFSI);

the lithium salt is any one or more selected from LiCl, LiI, LiBr, $LiNO_3$, $LiNO_2$, $LiPF_6$, $LiBF_4$, $LiAsF_6$, $LiSbF_6$, $LiClO_4$, $LiCH_3SO_3$, $LiCF_3SO_3$, $LiC(SO_2CF_3)_3$, $LiN(CF_3SO_2)_2$, $LiN(SOF)_2$, $LiN(SO_2C_2F_5)_2$, and $LiCH(CF_3SO_2)_2$;

the sodium salt is any one or more selected from NaCl, NaI, NaBr, $NaNO_3$, $NaNO_2$, $NaPF_6$, $NaBF_4$, $NaClO_4$, $NaCF_3SO_3$, $NaC(SO_2CF_3)_3$, $NaN(CF_3SO_2)_2$, $NaN(SOF)_2$, $NaN(SO_2C_2F_5)_2$, and $NaCH(CF_3SO_2)_2$; and the potassium salt is any one or more selected from KCl, KI, KBr, $KNO_3$, $KNO_2$, $KPF_6$, $KBF_4$, $KClO_4$, $KCF_3SO_3$, $KC(SO_2CF_3)_3$, $KN(CF_3SO_2)_2$, $KN(SOF)_2$, $KN(SO_2C_2F_5)_2$, and $KCH(CF_3SO_2)_2$.

16. A redox flow battery comprising the electrolyte solution for a redox flow battery of claim 9.

17. The redox flow battery of claim 16, wherein the redox flow battery includes a positive electrode cell including a positive electrode and a posolyte solution; a negative electrode cell including a negative electrode and a negolyte solution; and a separator disposed between the positive electrode cell and the negative electrode cell, wherein the negolyte solution is the electrolyte solution for a redox flow battery.

18. The redox flow battery of claim 17, wherein the posolyte solution is any one or more selected from the group consisting of 1,1'-dimethylferrocene, a salt of (ferrocenylmethyl)trimethylammonium, a salt of (ferrocenylmethyl) dimethylethylammonium, a salt of bis((3-trimethylammonio)propyl)ferrocene, 5,10-dimethyl-5,10-dihydrophenazine, 5,10-bis(2-methoxyethyl)-5,10-dihydrophenazine, (2,2,6,6-tetramethylpiperidin-1-yl)oxyl (TEMPO), 4-hydroxy-(2,2,6,6-tetramethylpiperidin-1-yl)oxyl (4-hydroxy-TEMPO), 4-amino-(2,2,6,6-tetramethylpiperidin-1-yl)oxyl (4-amino-TEMPO), a salt of N,N,N-2,2,6,6-heptamethylpiperidinyloxy-4-ammonium (TMA-TEMPO), a salt of $N^1,N^1,N^1,N^3,N^3$,2,2,6,6-nonamethyl-$N^3$-(piperidinyloxy) propane-1,3-bis(ammonium), a salt of 4-[3-(trimethylammonio)propoxy]-2,2,6,6-tetramethylpiperidine-1-oxyl (TMAP-TEMPO), N-ethylphenothiazine, N-ethyl-3,7-dimethylphenothiazine, N-ethyl-3,7-dimethoxyphenothiazine, N-(2-(2-methoxyethoxy)ethyl)phenothiazine, 3,7-dimethoxy-N-(2-(2-methoxyethoxy)ethyl)phenothiazine, 3,7-bis (2-(2-methoxyethoxy)ethoxy)-N-(2-(2-methoxyethoxy) ethyl)phenothiazine, 2,3-dimethyl-1,4-dimethoxybenzene, 2,5-dimethyl-1,4-dimethoxybenzene, 1,4-di-tert-butyl-2-methoxy-5-(2-methoxyethoxy)benzene), 1,4-di-tert-butyl-2-methoxy-5-(2-(2-methoxyethoxy)ethoxy)benzene, 1,4-di-tert-butyl-2,5-bis(2-methoxyethoxy)benzene, 1,4-di-tert-butyl-2,5-bis(2-(2-methoxyethoxy)ethoxy)benzene, a salt of N-(2,3-bis(diisopropylamino)cycloprop-2-en-1-ylidene)-N-isopropylpropan-2-aminium, and a salt of 2,3-bis(diisopropylamino)-1-(methylthio)cycloprop-2-en-1-ylium.

* * * * *